United States Patent
Bertozzi et al.

(10) Patent No.: US 9,410,966 B2
(45) Date of Patent: Aug. 9, 2016

(54) ISOTOPIC RECODING FOR TARGETED TANDEM MASS SPECTROMETRY

(71) Applicant: The Regents of the University of California, Oakland, CA (US)

(72) Inventors: Carolyn R. Bertozzi, Berkeley, CA (US); Brian P. Smart, Cupertino, CA (US); Austin A. Pitcher, Saint James, MN (US); Krishnan K. Palaniappan, Columbia, MO (US); Mark A. Breidenbach, New York, NY (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/156,175

(22) Filed: Jan. 15, 2014

(65) Prior Publication Data

US 2014/0199716 A1    Jul. 17, 2014

Related U.S. Application Data

(60) Provisional application No. 61/753,774, filed on Jan. 17, 2013.

(51) Int. Cl.
*G01N 24/00* (2006.01)
*C12Q 1/37* (2006.01)
*G01N 33/68* (2006.01)

(52) U.S. Cl.
CPC .................. *G01N 33/6848* (2013.01)

(58) Field of Classification Search
CPC ................. G01N 24/00; C12Q 1/37
USPC ............................. 436/173; 435/23
See application file for complete search history.

(56) References Cited

PUBLICATIONS

Pitcher, A.A. New Tools for Chemically Directed Proteomics; UC Berkely Electronic Thesis and Dissertations (Fall 2010) pp. 1-277, retrieved from http://escholarship.org/uc/item/2300q7xg on Feb. 25, 2015.*

Briedenbach et al. Mapping Yeast N-Glycosites With Isotopically Recoded Glycans; Molecular and Cellular Proteomics, vol. 11, No. 6 (Jan. 19, 2012) Supplementary Information, pp. S1-S6.*

Pitcher, Austin Arlo. New Tools for Chemically Directed Proteomes (2010). eScholarship, UC Berkeley Elactronic Thesis and Dissertations. Downloaded from http://escholarship.org/uc/search?entity=ucb_etd;startDoc=2201 on Jun. 9, 2015.*

Pitcher, Austin Arlo. New Tools for Chemically Directed Proteomes (2010). Proquest Dissertations and Thesis Full Text. Downloaded from http://search.proquest.com/pqdtft/docview/861336430/abstract/2D635E92252C4818PQ/43?accountid=14753 on Jun. 9, 2015.*

Whelan et al. Mass Spectrometry (LC-MS/MS) Site-Mapping of N-Gylcosylated Membrane Proteins for Breast Cancer Biomarkers; Journal of Proteome Research, vol. 8. (2009) pp. 4151-4160.*

Orlando et al. IDAWG: Metabolic Incorporation of Stable Isotope Labels for Quantitative Glycomics of Cultured Cells; Journal of Proteome Research, vol. 8 (2009) pp. 3816-3823.*

Email communication from M. Phillips, Librarian, UC Berkely Library dated Oct. 27, 2015.*

Breidenbach, et al., "Mapping yeast N-glycosites with isotopically recorded glycans", Mol Cell Proteomics, Jun. 2012, 11(6):M111. 015339. Epub Jan. 19, 2012.

Palaniappan et al. "Isotopic signature transfer and mass pattern prediction (IsoStamp): An enabling technique for chemically-directed proteomics", ACS Chem Biol, May 2011, 6(8):829-836.

* cited by examiner

*Primary Examiner* — Kagnew H Gebreyesus
*Assistant Examiner* — Paul Martin
(74) *Attorney, Agent, or Firm* — Bozicevic Field & Francis, LLP; Paula A. Borden; Glenn J. Foulds

(57) ABSTRACT

Aspects of the present disclosure include methods for detecting a low abundance protein and methods for identifying a site of N-glycosylation on a protein. In practicing methods according to certain embodiments, a eukaryotic cell is contacted with an isotopic labeling composition and isotopically labeled N-glycosylated peptides obtained from the eukaryotic cell are assessed by liquid chromatography-tandem mass spectrometry. A predetermined isotopic pattern in the mass spectrum is identified and amino acid sequences of the peptides containing the predetermined isotopic pattern are determined. Systems for identifying a predetermined isotopic pattern in mass spectra and determining amino acid sequences of peptides containing the predetermined isotopic pattern are also described.

18 Claims, 34 Drawing Sheets

Occupied high confidence N-glycosites detected in the *S. cerevisiae* proteome

| Systematic Name | Uniprot ID | Standard name | Occupied N-glycosites |
| --- | --- | --- | --- |
| YBR023C | P29465 | CHS3 | Asn 323 |
| YBR074W | P38244 | | Asn 121 |
| YBR078W | P38248 | ECM33 | Asn 209, 267, 279, 328 |
| YBR092C | P24031 | PHO3 | Asn 162, 315, 356, 390* |
| YBR093C | P00635 | PHO5 | Asn 315, 356*, 390* |
| YBR139W | P38109 | | Asn 339 |
| YBR162C | P38288 | TOS1 | Asn 236 |
| YBR171W | P33754 | SEC66 | Asn 12 |
| YBR229C | P38138 | ROT2 | Asn 173, 907 |
| YBR286W | P37302 | APE3 | Asn 85, 96, 115, 150, 162, 371, 427 |
| YCL043C | P17967 | PDI1 | Asn 117, 155, 425 |
| YCL045C | P25574 | EMC1 | Asn 106, 420 |
| YCR011C | P25371 | ADP1 | Asn 165 |
| YDL095W | P33775 | PMT1 | Asn 390 |
| <u>YDR055W</u> | Q12355 | PST1 | Asn <u>210</u>, <u>242</u> |
| YDR434W | Q04080 | GPI17 | Asn 299 |
| YEL001C | P40006 | IRC22 | Asn 93, 121 |
| YEL002C | P33767 | WBP1 | Asn 60, 332 |
| YEL040W | P32623 | UTR2 | Asn 261 |
| YEL060C | P09232 | PRB1 | Asn 594 |
| YFR018C | P43599 | | Asn 179 |
| YGL022W | P39007 | STT3 | Asn 539 |
| YGR014W | P32334 | MSB2 | Asn 1088 |
| YGR189C | P53301 | CRH1 | Asn 177, 201 |
| YGR282C | P15703 | BGL2 | Asn 202 |
| YHR028C | P18962 | DAP2 | Asn 63, 139 |
| YHR101C | P38813 | BIG1 | Asn 144 |
| <u>YHR188C</u> | P38875 | GPI16 | Asn <u>184</u> |
| YHR202W | P38887 | | Asn 305 |
| YIL015W | P12630 | BAR1 | Asn 268, 366, 398 |
| YJL002C | P41543 | OST1 | Asn 99, 400 |
| YJL171C | P46992 | | Asn 51, 99, 122, 174, 219, 249, 267, 300 |
| YJL172W | P27614 | CPS1 | Asn 176, 228 |
| YJL192C | P39543 | SOP4 | Asn 35 |
| YKL039W | P32857 | PTM1 | Asn 132 |
| YKL046C | P36091 | DCW1 | Asn 203, 240 |
| YLR066W | Q12133 | SPC3 | Asn 173 |
| YLR084C | Q12465 | RAX2 | Asn 333, 524, 640 |

FIG. 9A

Occupied high confidence N-glycosites detected in the S. cerevisiae proteome (cont.)

| Systematic Name | Uniprot ID | Standard name | Occupied N-glycosites |
| --- | --- | --- | --- |
| YLR413W | Q06689 | | Asn 194, 299 |
| YLR450W | P12684 | HMG2 | Asn 150 |
| YML052W | P54003 | SUR7 | Asn 47 |
| YML130C | Q03103 | ERO1 | Asn 53, 468 |
| YMR006C | Q03674 | PLB2 | Asn 80, 193, 491 |
| YMR008C | P39105 | PLB1 | Asn 78, 123, 170, 388, 513, 541 |
| <u>YMR058W</u> | P38993 | FET3 | Asn <u>244</u>, 265, <u>292</u>, <u>359</u>, <u>381</u> |
| <u>YMR200W</u> | Q03691 | ROT1 | Asn <u>139</u> |
| YMR238W | Q05031 | DFG5 | Asn 245 |
| <u>YMR297W</u> | P00729 | PRC1 | Asn <u>124</u>, <u>479</u> |
| YMR307W | P22146 | GAS1 | Asn 40, 57, 95, 149, 165, 253, 409 |
| YNL160W | P38616 | YGP1 | Asn 58/61, 87, 94, 100, 106, 118, 172, 239, 286 |
| YNL327W | P42835 | EGT2 | Asn 103, 161 |
| YNR067C | P53753 | DSE4 | Asn 886 |
| YOL011W | Q08108 | PLB3 | Asn 56, 82, 547 |
| YOL030W | Q08193 | GAS5 | Asn 24, 60, 166, 299, 344 |
| YOL154W | Q12512 | ZPS1 | Asn 28, 57, 217 |
| YOR320C | Q12096 | GNT1 | Asn 425 |
| YPL123C | Q02933 | RNY1 | Asn 37 |
| <u>YPL154C</u> | P07267 | PEP4 | Asn <u>144</u>, <u>345</u> |

Biochemically validated N-glycoproteins are in bold
<u>Proteins with mapped or partially mapped N-glycosites are indicated with underline</u>
*Sequence ambiguity between PHO3 and PHO5

FIG. 9B

| Protein Accession | Glyco-sites | Sequence | Charge | m/z [Da] | MH+ [Da] | Modifications | XCorr |
|---|---|---|---|---|---|---|---|
| YBR023C | 1 | NQDGSSKPnFTVE (SEQ ID NO:5) | 2 | 814.3737824 | 1627.740288 | N9(HexNAc) | 2.573860739 |
| YBR074W | 1 | SILFQQQDPFnESSR (SEQ ID NO:6) | 2 | 1000.980713 | 2000.954149 | N11(HexNAc) | 3.454202652 |
| YBR078W | 4 | ANnITLRDVNSISF (SEQ ID NO:7) | 2 | 884.9568752 | 1768.906474 | N3(HexNAc) | 2.546951532 |
| | | GGANFDSSSSnFScNALK (SEQ ID NO:8) | 2 | 1034.447021 | 2067.886766 | N11(HexNAc), C14(Carbamidomethyl) | 3.940100193 |
| | | SIVSNDELSKAAFSnL (SEQ ID NO:9) | 2 | 950.4779052 | 1899.948534 | N15(HexNAc) | 2.71123457 |
| | | TVGGGFIIAnNTQLK (SEQ ID NO:10) | 2 | 869.471613 | 1737.935949 | N10(HexNAc) | 3.282219887 |
| YBR092C | 4 | GYMFEnQTSFPIFAASSER (SEQ ID NO:11) | 2 | 1194.045166 | 2387.083055 | N6(HexNAc) | 4.308128357 |
| | | SVGANLFnATL (SEQ ID NO:12) | 2 | 656.3403518 | 1311.673427 | N8(HexNAc) | 3.022809982 |
| | | TEKFQcSnDTYVRY (SEQ ID NO:13)¹ | 2 | 1008.454529 | 2015.901781 | C6(Carbamidomethyl), N8(HexNAc) | 3.974430799 |
| | | TTAGIIDDKnLTAEYVPFMGNTFHK (SEQ ID NO:14) | 3 | 1034.838867 | 3102.502048 | N11(HexNAc) | 3.836437225 |
| YBR093C | 3 | SVGSNLFnASVK (SEQ ID NO:15) | 2 | 714.3692646 | 1427.731253 | N8(HexNAc) | 2.479040861 |
| | | TEKFQcSnDTYVRY (SEQ ID NO:13)² | 2 | 1008.454529 | 2015.901781 | C6(Carbamidomethyl), N8(HexNAc) | 3.974430799 |
| | | TTAGIIDDKnLTAE (SEQ ID NO:16)² | 2 | 890.9440848 | 1780.880893 | N11(HexNAc) | 3.05523634 |
| YBR139W | 1 | DIRGPcEDnSTDGMcY (SEQ ID NO:17) | 2 | 1047.90686 | 2094.806444 | C6(Carbamidomethyl), N9(HexNAc), C15(Carbamidomethyl) | 4.591330051 |
| YBR162C | 1 | FVPGSTSncTF (SEQ ID NO:18) | 2 | 711.3149043 | 1421.622532 | N8(HexNAc), C9(Carbamidomethyl) | 3.159631968 |
| YBR171W | 1 | SnNGTFFETEEPIVETK (SEQ ID NO:19) | 2 | 1074.006958 | 2147.006639 | N2(HexNAc) | 3.961233854 |
| YBR229C | 2 | ISSFLSLSnSTADTFHL (SEQ ID NO:20) | 2 | 1023.008667 | 2045.010057 | N9(HexNAc) | 3.078636646 |
| | | NNLQHnITLK (SEQ ID NO:21) | 2 | 700.3782069 | 1399.749137 | N6(HexNAc) | 3.582325935 |

| Protein Accession | Glyco-sites | Sequence | Charge | m/z [Da] | MH+ [Da] | Modifications | XCorr |
|---|---|---|---|---|---|---|---|
| YBR286W | 7 | AHHLnYTLVPFDGR (SEQ ID NO:22) | 2 | 922.9670456 | 1844.926815 | N5(HexNAc) | 3.805802822 |
| | | AYnLTKEENSKIRVF (SEQ ID NO:23) | 2 | 1009.033264 | 2017.059252 | N3(HexNAc) | 3.133780718 |
| | | IISFnLSDAETGK (SEQ ID NO:24) | 2 | 800.4065885 | 1599.8059 | N5(HexNAc) | 3.350865602 |
| | | IKVDDLnATAW (SEQ ID NO:25) | 2 | 725.8727417 | 1450.738207 | N7(HexNAc) | 2.901429892 |
| | | IKVDDLnATAW (SEQ ID NO:25) | 2 | 725.8713101 | 1450.735344 | N7(HexNAc) | 2.780946016 |
| | | LAnYSTPDYGHPTR (SEQ ID NO:26) | 2 | 898.9245762 | 1796.841876 | N3(HexNAc) | 3.076839209 |
| | | LAnYSTPDYGHPTR (SEQ ID NO:26) | 2 | 898.9224243 | 1796.837572 | N3(HexNAc) | 3.403831482 |
| | | SFAnTTAFALSPPVDGFVGK (SEQ ID NO:27) | 2 | 1116.064288 | 2231.121299 | N4(HexNAc) | 3.524541616 |
| | | STPDYGHPTRVIGSKGHnKTmEY (SEQ ID NO:28) | 3 | 932.7775269 | 2796.318027 | N18(HexNAc), M21(Oxidation) | 2.75775218 |
| | | STPDYGHPTRVIGSKGHnKTMEY (SEQ ID NO:28) | 3 | 927.4489746 | 2780.332371 | N18(HexNAc) | 3.526721716 |
| | | APTYQELADTYAnATSDVLIAK (SEQ ID NO:29) | 2 | 1280.637451 | 2560.267626 | N13(HexNAc) | 5.310065746 |
| | | DLPAYLAnETFVTPVIVQSGK (SEQ ID NO:30) | 2 | 1234.154663 | 2467.30205 | N8(HexNAc) | 4.548676014 |
| | | DLPAYLAnETFVTPVIVQSGK (SEQ ID NO:30) | 2 | 1234.1521 | 2467.296923 | N8(HexNAc) | 4.494010448 |
| | | DLPAYLAnETFVTPVIVQSGK (SEQ ID NO:30) | 3 | 823.102417 | 2467.292698 | N8(HexNAc) | 5.077116013 |
| YCL043C | 3 | NSDVnNSIDYEGPR (SEQ ID NO:31) | 3 | 595.6020554 | 1784.791613 | N5(HexNAc) | 4.625511169 |
| | | NSDVnNSIDYEGPR (SEQ ID NO:31) | 2 | 892.8972778 | 1784.787279 | N5(HexNAc) | 3.915579796 |
| | | NSDVnNSIDYEGPR (SEQ ID NO:31) | 2 | 892.899353 | 1784.791429 | N5(HexNAc) | 3.436848879 |
| YCL045C | 2 | KLNPGKNTDVPIVANnHSSSHIF (SEQ ID NO:32) | 4 | 674.3503418 | 2694.379537 | N16(HexNAc) | 3.537136793 |
| | | TIDEIQLDSNDHNAMVcVnSSSNHWQK (SEQ ID NO:33) | 3 | 1116.500122 | 3347.485813 | C17(Carbamidomethyl), N19(HexNAc) | 4.378312111 |

| Protein Accession | Glyco-sites | Sequence | Charge | m/z [Da] | MH+ [Da] | Modifications | XCorr |
|---|---|---|---|---|---|---|---|
| YCR011C | 1 | VFSGnVTNEK (SEQ ID NO:34) | 2 | 730.3364854 | 1459.665694 | C5(Carbamidomethyl), N6(HexNAc) | 2.749768496 |
| YDL095W | 1 | NAPGESLTTFQnLTDGTK (SEQ ID NO:35) | 2 | 1050.008575 | 2099.009874 | N12(HexNAc) | 3.692959785 |
| YDR055W | 2 | ANnISLTDVHSVS (SEQ ID NO:36) | 2 | 781.3858597 | 1561.764443 | N3(HexNAc) | 2.771966696 |
| | | INNSISSLnFTKL (SEQ ID NO:37) | 2 | 828.4452113 | 1655.883146 | N9(HexNAc) | 2.657103777 |
| YDR434W | 1 | AIVFPSASSSPDGLAFInGTR (SEQ ID NO:38) | 2 | 1156.591553 | 2312.175829 | N18(HexNAc) | 5.184158325 |
| YEL001C | 2 | EMEVnGTSKF (SEQ ID NO:39) | 2 | 673.8093704 | 1346.611464 | N5(HexNAc) | 2.482161045 |
| | | GVnGTIVTYPHGYPVADITGA (SEQ ID NO:40) | 2 | 1154.077723 | 2307.14817 | N3(HexNAc) | 3.743284464 |
| YEL002C | 2 | LEYLDInSTSTTVDLYDKEQR (SEQ ID NO:41) | 3 | 903.442627 | 2708.313328 | N7(HexNAc) | 3.583855391 |
| | | LTLSPSGnDSETQYYTT (SEQ ID NO:42) | 2 | 1041.473633 | 2081.939989 | N8(HexNAc) | 4.13822031 |
| YEL040W | 1 | IWPGGnSTNAPGTIAW (SEQ ID NO:43) | 2 | 923.9529035 | 1846.89853 | N6(HexNAc) | 2.783670425 |
| YEL060C | 1 | NGGGQDLSAFWnDTKK (SEQ ID NO:44) | 2 | 971.958809 | 1942.910341 | N12(HexNAc) | 2.906452179 |
| YFR018C | 1 | TKEYNDLESNTVVSnSTLGVK (SEQ ID NO:45) | 3 | 835.0858239 | 2503.242918 | N15(HexNAc) | 3.168931961 |
| YGL022W | 1 | TTLVDNNTWnNTHIAIVGK (SEQ ID NO:46) | 2 | 1158.594727 | 2316.182176 | N10(HexNAc) | 3.993541241 |
| YGR014W | 1 | ELSNLITnSSSAFYTDGMGTAK (SEQ ID NO:47) | 3 | 838.0657205 | 2512.182608 | N8(HexNAc) | 3.784284353 |
| YGR189C | 2 | FHnYTLDWAMDK (SEQ ID NO:48) | 2 | 873.3936768 | 1745.780077 | N3(HexNAc) | 2.986134529 |
| | | SnTSSEGYPQSPM (SEQ ID NO:49) | 2 | 795.335144 | 1589.663011 | N2(HexNAc) | 3.276816607 |
| YGR282C | 1 | SYWQGQTMQnASY (SEQ ID NO:50) | 2 | 884.8778687 | 1768.748461 | N10(HexNAc) | 3.617331028 |
| YHR028C | 2 | NTPDYQEPNSnYTNDGK (SEQ ID NO:51) | 2 | 1081.46118 | 2161.915084 | N11(HexNAc) | 3.445133209 |
| | | TFIHNGQnLTVESITASPDLKR (SEQ ID NO:52) | 3 | 882.7964478 | 2646.37479 | N8(HexNAc) | 4.021240234 |

FIG. 10C

| Protein Accession | Glyco-sites | Sequence | Charge | m/z [Da] | MH+ [Da] | Modifications | XCorr |
|---|---|---|---|---|---|---|---|
| YHR101C | 1 | GnNTEDFQPFIDSEKR (SEQ ID NO:53) | 2 | 1051.485225 | 2101.963173 | N2(HexNAc) | 3.038024664 |
| YHR188C | 1 | SYASDIGAPLFnSTEK (SEQ ID NO:54) | 2 | 952.9617855 | 1904.916294 | N12(HexNAc) | 3.23469305 |
| YHR202W | 1 | SInMTDPVDAESPIFSR (SEQ ID NO:55) | 2 | 1042.494873 | 2083.982469 | N3(HexNAc) | 3.841515303 |
| YIL015W | 3 | AMTIQGLGAQnKSScEHETF (SEQ ID NO:56) | 2 | 1207.544556 | 2414.081835 | N11(HexNAc), C15(Carbamidomethyl) | 2.366041899 |
| | | AVQPTnDSMVLGDVFL (SEQ ID NO:57) | 2 | 955.9754161 | 1910.943556 | N6(HexNAc) | 4.752959251 |
| | | ISLAQANWnASEVSK (SEQ ID NO:58) | 2 | 911.9611816 | 1822.915087 | N9(HexNAc) | 3.773035765 |
| YJL002C | 2 | QLLAnSTTAPGDDGESEIR (SEQ ID NO:59) | 2 | 1090.020508 | 2179.033739 | N5(HexNAc) | 3.16720438 |
| | | TnVSIETQKSY (SEQ ID NO:60) | 2 | 737.8661912 | 1474.725106 | N2(HexNAc) | 2.802881241 |
| YJL171C | 8 | AFYTSPGFTVnNSR (SEQ ID NO:61) | 2 | 883.4255027 | 1765.843729 | N11(HexNAc) | 3.822407722 |
| | | AFYTSPGFTVnNSR (SEQ ID NO:61) | 2 | 883.4205359 | 1765.833795 | N11(HexNAc) | 3.106068134 |
| | | DIFEAMnGTEKNHLY (SEQ ID NO:62) | 2 | 993.956604 | 1986.905931 | N7(HexNAc) | 2.332874298 |
| | | EFEMPTETEKnSSSIGYY (SEQ ID NO:63) | 2 | 1159.006958 | 2317.006639 | N11(HexNAc) | 3.055534124 |
| | | GYITRnTTGTM (SEQ ID NO:64) | 2 | 710.3419101 | 1419.676544 | N6(HexNAc) | 2.736083746 |
| | | IIYSnVScPKSGY (SEQ ID NO:65) | 2 | 846.90979 | 1692.812303 | N5(HexNAc), C8(Carbamidomethyl) | 2.663366556 |
| | | KDITNnEScTcEVGDRVW (SEQ ID NO:66) | 2 | 1194.526491 | 2388.045705 | N6(HexNAc), C9(Carbamidomethyl), C11(Carbamidomethyl) | 3.084745169 |
| | | KDITNnEScTcEVGDRVW (SEQ ID NO:66) | 2 | 1194.525503 | 2388.043729 | N6(HexNAc), C9(Carbamidomethyl), C11(Carbamidomethyl) | 2.900859594 |
| | | QYPTNAncScW (SEQ ID NO:67) | 2 | 803.31814O8 | 1605.629005 | N7(HexNAc), C8(Carbamidomethyl), C10(Carbamidomethyl) | 4.050367832 |

FIG. 10D

| Protein Accession | Glyco-sites | Sequence | Charge | m/z [Da] | MH+ [Da] | Modifications | XCorr |
|---|---|---|---|---|---|---|---|
| | | TADnVTFLNHGGEASPcLGNAL (SEQ ID NO:68) | 2 | 1232.073486 | 2463.139696 | N4(HexNAc), C17(Carbamidomethyl) | 2.742713213 |
| | | TADnVTFLNHGGEASPcLGNAL (SEQ ID NO:68) | 2 | 1232.075073 | 2463.14287 | N4(HexNAc), C17(Carbamidomethyl) | 2.782211542 |
| YJL172W | 2 | AHQDVVPVNnETLSSWK (SEQ ID NO:69) | 2 | 1065.029241 | 2129.051205 | N10(HexNAc) | 3.776118755 |
| | | EFEAIEQLLIDGFKPnR (SEQ ID NO:70) | 3 | 742.0560303 | 2224.153538 | N16(HexNAc) | 3.662000656 |
| YJL192C | 1 | GRLDLAASnITGFVSTR (SEQ ID NO:71) | 2 | 992.0255539 | 1983.043831 | N9(HexNAc) | 4.364808083 |
| YKL039W | 1 | TSTnRSLANPIMT (SEQ ID NO:72) | 2 | 805.902832 | 1610.798387 | N4(HexNAc) | 2.287690401 |
| YKL046C | 2 | VYDGVSIDDncTKVTSY (SEQ ID NO:73) | 2 | 1070.984009 | 2140.960741 | N10(HexNAc), C11(Carbamidomethyl) | 3.320672274 |
| | | YTGnQTYVDWAEK (SEQ ID NO:74) | 2 | 890.4065117 | 1779.805747 | N4(HexNAc) | 2.776555777 |
| YLR066W | 1 | TYGETVGnYTLTVENK (SEQ ID NO:75) | 2 | 997.4805298 | 1993.953783 | N8(HexNAc) | 3.020689964 |
| | | MWNQQnNTIMK (SEQ ID NO:76) | 2 | 806.8742012 | 1612.741126 | N6(HexNAc) | 2.745708227 |
| YLR084C | 3 | nSSLYADIYDNK (SEQ ID NO:77) | 2 | 804.3743993 | 1607.741522 | N1(HexNAc) | 2.650716066 |
| | | TDPSSSIMnLTYLDPLSGELK (SEQ ID NO:78) | 2 | 1243.612797 | 2486.218318 | N9(HexNAc) | 3.372883797 |
| YLR413W | 2 | LVDSTNPIGTTESLITLNnMTTEEK (SEQ ID NO:79) | 3 | 976.1559448 | 2926.453281 | N19(HexNAc) | 4.035261631 |
| | | STMlAEnITQSSSAK (SEQ ID NO:80) | 2 | 886.9328003 | 1772.858324 | N7(HexNAc) | 3.849070072 |
| YLR450W | 1 | IPTELVSEnGTK (SEQ ID NO:81) | 2 | 746.8902367 | 1492.773197 | N9(HexNAc) | 2.896726847 |
| YML052W | 1 | FYWVQGnTTGIPNAGDETR (SEQ ID NO:82) | 2 | 1166.046199 | 2331.085122 | N7(HexNAc) | 2.482077122 |
| YML130C | 2 | NDHVSPScnVTFN (SEQ ID NO:83) | 2 | 848.3660173 | 1695.724758 | C8(Carbamidomethyl), N9(HexNAc) | 3.328930855 |
| | | TnNSQSHVFDDLK (SEQ ID NO:84) | 2 | 855.4012451 | 1709.795214 | N2(HexNAc) | 3.83287549 |
| | | nLTDLEYIPPLVVYIPNTK (SEQ ID NO:85) | 2 | 1204.154053 | 2407.300829 | N1(HexNAc) | 2.349189281 |

| Protein Accession | Glyco-sites | Sequence | Charge | m/z [Da] | MH+ [Da] | Modifications | XCorr |
|---|---|---|---|---|---|---|---|
| YMR006C | 3 | SIVNPGGSnLTYTIER (SEQ ID NO:86) | 2 | 963.4951652 | 1925.983054 | N9(HexNAc) | 3.731044054 |
| | | SRATSnFSDTSLL (SEQ ID NO:87) | 2 | 802.3920999 | 1603.776923 | N6(HexNAc) | 2.326139927 |
| | | AMLSGAGmLAAMDnR (SEQ ID NO:88) | 2 | 865.3982764 | 1729.789276 | M8(Oxidation), N14(HexNAc) | 3.684348345 |
| | | GnFTDDSDFLGcVGcAIIR (SEQ ID NO:89) | 2 | 1161.517955 | 2322.028633 | N2(HexNAc), C12(Carbamidomethyl), C15(Carbamidomethyl) | 4.330984116 |
| YMR008C | 6 | IPNSRHSFNGnQSTF (SEQ ID NO:90) | 2 | 955.9507446 | 1910.894213 | N11(HexNAc) | 2.324790716 |
| | | LQKnATSSIIESEY (SEQ ID NO:91) | 2 | 894.4474681 | 1787.88766 | N4(HexNAc) | 3.077707291 |
| | | NRATSnFSDTSLL (SEQ ID NO:92) | 2 | 815.8987427 | 1630.790209 | N6(HexNAc) | 2.538153648 |
| | | TSVQAIVDnTTESNSIW (SEQ ID NO:93) | 2 | 1035.494751 | 2069.982225 | N9(HexNAc) | 2.919584274 |
| | | EIDGITTEKnVTDMLY (SEQ ID NO:94) | 2 | 1023.992371 | 2046.977465 | N10(HexNAc) | 3.145750284 |
| | | FDDTMLDVIPSDLQLnAT (SEQ ID NO:95) | 2 | 1107.030517 | 2213.053758 | N16(HexNAc) | 2.855551004 |
| YMR058W | 5 | NGVNYAFFNnITYTAPK (SEQ ID NO:96) | 2 | 1070.022461 | 2139.037645 | N10(HexNAc) | 5.408295631 |
| | | SSGDQAnNSEIYGSNTHTF (SEQ ID NO:97) | 2 | 1117.476859 | 2233.946442 | N7(HexNAc) | 3.779998541 |
| | | TVLVHTKnDTDKNF (SEQ ID NO:98) | 2 | 918.9721757 | 1836.937075 | N8(HexNAc) | 2.694506884 |
| YMR200W | 1 | SRYnQTETFKEY (SEQ ID NO:99) | 2 | 885.9120483 | 1770.81682 | N4(HexNAc) | 2.439655496 |
| YMR238W | 1 | DGAEIDTncTDITK (SEQ ID NO:100) | 2 | 879.3910413 | 1757.774806 | N8(HexNAc), C9(Carbamidomethyl) | 3.369255543 |
| YMR297W | 2 | ILGIDPnVTQY (SEQ ID NO:101) | 2 | 719.3773636 | 1437.747451 | N7(HexNAc) | 2.826209068 |
| | | VRnWTASITDEVAGEVK (SEQ ID NO:102) | 2 | 1040.532104 | 2080.056932 | N3(HexNAc) | 4.878105164 |
| | | AGNEVTNnYTNTDASAF (SEQ ID NO:103) | 2 | 997.4321289 | 1993.856981 | N8(HexNAc) | 2.951339483 |

FIG. 10G

| Protein Accession | Glyco-sites | Sequence | Charge | m/z [Da] | MH+ [Da] | Modifications | XCorr |
|---|---|---|---|---|---|---|---|
| | | AlnTTLDHSEcm (SEQ ID NO:104) | 2 | 806.8440162 | 1612.680756 | N3(HexNAc), C11(Carbamidomethyl), M12(Oxidation) | 3.304506302 |
| | | AlnTTLDHSEcM (SEQ ID NO:104) | 2 | 798.8465366 | 1596.685797 | N3(HexNAc), C11(Carbamidomethyl) | 3.309619427 |
| | | FFYSNnGSQFY (SEQ ID NO:105) | 2 | 789.8396229 | 1578.671969 | N6(HexNAc) | 3.164842367 |
| | | FFYSNnGSQFY (SEQ ID NO:105) | 2 | 789.8414596 | 1578.675643 | N6(HexNAc) | 3.558385611 |
| | | FNWIcNEVDcSGISAnGTAGK (SEQ ID NO:106) | 2 | 1253.055054 | 2505.102831 | C5(Carbamidomethyl), C10(Carbamidomethyl), N16(HexNAc) | 5.218724251 |
| | | FNWIcNEVDcSGISAnGTAGK (SEQ ID NO:106) | 2 | 1253.055176 | 2505.103075 | C5(Carbamidomethyl), C10(Carbamidomethyl), N16(HexNAc) | 3.625688553 |
| YMR307W | 7 | GVAYQADTAnETSGSTVNDPLANYEScSR (SEQ ID NO:107) | 3 | 1094.817993 | 3282.439426 | N10(HexNAc), C27(Carbamidomethyl) | 7.549865246 |
| | | GVAYQADTAnETSGSTVNDPLANYEScSR (SEQ ID NO:107) | 3 | 1094.814768 | 3282.42975 | N10(HexNAc), C27(Carbamidomethyl) | 5.654808521 |
| | | KTVVDTFAnYTNV (SEQ ID NO:108) | 2 | 838.9219971 | 1676.836718 | N9(HexNAc) | 3.207078218 |
| | | nLSIPVFFSEYGcNEVTPR (SEQ ID NO:109) | 2 | 1217.584159 | 2434.161042 | N1(HexNAc), C13(Carbamidomethyl) | 3.19590497 |
| | | ANGTnSTTNTTTAESSQL (SEQ ID NO:4)³ | 2 | 1001.957005 | 2002.906734 | N5(HexNAc) | 5.235136509 |
| | | EYSnFTTPYGL (SEQ ID NO:110) | 2 | 748.8440787 | 1496.680881 | N4(HexNAc) | 2.606115341 |
| | | EYSnFTTPYGL (SEQ ID NO:110) | 2 | 748.8403931 | 1496.67351 | N4(HexNAc) | 2.30634737 |
| | | GGQVPITnSSLTHTNY (SEQ ID NO:111) | 2 | 947.4632453 | 1893.919214 | N8(HexNAc) | 2.878471375 |
| | | NSSSALnITELY (SEQ ID NO:1) | 2 | 758.87716312 | 1516.735986 | N7(HexNAc) | 2.914322853 |
| | | NSSSALnITELY (SEQ ID NO:1) | 2 | 758.8693237 | 1516.731371 | N7(HexNAc) | 2.602772951 |

FIG. 10H

| Protein Accession | Glyco-sites | Sequence | Charge | m/z [Da] | MH+ [Da] | Modifications | XCorr |
|---|---|---|---|---|---|---|---|
| YNL160W | 9 | NVARVVnETIQDK (SEQ ID NO:112) | 2 | 845.9514515 | 1690.895526 | N7(HexNAc) | 3.666853189 |
| | | NVARVVnETIQDK (SEQ ID NO:112) | 2 | 845.9513803 | 1690.895484 | N7(HexNAc) | 3.654164076 |
| | | QIIVTGGQVPITNSSLTHTnY (SEQ ID NO:113) | 2 | 1224.634155 | 2448.261034 | N20(HexNAc) | 3.167713642 |
| | | QIIVTGGQVPITnSSLTHTnYTR (SEQ ID NO:2)⁴ | 3 | 970.8408203 | 2910.507908 | N13(HexNAc), N20(HexNAc) | 3.268575907 |
| | | SGSTnSTSSTIESTEIPVVY (SEQ ID NO:114) | 2 | 1132.5382 | 2264.069123 | N5(HexNAc) | 4.173271656 |
| | | SIIFDTEKPIVVTEDSAYAIPVANNKnATKRGVL (SEQ ID NO:115) | 4 | 970.5256958 | 3879.080953 | N27(HexNAc) | 4.694067001 |
| | | TRLFnSSSAL (SEQ ID NO:116) | 2 | 650.8391113 | 1300.670946 | N5(HexNAc) | 2.958168507 |
| YNL327W | 2 | STNnFTISIPEK (SEQ ID NO:117) | 2 | 778.3939209 | 1555.780565 | N4(HexNAc) | 2.505096436 |
| | | VAKnTSAITTDGGIY (SEQ ID NO:118) | 2 | 858.4379498 | 1715.868623 | N4(HexNAc) | 3.236876011 |
| YNR067C | 1 | LnGTWAADNKDWVNSL (SEQ ID NO:119) | 2 | 1004.982178 | 2008.957079 | N2(HexNAc) | 2.729263544 |
| YOL011W | 3 | ATAnFSDSSEVLSK (SEQ ID NO:120) | 2 | 830.8972778 | 1660.787279 | N4(HexNAc) | 2.301896572 |
| | | EATSISQnESAWLEK (SEQ ID NO:121) | 2 | 949.4552001 | 1897.903123 | N8(HexNAc) | 2.360936165 |
| | | NnFTDDPEFMGcVGcAIIR (SEQ ID NO:122) | 2 | 1211.031734 | 2421.056191 | N2(HexNAc), C12(Carbamidomethyl), C15(Carbamidomethyl) | 4.539266586 |
| YOL030W | 5 | AGNEVINSVnTTNTATY (SEQ ID NO:123) | 2 | 987.4662844 | 1973.925292 | N10(HexNAc) | 4.00425148 |
| | | ASSSnSSTPSIEIK (SEQ ID NO:124) | 2 | 806.8974416 | 1612.787607 | N5(HexNAc) | 2.666911364 |
| | | GVDYQPGGSSnLTDPLADASVcDR (SEQ ID NO:125) | 3 | 900.4059448 | 2699.203281 | N11(HexNAc), C22(Carbamidomethyl) | 4.426597595 |
| | | GVDYQPGGSSnLTDPLADASVcDR (SEQ ID NO:125) | 2 | 1350.108643 | 2699.210009 | N11(HexNAc), C22(Carbamidomethyl) | 4.391893387 |
| | | SGGLVYEYSnETNNYGLVQIDGDKVTK (SEQ ID NO:126) | 3 | 1056.846436 | 3168.524753 | N10(HexNAc) | 4.91785574 |

| Protein Accession | Glyco-sites | Sequence | Charge | m/z [Da] | MH+ [Da] | Modifications | XCorr |
|---|---|---|---|---|---|---|---|
| YOL154W | 3 | SKVSNPEGNGGYSTSNnY (SEQ ID NO:127) | 2 | 1040.457533 | 2079.907789 | N17(HexNAc) | 3.68306613 |
| | | DTnSTAELQSPSSQEILGW (SEQ ID NO:128) | 2 | 1134.531982 | 2268.056688 | N3(HexNAc) | 3.832524061 |
| | | EEVVDYTQNnATYAVR (SEQ ID NO:129) | 2 | 1038.98938 | 2076.971483 | N10(HexNAc) | 4.019247055 |
| | | GWSHATFPTIYQTcnETNAR (SEQ ID NO:130) | 2 | 1280.081055 | 2559.154833 | C14(Carbamidomethyl), N15(HexNAc) | 3.681435585 |
| YOR320C | 1 | TLDNDGNDIPVGLnDSVAYSK (SEQ ID NO:131) | 2 | 1206.57459 | 2412.141904 | N14(HexNAc) | 4.254417347 |
| YPL123C | 1 | GIEPNcPINIPLScSnK (SEQ ID NO:132) | 2 | 1059.510132 | 2118.012987 | C6(Carbamidomethyl), C14(Carbamidomethyl), N16(HexNAc) | 2.826607704 |
| YPL154C | 2 | AnGTEFAIQY (SEQ ID NO:133) | 2 | 659.8118028 | 1318.616329 | N2(HexNAc) | 3.035950661 |
| | | NGYnFTIGPY (SEQ ID NO:134) | 2 | 675.8127564 | 1350.618236 | N4(HexNAc) | 2.576419353 |

FIG. 10I

| Sequence | Confidence | ΔM [ppm] | Ions Matched | RT [min] | Activation Type | Sample |
|---|---|---|---|---|---|---|
| NQDGSSKPnFTVE (SEQ ID NO:5) | < 5% FDR | 2.805611115 | 13/24 | 54.88398667 | CID | log-phase lysate, trypsinized, IW=4 |
| SILFQQQDPFnESSR (SEQ ID NO:6) | < 1% FDR | 3.512255017 | 13/28 | 97.86845167 | CID | log-phase lysate, trypsinized, IW=4 |
| ANnITLRDVNSISF (SEQ ID NO:7) | < 5% FDR | 4.388320089 | 10/26 | 102.367955 | CID | stationary-phase lysate, chymotrypsinized, IW=4 |
| GGANFDSSSSnFScNALK (SEQ ID NO:8) | < 1% FDR | 1.557652383 | 16/34 | 73.08974667 | CID | log-phase lysate, trypsinized, IW=4 |
| SIVSNDELSKAAFSnL (SEQ ID NO:9) | < 5% FDR | 1.475033624 | 16/30 | 101.6733683 | CID | stationary-phase lysate, chymotrypsinized, IW=2 |
| TVGGGFIIAnNTQLK (SEQ ID NO:10) | < 1% FDR | 3.831009111 | 14/28 | 85.63262667 | CID | log-phase lysate, trypsinized, IW=4 |
| GYMFEnQTSFPIFAASSER (SEQ ID NO:11) | < 1% FDR | 2.46497969 | 17/36 | 121.0859533 | CID | log-phase lysate, trypsinized, IW=4 |
| SVGANLFnATL (SEQ ID NO:12) | < 1% FDR | 2.459156712 | 15/20 | 111.6336133 | CID | stationary-phase lysate, chymotrypsinized, IW=2 |
| TEKFQcSnDTYYRY (SEQ ID NO:13)¹ | < 1% FDR | 4.546698294 | 15/26 | 63.80685 | CID | stationary-phase lysate, chymotrypsinized, IW=4 |
| TTAGIIDDKNnLTAEYVPFMGNTFHK (SEQ ID NO:14) | < 1% FDR | 0.646901265 | 26/100 | 109.7747217 | CID | stationary-phase lysate, chymotrypsinized, IW=2 |
| SVGSNLFnASVK (SEQ ID NO:15) | < 5% FDR | 1.730915739 | 17/22 | 75.29615833 | CID | stationary-phase lysate, trypsinized, IW=2 |
| TEKFQcSnDTYYRY (SEQ ID NO:13)² | < 1% FDR | 4.546698294 | 15/26 | 63.80685 | CID | stationary-phase lysate, chymotrypsinized, IW=4 |
| TTAGIIDDKNnLTAE (SEQ ID NO:16)² | < 5% FDR | 4.863734113 | 16/28 | 67.42167 | CID | stationary-phase lysate, chymotrypsinized, IW=4 |
| DIRGPcEDnSTDGMcY (SEQ ID NO:17) | < 1% FDR | 4.957395064 | 19/30 | 70.58775667 | CID | log-phase lysate, chymotrypsinized, IW=4 |
| FVPGSTSncTF (SEQ ID NO:18) | < 1% FDR | 4.281472127 | 15/20 | 75.99891167 | CID | stationary-phase lysate, chymotrypsinized, IW=4 |
| SnNGTFFETEEPIVETK (SEQ ID NO:19) | < 1% FDR | 5.974874688 | 18/32 | 92.17223 | CID | stationary-phase lysate, chymotrypsinized, IW=4 |
| ISSFLSLSnSTADTFHL (SEQ ID NO:20) | < 1% FDR | 5.660639337 | 15/32 | 131.51916 | CID | stationary-phase lysate, trypsinized, IW=4 |
| NNLQHnITLK (SEQ ID NO:21) | < 1% FDR | 2.897568715 | 15/18 | 48.82865167 | CID | log-phase lysate, trypsinized, IW=4 |

FIG. 10J

| Sequence | Confidence | ΔM [ppm] | Ions Matched | RT [min] | Activation Type | Sample |
|---|---|---|---|---|---|---|
| AHHLnYTLVPFDGR (SEQ ID NO:22) | < 1% FDR | 3.638790737 | 16/26 | 78.424425 | CID | log-phase lysate, trypsinized, IW=4 |
| AYnLTKEENSKIRVF (SEQ ID NO:23) | < 1% FDR | 3.996114792 | 14/28 | 74.24174333 | CID | log-phase lysate, chymotrypsinized, IW=2 |
| IISFnLSDAETGK (SEQ ID NO:24) | < 1% FDR | 2.218389765 | 17/24 | 93.36925833 | CID | log-phase lysate, trypsinized, IW=4 |
| IKVDDLnATAW (SEQ ID NO:25) | < 5% FDR | 3.215934078 | 13/20 | 93.86807167 | CID | log-phase lysate, trypsinized, IW=4 |
| IKVDDLnATAW (SEQ ID NO:25) | < 5% FDR | 1.242336639 | 17/20 | 92.12438667 | CID | log-phase lysate, trypsinized, IW=2 |
| LAnYSTPDYGHPTR (SEQ ID NO:26) | < 1% FDR | 3.224827126 | 14/26 | 53.49511333 | CID | log-phase lysate, trypsinized, IW=4 |
| LAnYSTPDYGHPTR (SEQ ID NO:26) | < 1% FDR | 0.829631368 | 14/26 | 52.324095 | CID | log-phase lysate, trypsinized, IW=2 |
| SFAnTTAFALSPPVDGFVGK (SEQ ID NO:27) | < 1% FDR | 3.17227136 | 16/38 | 119.6352633 | CID | log-phase lysate, trypsinized, IW=4 |
| STPDYGHPTRVIGSKGHnKTmEY (SEQ ID NO:28) | < 5% FDR | 0.4044663 | 21/88 | 46.29782667 | CID | log-phase lysate, chymotrypsinized, IW=2 |
| STPDYGHPTRVIGSKGHnKTMEY (SEQ ID NO:28) | < 5% FDR | 3.736703653 | 26/88 | 53.28489667 | CID | stationary-phase lysate, chymotrypsinized, IW=4 |
| APTYQELADTYAnATSDVLIAK (SEQ ID NO:29) | < 1% FDR | 3.903663683 | 20/42 | 123.8389183 | CID | log-phase lysate, trypsinized, IW=4 |
| DLPAYLAnETFVTPVIVQSGK (SEQ ID NO:30) | < 1% FDR | 5.766724783 | 20/40 | 124.1801833 | CID | log-phase lysate, trypsinized, IW=4 |
| DLPAYLAnETFVTPVIVQSGK (SEQ ID NO:30) | < 1% FDR | 3.688773194 | 20/40 | 123.26376 | CID | log-phase lysate, trypsinized, IW=2 |
| DLPAYLAnETFVTPVIVQSGK (SEQ ID NO:30) | < 5% FDR | 1.976428077 | 36/80 | 123.8779633 | CID | stationary-phase lysate, trypsinized, IW=2 |
| NSDVnNSIDYEGPR (SEQ ID NO:31) | < 1% FDR | 4.007055106 | 33/52 | 58.88194667 | CID | log-phase lysate, trypsinized, IW=4 |
| NSDVnNSIDYEGPR (SEQ ID NO:31) | < 1% FDR | 1.578756245 | 18/26 | 56.426475 | CID | log-phase lysate, trypsinized, IW=2 |
| NSDVnNSIDYEGPR (SEQ ID NO:31) | < 1% FDR | 3.9041731 | 19/26 | 57.156645 | CID | stationary-phase lysate, trypsinized, IW=2 |
| KLNPGKNTDVPIVAnNhHSSSHIF (SEQ ID NO:32) | < 5% FDR | 1.408861464 | 33/132 | 68.70797333 | CID | log-phase lysate, chymotrypsinized, IW=2 |
| TIDEIQLDSNDHNAMVcVnSSSNHWQK (SEQ ID NO:33) | < 1% FDR | 1.286834711 | 28/104 | 84.655555 | CID | log-phase lysate, trypsinized, IW=4 |

FIG. 10K

| Sequence | Confidence | ΔM [ppm] | Ions Matched | RT [min] | Activation Type | Sample |
|---|---|---|---|---|---|---|
| VFSGcnVTNEK (SEQ ID NO:34) | < 5% FDR | 0.841882848 | 17/20 | 46.93232833 | CID | log-phase lysate, trypsinized, IW=4 |
| NAPGESLTTFQnLTDGTK (SEQ ID NO:35) | < 1% FDR | 2.302299058 | 18/34 | 88.44216333 | CID | log-phase lysate, trypsinized, IW=2 |
| ANnlSLTDVHSVS (SEQ ID NO:36) | < 5% FDR | 1.864262263 | 15/24 | 68.42515 | CID | stationary-phase lysate, chymotrypsinized, IW=2 |
| INNSISSLnFTKL (SEQ ID NO:37) | < 5% FDR | 4.212112346 | 14/24 | 107.4223517 | CID | stationary-phase lysate, chymotrypsinized, IW=4 |
| AIVFPSASSSPDGLAFInGTR (SEQ ID NO:38) | < 1% FDR | 3.36373586 | 20/40 | 115.5085017 | CID | log-phase lysate, trypsinized, IW=4 |
| EMEVnGTSKF (SEQ ID NO:39) | < 5% FDR | 4.383530654 | 15/18 | 59.74507833 | CID | stationary-phase lysate, chymotrypsinized, IW=2 |
| GVnGTIVTYPHGYPVADITGA (SEQ ID NO:40) | < 1% FDR | 2.90332701 | 18/40 | 101.0947867 | CID | log-phase lysate, trypsinized, IW=4 |
| LEYLDInSTSTTVDLYDKEQR (SEQ ID NO:41) | < 1% FDR | 2.694041824 | 26/80 | 99.68225667 | CID | log-phase lysate, trypsinized, IW=4 |
| LTLSPSGnDSETQYYTT (SEQ ID NO:42) | < 1% FDR | 4.398640234 | 19/32 | 83.36069667 | CID | stationary-phase lysate, chymotrypsinized, IW=4 |
| IWPGGnSTNAPGTIAW (SEQ ID NO:43) | < 5% FDR | 5.614313302 | 11/30 | 116.8968683 | CID | stationary-phase lysate, chymotrypsinized, IW=2 |
| NGGGQDLSAFWnDTKK (SEQ ID NO:44) | < 5% FDR | 2.609551015 | 12/30 | 83.10665167 | CID | log-phase lysate, trypsinized, IW=4 |
| TKEYNDLESNTVVSnSTLGVK (SEQ ID NO:45) | < 5% FDR | 4.305219519 | 28/80 | 75.47155667 | CID | log-phase lysate, trypsinized, IW=4 |
| TTLVDNNTWnNTHIAIVGK (SEQ ID NO:46) | < 1% FDR | 3.456206978 | 16/36 | 90.662645 | CID | log-phase lysate, trypsinized, IW=4 |
| ELSNLITnSSSAFYTDGMGTAK (SEQ ID NO:47) | < 1% FDR | 6.168774387 | 29/84 | 108.5731933 | CID | stationary-phase lysate, chymotrypsinized, IW=4 |
| FHnYTLDWAMDK (SEQ ID NO:48) | < 1% FDR | 2.861526312 | 17/22 | 88.66592667 | CID | stationary-phase lysate, chymotrypsinized, IW=2 |
| SnTSSEGYPQSPM (SEQ ID NO:49) | < 1% FDR | 5.240208697 | 16/24 | 59.94088167 | CID | stationary-phase lysate, chymotrypsinized, IW=4 |
| SYWQGQTMQnASY (SEQ ID NO:50) | < 1% FDR | 5.121918062 | 18/24 | 82.17731667 | CID | stationary-phase lysate, chymotrypsinized, IW=4 |
| NTPDYQEPNSnYTNDGK (SEQ ID NO:51) | < 1% FDR | 3.854354509 | 15/32 | 48.98603333 | CID | log-phase lysate, trypsinized, IW=2 |
| TFIHNGQnLTVESITASPDLKR (SEQ ID NO:52) | < 1% FDR | 3.884072565 | 25/84 | 85.578675 | CID | log-phase lysate, trypsinized, IW=2 |

FIG. 10L

| Sequence | Confidence | ΔM [ppm] | Ions Matched | RT [min] | Activation Type | Sample |
|---|---|---|---|---|---|---|
| GnNTEDFQPFIDSEKR (SEQ ID NO:53) | < 1% FDR | 2.2558345 | 11/30 | 77.87087167 | CID | log-phase lysate, trypsinized, IW=4 |
| SYASDIGAPLFnSTEK (SEQ ID NO:54) | < 1% FDR | 6.70536151 | 15/30 | 94.89993333 | CID | stationary-phase lysate, chymotrypsinized, IW=4 |
| SInMTDPVDAESPIFSR (SEQ ID NO:55) | < 1% FDR | 2.911816121 | 18/32 | 104.2068033 | CID | log-phase lysate, trypsinized, IW=4 |
| AMTIQGLGAQnKSScEHETF (SEQ ID NO:56) | < 5% FDR | -2.315825336 | 14/38 | 76.752915 | CID | stationary-phase lysate, chymotrypsinized, IW=2 |
| AVQPTnDSMVLGDVFL (SEQ ID NO:57) | < 1% FDR | 5.659112525 | 22/30 | 135.3546117 | CID | stationary-phase lysate, chymotrypsinized, IW=4 |
| ISLAQANWnASEVSK (SEQ ID NO:58) | < 1% FDR | 3.184658074 | 18/28 | 82.76129833 | CID | stationary-phase lysate, trypsinized, IW=2 |
| QLLAnSTTAPGDDGESEIR (SEQ ID NO:59) | < 1% FDR | 2.977331137 | 16/36 | 67.31339167 | CID | stationary-phase lysate, trypsinized, IW=2 |
| TnVSIETQKSY (SEQ ID NO:60) | < 1% FDR | 4.648021719 | 14/20 | 53.35557167 | CID | log-phase lysate, chymotrypsinized, IW=4 |
| AFYTSPGFTVnNSR (SEQ ID NO:61) | < 1% FDR | 7.615378806 | 14/26 | 79.641185 | CID | stationary-phase lysate, trypsinized, IW=4 |
| AFYTSPGFTVnNSR (SEQ ID NO:61) | < 1% FDR | 1.989909443 | 15/26 | 78.85282167 | CID | log-phase lysate, trypsinized, IW=2 |
| DIFEAMnGTEKNHLY (SEQ ID NO:62) | < 5% FDR | 1.736412257 | 13/28 | 94.86473333 | CID | stationary-phase lysate, chymotrypsinized, IW=2 |
| EFEMPTETEKnSSSIGYY (SEQ ID NO:63) | < 1% FDR | 3.918027454 | 14/34 | 93.88722833 | CID | stationary-phase lysate, chymotrypsinized, IW=2 |
| GYITRnTTGTM (SEQ ID NO:64) | < 5% FDR | 4.932358482 | 17/20 | 51.534865 | CID | stationary-phase lysate, chymotrypsinized, IW=4 |
| IIYSnVScPKSGY (SEQ ID NO:65) | < 5% FDR | 3.708714848 | 12/24 | 63.33836 | CID | stationary-phase lysate, chymotrypsinized, IW=2 |
| KDITNnEScTcEVGDRVW (SEQ ID NO:66) | < 5% FDR | 4.319815275 | 18/34 | 71.557535 | CID | stationary-phase lysate, chymotrypsinized, IW=4 |
| KDITNnEScTcEVGDRVW (SEQ ID NO:66) | < 1% FDR | 3.49241577 | 15/34 | 69.567555 | CID | stationary-phase lysate, chymotrypsinized, IW=2 |
| QYPTNAncScW (SEQ ID NO:67) | < 1% FDR | 4.406821612 | 14/20 | 71.02741167 | CID | stationary-phase lysate, chymotrypsinized, IW=4 |

FIG. 10M

| Sequence | Confidence | ΔM [ppm] | Ions Matched | RT [min] | Activation Type | Sample |
|---|---|---|---|---|---|---|
| TADnVTFLNHGGEASPcLGNAL (SEQ ID NO:68) | < 5% FDR | 1.165478456 | 12/42 | 100.1322933 | CID | log-phase lysate, trypsinized, IW=2 |
| TADnVTFLNHGGEASPcLGNAL (SEQ ID NO:68) | < 1% FDR | 2.45400478 | 15/42 | 100.79439 | CID | stationary-phase lysate, trypsinized, IW=2 |
| AHQDVVPVNnETLSSWK (SEQ ID NO:69) | < 1% FDR | 4.280577729 | 22/32 | 80.436325 | CID | log-phase lysate, trypsinized, IW=4 |
| EFEAIEQLLIDGFKPnR (SEQ ID NO:70) | < 1% FDR | 5.739833198 | 21/64 | 144.8828883 | CID | log-phase lysate, trypsinized, IW=4 |
| GRLDLAASnITGFVSTR (SEQ ID NO:71) | < 5% FDR | 1.069046335 | 22/32 | 97.59790833 | CID | log-phase lysate, trypsinized, IW=2 |
| TSTnRSLANPIMT (SEQ ID NO:72) | < 1% FDR | 1.139895914 | 13/24 | 65.62128833 | CID | stationary-phase lysate, chymotrypsinized, IW=2 |
| VYDGVSIDDncTKVTSY (SEQ ID NO:73) | < 1% FDR | 4.920995478 | 11/32 | 81.05946 | CID | log-phase lysate, chymotrypsinized, IW=4 |
| YTGnQTYVDWAEK (SEQ ID NO:74) | < 5% FDR | 4.183288515 | 12/24 | 74.32601667 | CID | log-phase lysate, trypsinized, IW=4 |
| TYGETVGnYTLTVENK (SEQ ID NO:75) | < 1% FDR | 1.304769616 | 15/30 | 81.08692667 | CID | log-phase lysate, trypsinized, IW=4 |
| MWNQQnNTIMK (SEQ ID NO:76) | < 1% FDR | 2.600861056 | 14/20 | 63.1965 | CID | stationary-phase lysate, trypsinized, IW=2 |
| nSSLYADIYDNK (SEQ ID NO:77) | < 5% FDR | 4.285932919 | 17/22 | 77.22236167 | CID | stationary-phase lysate, trypsinized, IW=2 |
| TDPSSSIMnLTYLDPLSGELK (SEQ ID NO:78) | < 1% FDR | 2.138286455 | 16/40 | 137.96975 | CID | log-phase lysate, trypsinized, IW=2 |
| LVDSTNPIGTTESLITLNnMTTEEK (SEQ ID NO:79) | < 1% FDR | 5.870561053 | 29/96 | 120.6553 | CID | log-phase lysate, trypsinized, IW=4 |
| STMIAEnITQSSSAK (SEQ ID NO:80) | < 1% FDR | 5.044207885 | 18/28 | 61.40516 | CID | log-phase lysate, trypsinized, IW=4 |
| IPTELVSEnGTK (SEQ ID NO:81) | < 5% FDR | 5.336088863 | 14/22 | 60.43576 | CID | log-phase lysate, trypsinized, IW=4 |
| FYWVQGnTTGIPNAGDETR (SEQ ID NO:82) | < 5% FDR | 2.222249199 | 16/36 | 94.16915167 | CID | stationary-phase lysate, trypsinized, IW=2 |
| NDHVSPScnVTFN (SEQ ID NO:83) | < 1% FDR | 3.386605123 | 14/24 | 58.113155 | CID | log-phase lysate, trypsinized, IW=2 |
| TnNSQSHVFDDLK (SEQ ID NO:84) | < 1% FDR | 3.744491927 | 18/24 | 59.02442667 | CID | log-phase lysate, trypsinized, IW=4 |
| nLTDLEYIPPLVVYIPNTK (SEQ ID NO:85) | < 5% FDR | 3.741762825 | 15/36 | 141.7003083 | CID | stationary-phase lysate, trypsinized, IW=2 |

FIG. 10N

| Sequence | Confidence | ΔM [ppm] | Ions Matched | RT [min] | Activation Type | Sample |
|---|---|---|---|---|---|---|
| SIVNPGGSnLTYTIER (SEQ ID NO:86) | < 1% FDR | 5.427124772 | 19/30 | 84.69649833 | CID | stationary-phase lysate, trypsinized, IW=2 |
| SRATSnFSDTSLL (SEQ ID NO:87) | < 5% FDR | 3.006524938 | 11/24 | 80.35051167 | CID | stationary-phase lysate, chymotrypsinized, IW=2 |
| AMLSGAGmLAAMDnR (SEQ ID NO:88) | < 1% FDR | 3.659372127 | 15/28 | 80.95484167 | CID | stationary-phase lysate, trypsinized, IW=2 |
| GnFTDDSDFLGcVGcAllR (SEQ ID NO:89) | < 1% FDR | -0.097272391 | 21/36 | 125.6013717 | CID | stationary-phase lysate, chymotrypsinized, IW=2 |
| IPNSRHSFNGnQSTF (SEQ ID NO:90) | < 5% FDR | 2.067795164 | 12/28 | 53.16062833 | CID | log-phase lysate, chymotrypsinized, IW=2 |
| LQknATSSIIESEY (SEQ ID NO:91) | < 1% FDR | 3.142440573 | 15/26 | 70.94194667 | CID | stationary-phase lysate, chymotrypsinized, IW=2 |
| NRATSnFSDTSLL (SEQ ID NO:92) | < 5% FDR | 4.419594577 | 13/24 | 82.37357833 | CID | stationary-phase lysate, chymotrypsinized, IW=4 |
| TSVQAIVDnTTESNSIW (SEQ ID NO:93) | < 1% FDR | 1.808727186 | 14/32 | 113.8540433 | CID | stationary-phase lysate, chymotrypsinized, IW=2 |
| EIDGITTEKnVTDMLY (SEQ ID NO:94) | < 5% FDR | 3.69485794 | 14/30 | 105.8570467 | CID | log-phase lysate, chymotrypsinized, IW=4 |
| FDDTMLDVIPSDLQLnAT (SEQ ID NO:95) | < 5% FDR | 4.341058574 | 11/34 | 140.8532017 | CID | stationary-phase lysate, chymotrypsinized, IW=4 |
| NGVNYAFFNnITYTAPK (SEQ ID NO:96) | < 5% FDR | 3.367848629 | 22/32 | 108.7651183 | CID | log-phase lysate, trypsinized, IW=4 |
| SSGDQAnNSEIYGSNTHTF (SEQ ID NO:97) | < 1% FDR | 3.276944913 | 14/36 | 67.24459667 | CID | log-phase lysate, chymotrypsinized, IW=4 |
| TVLVHTKnDTDKNF (SEQ ID NO:98) | < 5% FDR | 6.616159372 | 9/26 | 47.40241167 | CID | log-phase lysate, chymotrypsinized, IW=4 |
| SRYnQTETFKEY (SEQ ID NO:99) | < 5% FDR | 4.308045644 | 10/22 | 55.96619833 | CID | log-phase lysate, trypsinized, IW=4 |
| DGAEIDTncTDITK (SEQ ID NO:100) | < 1% FDR | 5.171707551 | 17/26 | 57.77886167 | CID | log-phase lysate, trypsinized, IW=4 |
| ILGIDPnVTQY (SEQ ID NO:101) | < 5% FDR | 6.384540278 | 14/20 | 106.3983783 | CID | stationary-phase lysate, trypsinized, IW=4 |
| VRnWTASITDEVAGEVK (SEQ ID NO:102) | < 1% FDR | 4.841725348 | 24/32 | 96.34111167 | CID | log-phase lysate, trypsinized, IW=2 |
| AGNEVTNnYTNTDASAF (SEQ ID NO:103) | < 1% FDR | 1.860661289 | 14/32 | 74.840735 | CID | stationary-phase lysate, chymotrypsinized, IW=2 |

FIG. 10O

| Sequence | Confidence | ΔM [ppm] | Ions Matched | RT [min] | Activation Type | Sample |
|---|---|---|---|---|---|---|
| AlnTTLDHSEcm (SEQ ID NO:104) | < 1% FDR | 4.157996484 | 15/22 | 48.73149167 | CID | log-phase lysate, chymotrypsinized, IW=4 |
| AlnTTLDHSEcM (SEQ ID NO:104) | < 1% FDR | 4.171941778 | 17/22 | 62.21560167 | CID | stationary-phase lysate, chymotrypsinized, IW=4 |
| FFYSNnGSQFY (SEQ ID NO:105) | < 1% FDR | 3.900626072 | 16/20 | 102.130425 | CID | log-phase lysate, trypsinized, IW=4 |
| FFYSNnGSQFY (SEQ ID NO:105) | < 1% FDR | 6.227598747 | 16/20 | 101.6736167 | CID | stationary-phase lysate, trypsinized, IW=4 |
| FNWIcNEVDcSGISAnGTAGK (SEQ ID NO:106) | < 1% FDR | 3.82479384 | 21/40 | 100.5815067 | CID | log-phase lysate, trypsinized, IW=4 |
| FNWIcNEVDcSGISAnGTAGK (SEQ ID NO:106) | < 1% FDR | 3.9222250784 | 20/40 | 99.61747 | CID | stationary-phase lysate, trypsinized, IW=2 |
| GVAYQADTAnETSGSTVNDPLANYEScSR (SEQ ID NO:107) | < 1% FDR | 4.368989134 | 51/112 | 86.60203167 | CID | log-phase lysate, trypsinized, IW=4 |
| GVAYQADTAnETSGSTVNDPLANYEScSR (SEQ ID NO:107) | < 1% FDR | 1.4209967439 | 33/112 | 84.70260333 | CID | log-phase lysate, trypsinized, IW=2 |
| KTVVDTFAnYTNV (SEQ ID NO:108) | < 1% FDR | 4.673216267 | 16/24 | 95.03383 | CID | stationary-phase lysate, chymotrypsinized, IW=4 |
| nLSIPVFFSEYGcNEVTPR (SEQ ID NO:109) | < 1% FDR | 4.262846462 | 15/36 | 129.3478867 | CID | log-phase lysate, trypsinized, IW=4 |
| ANGTnSTTNTTAESSQL (SEQ ID NO:4)³ | < 1% FDR | 5.428493193 | 21/34 | 50.04994 | CID | stationary-phase lysate, chymotrypsinized, IW=4 |
| EYSnFTTPYGL (SEQ ID NO:110) | < 5% FDR | 7.1153339928 | 11/20 | 102.8175583 | CID | stationary-phase lysate, trypsinized, IW=4 |
| EYSnFTTPYGL (SEQ ID NO:110) | < 5% FDR | 2.190332622 | 10/20 | 102.6243633 | CID | stationary-phase lysate, trypsinized, IW=2 |
| GGQVPITnSSLTHTNY (SEQ ID NO:111) | < 5% FDR | 4.874899668 | 15/30 | 72.071485 | CID | stationary-phase lysate, chymotrypsinized, IW=4 |
| NSSSALnITELY (SEQ ID NO:1) | < 5% FDR | 4.723602355 | 15/22 | 107.7726883 | CID | stationary-phase lysate, chymotrypsinized, IW=4 |
| NSSSALnITELY (SEQ ID NO:1) | < 5% FDR | 1.68094429 | 15/22 | 106.1771183 | CID | stationary-phase lysate, chymotrypsinized, IW=2 |

| Sequence | Confidence | ΔM [ppm] | Ions Matched | RT [min] | Activation Type | Sample |
|---|---|---|---|---|---|---|
| NVARVVnETIQDK (SEQ ID NO:112) | < 1% FDR | 4.420831558 | 15/24 | 62.485355 | CID | log-phase lysate, chymotrypsinized, IW=4 |
| NVARVVnETIQDK (SEQ ID NO:112) | < 1% FDR | 4.336598863 | 15/24 | 61.91798833 | CID | stationary-phase lysate, chymotrypsinized, IW=4 |
| QIVTGGQVPITNSSLTHTnY (SEQ ID NO:113) | < 1% FDR | 3.362642611 | 18/40 | 96.26060833 | CID | stationary-phase lysate, chymotrypsinized, IW=2 |
| QIVTGGQVPITnSSLTHTnYTR (SEQ ID NO:2)4 | < 5% FDR | 6.942564027 | 18/88 | 84.806355 | CID | stationary-phase lysate, trypsinized, IW=4 |
| SGSTnSTSSTIESTEIPVVy (SEQ ID NO:114) | < 1% FDR | 5.128550606 | 22/38 | 102.0710383 | CID | stationary-phase lysate, chymotrypsinized, IW=4 |
| SIIFDTEKPIVVTEDSAYAIPVANNKnATKRG VL (SEQ ID NO:115) | < 1% FDR | 3.797812756 | 45/198 | 111.1218517 | CID | stationary-phase lysate, chymotrypsinized, IW=4 |
| TRLFnSSSSAL (SEQ ID NO:116) | < 5% FDR | 4.232228195 | 15/18 | 75.13028 | CID | stationary-phase lysate, chymotrypsinized, IW=4 |
| STNnFTISIPEK (SEQ ID NO:117) | < 5% FDR | 2.856364821 | 14/22 | 81.85508 | CID | stationary-phase lysate, trypsinized, IW=2 |
| VAKnTSAITTDGGIY (SEQ ID NO:118) | < 5% FDR | 4.488536171 | 16/28 | 63.75786333 | CID | stationary-phase lysate, chymotrypsinized, IW=4 |
| LnGTWAADNKDWVNSL (SEQ ID NO:119) | < 1% FDR | 2.417945511 | 12/30 | 109.109735 | CID | stationary-phase lysate, chymotrypsinized, IW=4 |
| ATAnFSDSSEVLSK (SEQ ID NO:120) | < 5% FDR | 2.973134564 | 15/26 | 64.41178833 | CID | stationary-phase lysate, trypsinized, IW=2 |
| EATSISQnESAWLEK (SEQ ID NO:121) | < 5% FDR | 4.969792146 | 15/28 | 77.70658 | CID | stationary-phase lysate, trypsinized, IW=2 |
| NnFTDDPEFMGcVGcAIIR (SEQ ID NO:122) | < 5% FDR | 5.390754309 | 22/36 | 115.0503867 | CID | stationary-phase lysate, trypsinized, IW=2 |
| AGNEVINSVnTTNTATY (SEQ ID NO:123) | < 5% FDR | 2.19914069 | 17/32 | 73.84112667 | CID | stationary-phase lysate, chymotrypsinized, IW=2 |
| ASSSnSSTPSIEIK (SEQ ID NO:124) | < 5% FDR | 3.270879302 | 13/26 | 55.53289667 | CID | log-phase lysate, trypsinized, IW=4 |
| GVDYQPGGSSnLTDPLADASVcDR (SEQ ID NO:125) | < 1% FDR | 0.739448811 | 34/92 | 94.11038167 | CID | stationary-phase lysate, trypsinized, IW=4 |
| GVDYQPGGSSnLTDPLADASVcDR (SEQ ID NO:125) | < 1% FDR | 3.231773824 | 22/46 | 93.52831167 | CID | stationary-phase lysate, trypsinized, IW=2 |
| SGGLVVEYSnETNNYGLVQIDGDKVTK (SEQ ID NO:126) | < 1% FDR | 3.683761856 | 26/104 | 99.52912667 | CID | stationary-phase lysate, trypsinized, IW=4 |

| Sequence | Confidence | ΔM [ppm] | Ions Matched | RT [min] | Activation Type | Sample |
|---|---|---|---|---|---|---|
| SKVSNPEGNGGYSTSNnY (SEQ ID NO:127) | < 1% FDR | 3.133687731 | 21/34 | 49.62842833 | CID | log-phase lysate, chymotrypsinized, IW=4 |
| DTnSTAELQSPSSQEILGW (SEQ ID NO:128) | < 1% FDR | 6.233055736 | 17/36 | 117.4008333 | CID | stationary-phase lysate, chymotrypsinized, IW=4 |
| EEVVDYTQNnATYAVR (SEQ ID NO:129) | < 1% FDR | 4.011535879 | 18/30 | 70.12921333 | CID | stationary-phase lysate, trypsinized, IW=2 |
| GWSHATFPTIYQTcnETNAR (SEQ ID NO:130) | < 1% FDR | 2.660040304 | 17/38 | 86.83798667 | CID | stationary-phase lysate, trypsinized, IW=2 |
| TLDNDGNDIPVGLnDSVAYSK (SEQ ID NO:131) | < 1% FDR | 3.922911446 | 16/40 | 89.55506833 | CID | log-phase lysate, trypsinized, IW=4 |
| GIEPNcPINIPLScSnK (SEQ ID NO:132) | < 1% FDR | 0.593835771 | 17/32 | 90.40512833 | CID | stationary-phase lysate, trypsinized, IW=2 |
| AnGTEFAIQY (SEQ ID NO:133) | < 1% FDR | 6.88420871 | 13/18 | 89.810165 | CID | stationary-phase lysate, trypsinized, IW=4 |
| NGYnFTIGPY (SEQ ID NO:134) | < 5% FDR | 4.379401858 | 12/18 | 107.7844983 | CID | stationary-phase lysate, chymotrypsinized, IW=4 |

NOTES:
1 sequence ambiguity with YBR093C
2 sequence ambiguity with YBR092C
3 glycosite ambiguity with AnGTNSTNTTAESSQL
4 Doubly glycosylated, see Fig. S2

FIG. 10R

ISOTOPIC RECODING FOR TARGETED TANDEM MASS SPECTROMETRY

CROSS-REFERENCE

This application claims the benefit of U.S. Provisional Patent Application No. 61/753,774 filed Jan. 17, 2013, which application is incorporated herein by reference in its entirety.

GOVERNMENT RIGHTS

This invention was made with Government support under CA130447, GM066047 awarded by the National Institutes of Health and W81XWH-09-01-0627 awarded by the Department of the ARMY/MRMC. The Government has certain rights in this invention.

INCORPORATION BY REFERENCE OF SEQUENCE LISTING PROVIDED AS A TEXT FILE

A Sequence Listing is provided herewith as a text file, "BERK-204 SeqList_ST25.txt" created on Jan. 9, 2014 and having a size of 56 KB. The contents of the text file are incorporated by reference herein in their entirety.

INTRODUCTION

Post-translational modifications (PTMs) can profoundly impact a protein's molecular biology, and determining their function is a grand challenge in post-genomic biology. Locating the sites of modification is often an essential first step toward ascertaining the biological roles of PTMs, and liquid chromatography coupled to tandem mass spectrometry (LC-MS/MS) is well-suited for this purpose. However, the unambiguous assignment of PTM locations using existing LC-MS/MS methodology is sometimes difficult to achieve, particularly in cases involving low protein abundance or low site occupancy. Adding to the technical challenge of site-mapping, PTMs such as glycosylation are known to reduce ionization efficiency and therefore, detectability via mass spectrometry. In highly complex proteomic samples, low-intensity ions generated from glycopeptides may be overlooked due to instrument-dependent limitations on the rate at which ions can be selected for fragmentation during data-dependent acquisition.

In eukaryotes, asparagine-linked glycosylation (N-glycosylation) is a PTM frequently found on proteins that are translated into the endoplasmic reticulum (ER). Structurally conserved N-glycan precursors are synthesized via the dolichol pathway and transferred onto nascent proteins; the glycosylated asparagine (Asn) residues are typically found within a subset of the polypeptide's N-X-S/T motifs where X is a non-proline residue. Biologically, N-glycans contribute to the folding, trafficking, and thermodynamic stability of proteins exposed to ER, vacuolar, and golgi lumens as well as those destined for exposure to the extracellular milieu. The N-glycan precursors are enzymatically edited to yield a plethora of mature glycoforms with compositions largely dependent on cell type and protein localization. Sometimes, specific N-glycan structures are required for protein function, while in other cases, N-glycans primarily contribute to protein stability and solubility. As a class, the N-glycosylation modification is biologically essential; chemical or genetic disruption of N-glycan biosynthesis is lethal and aberrant N-glycosylation is associated with several human disease states.

Many existing LC-MS/MS approaches for mapping N-glycosites depend on enzymatic removal of the entire N-glycan following stringent sample enrichment to remove non-glycosylated peptides prior to analysis. These methods rely on detection of a 0.98 Da mass increase resulting from the enzymatic deamination of glycosylated Asn residues by peptide:N-glycosidase F (PNGase F). Enzymatic deamination is often performed in the presence of $^{18}$O-labeled water, imparting a 2.98 Da mass shift to the peptide to increase confidence in site assignment. Unfortunately, complete removal of N-glycans with PNGase F can lead to instances of incorrectly mapped glycosites. During the course of PNGase F treatment, spontaneous deamination of non-glycosylated Asn residues and other instances of PNGase F-independent incorporation of $^{18}$O can potentially yield false positives. This drawback has led to the development of alternative strategies utilizing partial rather than total removal of N-glycans. For instance, treating samples with the enzyme endoglycosidase H (endo H) preserves a single core N-acetyl-glucosamine (GlcNAc) residue, leaving direct evidence for N-glycosylation intact. Unfortunately, the presence of even a single sugar residue on peptides is known to considerably suppress ionization efficiency, potentially biasing data-dependent LC-MS/MS data acquisition against glycopeptide ions. Despite this limitation, detection of the retained glycan by LC-MS/MS provides glycosite assignment instead of indirect evidence that the N-glycan modification once existed at a given site. There is a need in the art for a method for detecting low-abundance ions for tandem MS; such methods are useful in facilitating glycosite mapping.

SUMMARY

Aspects of the present disclosure include methods for detecting a low abundance protein and methods for isotopic recoding. The present disclosure also provides methods for identifying a site of glycosylation on a protein (e.g., N-glycosylation).

In practicing methods according to certain embodiments of the present disclosure, a eukaryotic cell is contacted with an isotopic labeling composition (also referred to herein as an "isomix") and isotopically labeled N-glycosylated peptides obtained from the eukaryotic cell are assessed by liquid chromatography-tandem mass spectrometry (LC-MS/MS). A predetermined isotopic pattern in the mass spectrum is identified and amino acid sequences of the peptides containing the predetermined isotopic pattern are determined. Systems for identifying a predetermined isotopic pattern in complex mass spectra are also described.

In some embodiments, a directed proteomic approach where LC-MS/MS analysis is focused specifically on peptides bearing N-glycosylation, a common PTM found in all major phylogenetic branches of life is described. In contrast to data-dependent methods that select a subset of relatively intense ions for fragmentation, methods of the present disclosure are specifically designed to provide intensity-independent fragmentation priority to peptides most likely to bear N-glycans and boost confidence in correct PTM (e.g., glycosylation) site assignment. In certain instances, methods include imparting a perturbation to an peptide isotopic envelope. In certain instances, methods include imparting a perturbation to a peptide isotopic envelope without requiring chemical tagging (i.e., non-natural chemical modification). In certain instances, methods include imparting a perturbation to a peptide isotopic envelope with chemical tagging (i.e., non-natural chemical modification). In certain instances, methods include imparting a perturbation to an peptide isotopic envelope by metabolic labeling. In some embodiments, methods of the disclosure are directed to metabolically embedding a predetermined isotopic pattern directly into post-translational modifications (e.g., glycans). As described in greater detail below, in certain instances the predetermined isotopic pattern may be installed using a stoichiometrically defined mixture of N-acetyl-glucosamine (GlcNAc) isotopologs (e.g., a GlcNAc isomix). In these embodiments, the GlcNAc isotopologs are metabolically installed into structurally conserved N-glycan core positions, marking them with a uniquely identifiable isotopic pattern.

Systems for practicing the subject methods including liquid chromatography, mass spectrometers and computer systems for obtaining mass spectrum, identifying a predetermined isotopic pattern in the mass spectrum and determining amino acid sequences of peptides containing the predetermined isotopic pattern are also of interest. For example, systems may include liquid chromatography-tandem mass spectrometers for obtaining mass spectra. Furthermore, systems may also include computer systems which contain a processor with algorithms which include instructions to assess the mass spectra to identify a predetermined isotopic pattern of an peptide in the mass spectra and for determining the amino acid sequence of the peptide and the site of N-glycosylation on the protein based on the determined amino acid sequence of the peptide or to receive spectra from a mass spectrometer to identify a predetermined isotopic pattern of an peptide in the mass spectra and for detecting a low-abundance protein by identifying the amino acid sequence of an peptide obtained from the low-abundance protein.

The precursor ion that was selected from the inclusion list is indicated and the 4 Da isolation window used for fragmentation is shown in gray. (c) The CID fragmentation spectra and the peptide (SEQ ID NO:2) assignment for the 758.87 ion (lowercase n refers to the N-glycosite). Fragment ions that lack the GlcNAc isomix (such as the $y_4^+$ and $b_6^+$ fragment ions) have narrow isotopic envelopes, while fragments including the GlcNAc isomix (such as the $y_6^+$ and $b_8^+$ fragment ions) show a perturbed isotopic envelope characteristic of the isomix signature.

Figure 3A:
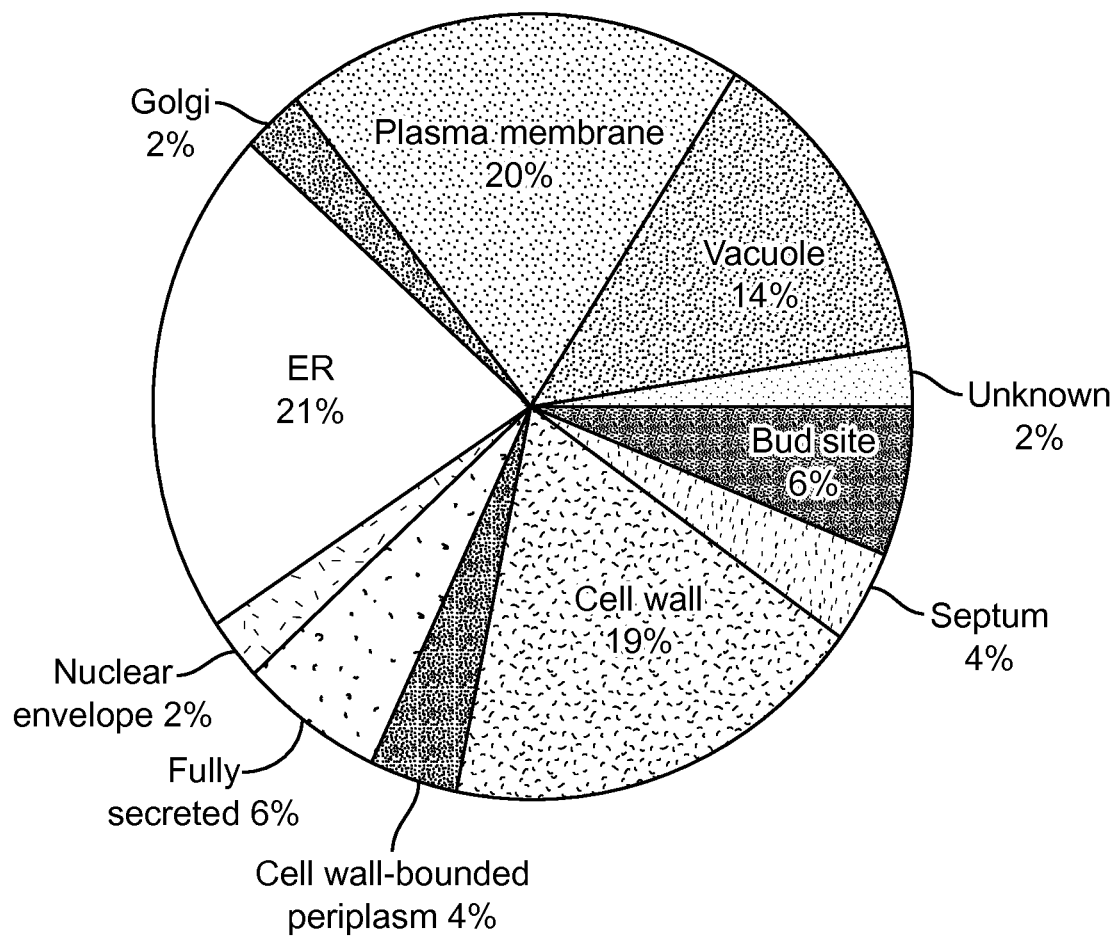
Figure 3B:
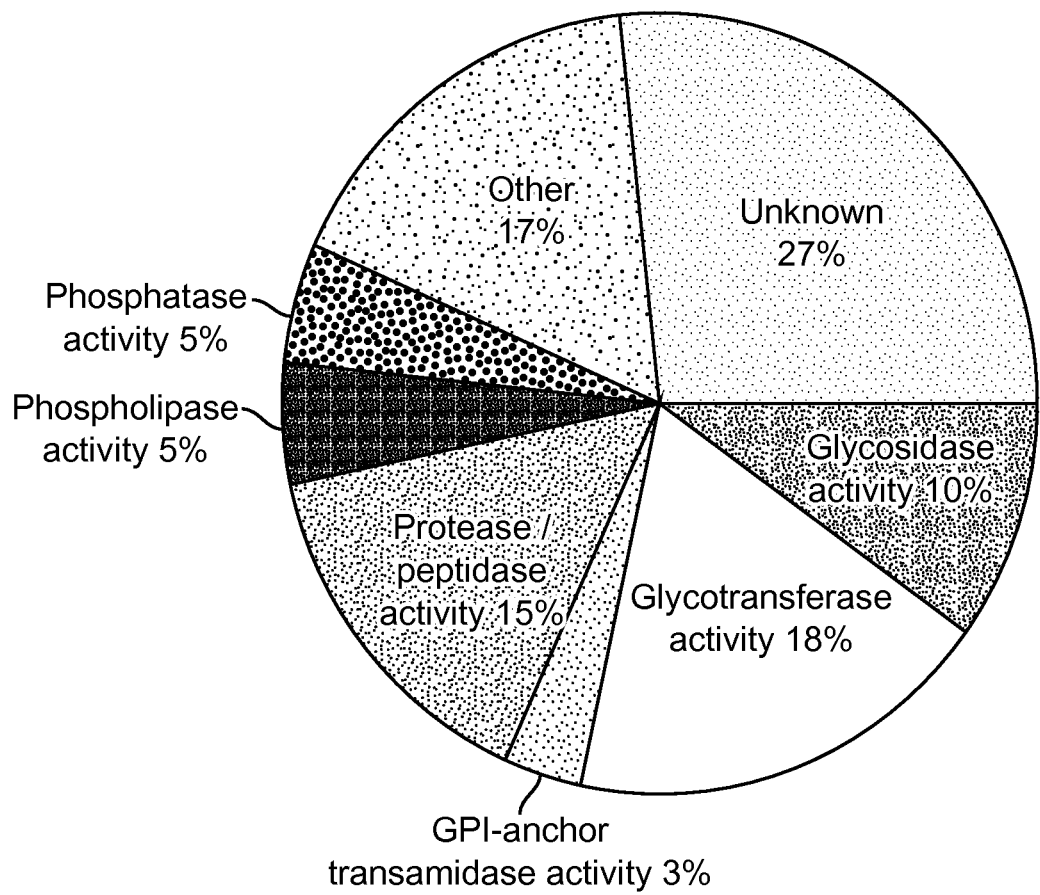
Figure 3C:
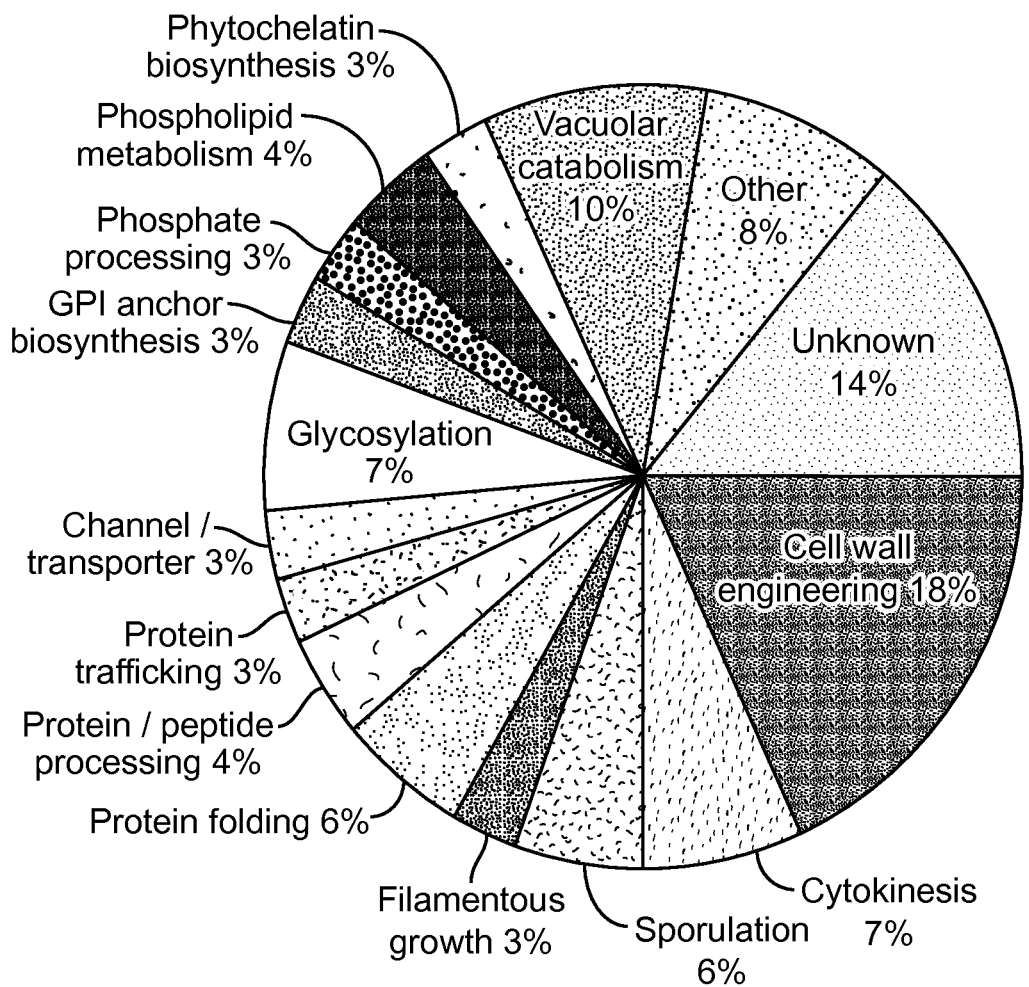

FIGS. 3a-c show the ontological analysis of high confidence N-glycoproteins according to certain embodiments of the present disclosure. N-glycoproteins were categorized according to the manually curated ontological annotations including (a) cellular component, (b) molecular function, and (c) biological process maintained by the Saccharomyces Genome Database(31).

Figure 4:
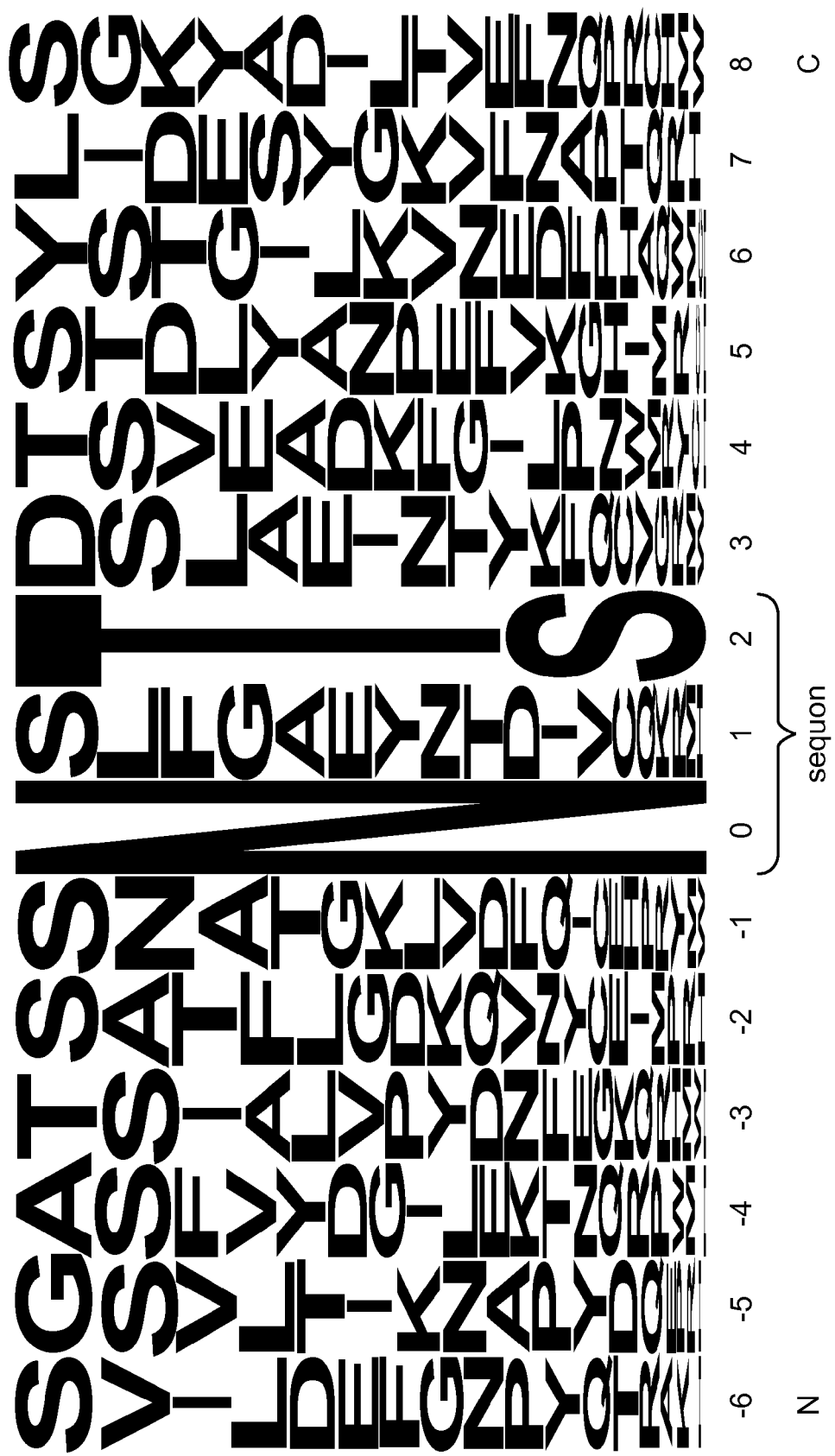
Figure 5:
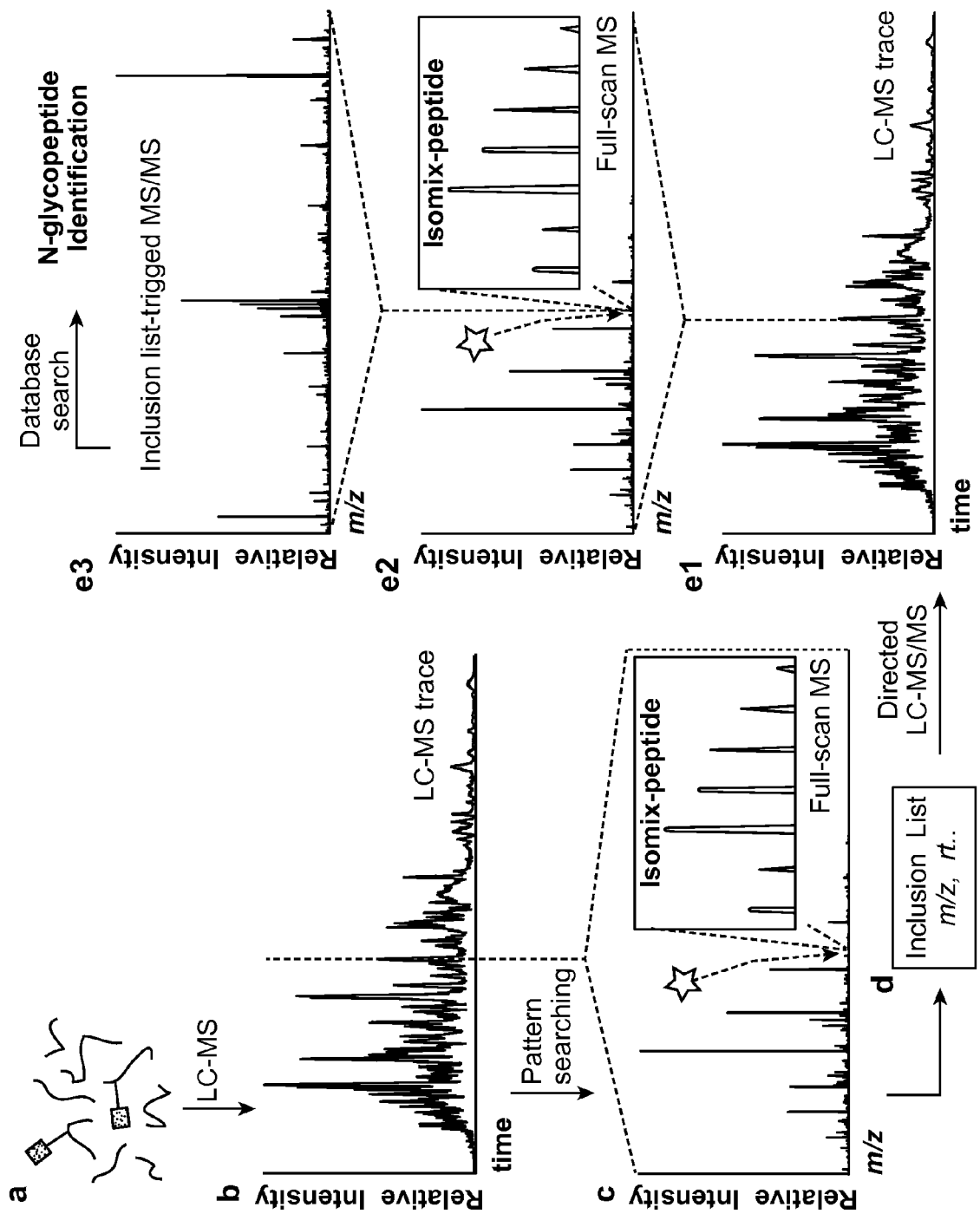

FIG. 4 shows the relative frequencies of residues surrounding yeast N-glycosites. Sequences (SEQ ID NO:1-2, 4-134) of the 133 unique glycosylation sites detected by directed LC-MS/MS are aligned on the modified Asn residue. Relative heights of the surrounding amino acids are adjusted based on the frequencies of their occurrence.

FIGS. 5a-e show GlcNAc isomix labeling can facilitate directed LC-MS/MS experiments according to certain embodiments of the present disclosure. (a) A complex mixture of peptides, where some are N-glycosylated and contain the GlcNAc isomix (boxes), is (b) separated using LC and full-scan mass spectra are collected. (c) Isomix-labeled peptides are identified using a pattern searching algorithm(3) and inventoried into an (d) inclusion list (rt=retention time). (e1-3) Subsequently, the same sample is subjected to a directed LC-MS/MS experiment where (e3) MS/MS analysis is only performed on (e2) precursor ions defined in the inclusion list. Data are then subjected to a database search for N-glycosite identification.

FIGS. 6a-d show the perturbing effect of two GlcNAc isomix residues on a peptide's isotopic envelope. Simulated isotopic envelopes for the Ygp1 peptide (QIIVTGGQVPIT-NSSLTHTNYTR; SEQ ID NO:2) which contain (a) zero, (b) one, or (c) two GlcNAc isomix residues (modified sequons are highlighted in red). (d) In experimental LC-MS data, we observed a doubly-glycosylated form of the Ygp1 peptide with an isotopic envelope closely matching simulation.

FIGS. 7a-b show an example of spectral misassignment from data-dependent analysis of an isomix-labeled sample. (a) The isotopic envelope of a precursor ion selected for data-dependent fragmentation lacks the characteristic GlcNAc isomix signature, in contrast to that illustrated in FIG. 2. The envelope's monoisotopic peak is indicated and the 4 Da IW is shown in gray. (b) The CID fragmentation spectrum and SEQUEST assignment to the indicated Akl1 peptide (SEQ ID NO:3) appear both statistically and visually reasonable (XCorr=2.90, FDR<5%). However, the lack of an isomix signature in the precursor and fragment ions serves as a basis for rejecting the assignment.

Figure 8:
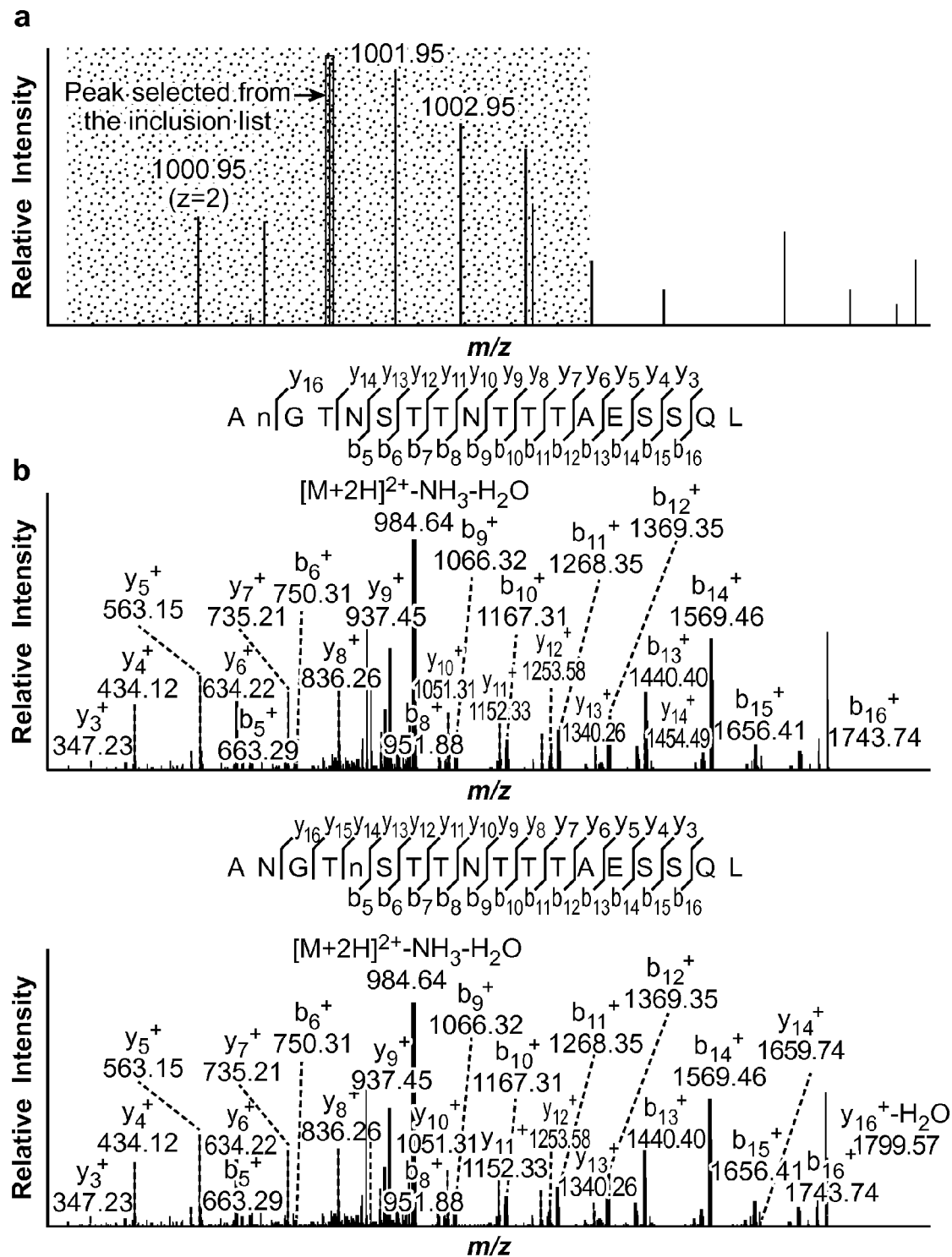

FIGS. 8a-b show glycosite ambiguity in a peptide from Ygp1. (a) The precursor ion isotopic envelope corresponding to the singly-glycosylated Ygp1 peptide ANGTNSTTNTT-TAESSQL (SEQ ID NO:4) is shown. The peak selected from the inclusion list is indicated and the 4 Da isolation window used for fragmentation is shown in gray. The peptide contains three potential sites for N-glycosylation. (b) The CID fragmentation spectrum can be plausibly assigned to either AnGTNSTTNTTTAESSQL (SEQ ID NO:4) or ANGTnSTT-NTTTAESSQL (SEQ ID NO:4), where the lowercase n indicates the glycosylated residue. Due to low signal to noise for fragment ions covering the peptide's N-terminus, definitive glycosite assignment could not be made even after close examination of individual fragment ion envelopes.

FIGS. 9a-b depicts Table 1 which is a list of occupied high confidence N-glycosites detected in the *S. cerevisiae* proteome.

FIGS. 10a-r depicts Table 2 which is a list of the observed tryptic and chymotryptic peptides containing these glycosites and corresponding statistical indicators of quality.

DETAILED DESCRIPTION

Aspects of the present disclosure include methods for detecting a low abundance protein in a complex mixture and methods for identifying a site of N-glycosylation on a protein. In practicing methods according to certain embodiments, a eukaryotic cell is contacted with an isotopic labeling composition and isotopically labeled N-glycosylated peptides obtained from the eukaryotic cell are assessed by liquid chromatography-tandem mass spectrometry. A predetermined isotopic pattern in the mass spectrum is identified and amino acid sequences of the peptides containing the predetermined isotopic pattern are determined Systems for identifying a predetermined isotopic pattern in mass spectra and determining amino acid sequences of peptides containing the predetermined isotopic pattern are also described.

The present disclosure provides methods and systems for identifying a site of N-glycosylation on a protein and for detecting a low-abundance protein in a biological sample. In certain embodiments the methods and systems include embedding a uniquely identifiable isotopic signature into biological molecules (e.g., glycans) and utilizing liquid-chromatography-tandem mass spectrometry to analyze one or more aspects of the molecules.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polypeptides. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, blood fractions such as plasma and serum, and the like. In some cases, a biological sample includes cells or cell fractions.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in that stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the isotopic labeling composition" includes reference to one or more isotopic labeling compositions and equivalents thereof known to those skilled in the art, and so forth.

It is also noted that definitions provided in one section of this application (e.g., the "Methods" section) may also apply to embodiments described in another section of the application (e.g., the "Systems" section) even if a term is described as applying to an embodiment of a particular section.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflict with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods for Identifying a Site of N-Glycosylation on a Protein and Detecting and Identifying a Low-Abundance Protein As described above, the present disclosure provides methods for identifying a site of glycosylation on a protein and for detecting a low-abundance protein in a biological sample. In certain aspects the disclosure includes methods for identifying a site of N-glycosylation (i.e., N-linked glycosylation). Although the following description is directed to identifying a site of N-glycosylation on a protein, the subject methods may also be applicable to glycosylation broadly including other types of glycosylation such as O-glycosylation. In certain embodiments, the methods include embedding a uniquely identifiable isotopic signature into biological molecules (e.g., proteins having one or more isotopically labeled glycans) and utilizing liquid-chromatography-tandem mass spectrometry (referred to hereafter as LC-MS/MS) to analyze one or more aspects (e.g., the location of N-glycosites thereon) of the molecules.

Identifying a Site of N-Glycosylation on a Protein

Disclosed methods for identifying a site of N-glycosylation on a protein may include one or more of the steps of (1) contacting a eukaryotic cell with an isotopic labeling composition; (2) subjecting an isotopically labeled biological sample obtained from the eukaryotic cell to LC-MS/MS; (3) identifying a predetermined isotopic pattern in a mass spectrum at one or more retention times; (4) determining an amino acid sequence of a peptide present at the one or more retention times; and (5) identifying the site of N-glycosylation on the protein based on the determined peptide sequence.

The terms "protein", and "polypeptide," as used herein, refer to a peptide-linked chain of amino acids, regardless of post-translational modification, e.g., glycosylation or phosphorylation. Thus the term protein does not refer to a single entity, rather it encompasses proteins resulting from post-translational modifications and N- and/or C-terminal processing of the same gene product. In some instances, a protein is an amino acid chain longer than 25 amino acid residues in length.

As referred to herein, the term "peptide", means a chain of amino acids which may be a portion or fragment of a protein and in certain instances, is less than about 25 amino acid residues in length. For example, a plurality of peptides are produced by proteolytic fragmentation of a protein (e.g., treatment with chymotrypsin or trypsin).

The phrase "site of N-glycosylation", as used herein, refers to any site on a protein where N-glycosylation may occur (i.e., N-glycosites). In some aspects, N-glycosylation occurs at a site on a protein where a sugar molecule attaches (i.e., binds) to a nitrogen atom in an amino acid residue of the protein. For example N-glycosylation may be where Asn residues in a protein are attached to a carbohydrate through a nitrogen atom (i.e., N-glycosites). N-glycosylation may occur, for example, on a eukaryotic protein (i.e., a protein of a eukaryotic cell).

As referred to herein, the term "eukaryotic cell" is used in its conventional sense to refer to one or more cells obtained from multi-cell organisms such animals, plants, fungi and yeast. As such, eukaryotic cells may include but are not limited to those obtained from yeast, fungi, plants, and animals including humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. In certain embodiments, eukaryotic cells include those obtained from a human being.

FIG. 1. presents a diagram illustrating one embodiment of certain aspects of the methods disclosed herein. Various steps and aspects of the methods shall now be described in greater detail below.

Administration of Isotopic Labeling Composition

As noted above, the present disclosure provides methods for identifying a site of N-glycosylation on a protein which, in certain embodiments, includes contacting a eukaryotic cell with an isotopic labeling composition.

The term "contacting" is used herein in its conventional sense to refer to placing two or more aspects in proximity or providing an interaction or communication between two or more aspects. For example, contacting may mean exposing (e.g., incubating with and/or allowing direct physical contact between) one aspect (e.g., an isotopic labeling composition) to another aspect (a cell). Contacting may also mean, for example, allowing one aspect to integrate with and/or penetrate and/or chemically react with another aspect.

The phrase "isotopic labeling composition", as used herein, refers to a chemical composition that can be used for isotopic labeling and is, in some instances, referred to as an "isomix". In some embodiments, an isotopic labeling composition is a composition that imparts sufficient perturbation to a peptide's isotopic envelope such that a successful targeted LC-MS/MS analysis may be conducted. An isotopic labeling composition can include 2 or more isotopic labels, 3 or more isotopic labels, 4 or more isotopic labels, or 5 or more isotopic labels. An isotopic labeling composition can include 2, 3, 4, 5, or more isotopic labels.

As used herein, the phrase "isotopic labeling" refers to one or more techniques or processes for tracking the passage of an isotope or atom with a variation through a metabolic pathway, cell or reaction. In some aspects, isotopic labeling includes replacing specific atoms of a reactant with their isotopes. In some aspects, isotopic labeling includes producing one or more isotopic labels. As used herein, the phrase "isotopic label" means a molecule (e.g., a sugar molecule) having at least one atom that has been replaced by an atom enriched in a specific isotope of that atom that differs from the natural abundance of isotopes of that atom (e.g., a detectable isotope). Isotopic labeling may also include detecting the presence and/or absence of one or more isotopic labels in a sample. In some embodiments, isotopic labels do not contain any halogen (e.g., bromine or chlorine) atoms.

In certain versions of the disclosed methods, contacting the eukaryotic cell with an isotopic labeling composition includes incubating the eukaryotic cell with a composition (i.e., an isotopic labeling composition) composed of one or more isotopic labels (e.g., one, two, three, four or five isotopic labels). As used herein, the term "incubating" means exposing an aspect (e.g., one or more cells) to a set of conditions (e.g., environmental conditions such as temperature and/or pressure) and/or placing an aspect in a specific physical location (e.g., a location where the aspect is exposed to one or more chemical compositions) for a length of time in order to produce a desired result (e.g., integration of at least one isotopic label into a biosynthetic pathway).

In particular embodiments of the disclosed methods, contacting the eukaryotic cell with an isotopic labeling composition includes metabolically embedding an isotopic signature into one or more molecules (e.g., glycans). By "metabolically embedding", as used herein, is meant inserting an aspect (e.g., one or more isotopic labels) into one or more metabolic processes (e.g., metabolic processes occurring within a eukaryotic cell). In some aspects, metabolic processes are associated with a glycan biosynthetic pathway (e.g., the gnalΔ yeast hexosamine biosynthetic pathway). As used herein, the term "glycan" refers to a polysaccharide or oligosaccharide.

In some instances, an isotopic signature includes a detectable characteristic of an isotopic label incorporated (e.g., metabolically embedded) into one or more molecules. In some aspects, metabolically embedding an isotopic signature does not include chemical tagging using one or more halogenated (e.g., dibrominated or dichlorinated) chemical tags. In some instances, an isotopic signature includes a detectable stoichiometric ratio of two or more isotopic labels. In some embodiments, an isotopic signature includes a detectable stoichiometric ratio of two or more isotopic labels that is unnatural. In particular embodiments, an isotopic signature is detectable by LC-MS/MS. In various instances, an isotopic signature is embedded into one or more molecules (e.g., glycans) within a eukaryotic cell. In some versions of the methods, an isotopic signature is metabolically embedded into a glycan core. In some aspects, an isotopic signature is embedded into one or more molecules by metabolically incorporating a defined mixture of N-acetylglucosamine isotopologs into N-glycans.

In various aspects of the disclosed methods, isotopic labels include, for example, N-acetyl-D-glucosamine, having the structure:

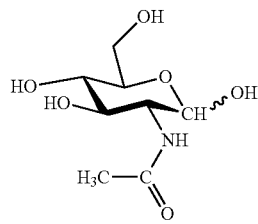

In particular versions of the disclosed methods, isotopic labels include, for example, N-[1,2-$^{13}C_2$]acetyl-D-glucosamine, having the structure:

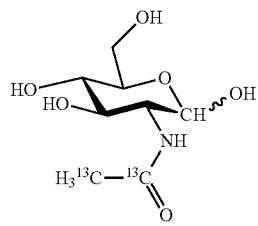

In some aspects of the disclosed methods, isotopic labels include, for example, N-[1,2-$^{13}C_2$]acetyl-D-[1-$^{13}C$;$^{15}N$]glucosamine, having the structure:

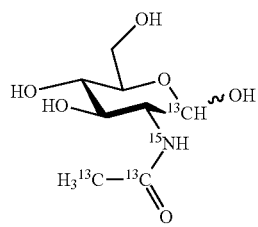

In select aspects of the disclosed methods, isotopic labels include N-acetyl-D-glucosamine, N-[1,2-$^{13}C_2$]acetyl-D-glucosamine and N-[1,2-$^{13}C_2$]acetyl-D-[1-$^{13}C$; $^{15}N$]glucosamine.

In some embodiments of the disclosed methods, isotopic labeling compositions include two isotopic labels. For example, in certain aspects, isotopic labeling compositions include two out of the three isotopic labels, N-acetyl-D-glucosamine, N-[1,2-$^{13}C_2$]acetyl-D-glucosamine and N-[1, 2-$^{13}C_2$]acetyl-D-[1-$^{13}C$;$^{15}N$]glucosamine, but not the third isotopic label.

In particular versions of the disclosed methods, isotopic labeling compositions include particular stoichiometric ratios of components thereof (e.g., isotopic labels). For example, isotopic labeling compositions composed of two or more components (e.g., isotopic labels) may include a stoichiometric ratio (e.g., molar ratio) of components of, for example, 1:1; 1:2; 1:3; 1:4; 1:5; 1:6; 1:7; 1:8; 1:9; 1:10; 1:11; 1:12; 1:13; 1:14; 1:15; 1:16; 1:17; 1:18; 1:19; or 1:20; etc. In various aspects, stoichiometric ratios of components of isotopic labeling compositions are measurable by a process (e.g., LC-MS/MS).

In some embodiments, isotopic labeling compositions composed of three or more components (e.g., isotopic labels) include a stoichiometric ratio of those components of, for example, 1:1:1; 1:2:1; 1:3:1; 1:4:1; 1:5:1; 1:6:1; 1:7:1; 1:8:1; 1:9:1; 1:10:1; 1:2:2; 1:3:2; 1:4:2; 1:5:2; 1:6:2; 1:7:2; 1:8:2; 1:9:2; or 1:10:2; 1:2:3; 1:3:3; 1:4:3; 1:5:3; 1:6:3; 1:7:3; 1:8:3; 1:9:3; or 1:10:3; etc. In some versions, isotopic labeling compositions include a stoichiometric ratio of 1:2:1 of N-acetyl-D-glucosamine, N-[1,2-$^{13}C_2$]acetyl-D-glucosamine and N-[1,2-$^{13}C_2$]acetyl-D-[1-$^{13}C$;$^{15}N$]glucosamine, respectively. In particular aspects, isotopic labeling compositions include a stoichiometric ratio of N-acetyl-D-glucosamine, N-[1,2-$^{13}C_2$]acetyl-D-glucosamine and N-[1,2-$^{13}C_2$]acetyl-D-[1-$^{13}C$;$^{15}N$]glucosamine in one or more of the above-listed ratios and in any possible combination or order.

As discussed above, the present disclosure provides methods for identifying a site of N-glycosylation on a protein which, in certain embodiments, includes subjecting an isotopically labeled biological sample obtained from the eukaryotic cell to LC-MS/MS. In some aspects, the biological sample obtained from the eukaryotic cell includes N-glycosylated proteins. By "N-glycosylated proteins" is meant proteins to which a sugar (e.g., glycan) molecule has attached to a nitrogen atom in an amino acid residue of the protein. By biological sample is meant a portion of biological (e.g., organic) material (e.g., protein) taken from a biological source (e.g., a eukaryotic cell) which, in some aspects, may be isotopically labeled. As such, the biological sample may include one or more different proteins, such as 2 or more different proteins, such as 5 or more different proteins, such as 10 or more different proteins, such as 50 or more different proteins, such as 100 or more different proteins, such as 1000 or more different proteins, and including 5000 or more different proteins.

In some instances, N-glycosylated proteins include one or more (e.g., two or three) isotopic labels (e.g., N-acetyl-D-glucosamine, and/or N-[1,2-$^{13}C_2$]acetyl-D-glucosamine, and/or N-[1,2-$^{13}C_2$]acetyl-D-[$^{13}C$;$^{15}N$]glucosamine).

Certain aspects of the disclosed methods include producing peptides from N-glycosylated proteins (e.g., isotopically labeled N-glycosylated proteins). Particular aspects of the disclosed methods include producing peptides from N-glycosylated proteins having one or more (e.g., two or three) isotopic labels (e.g., N-acetyl-D-glucosamine, and/or N-[1, 2-$^{13}C_2$]acetyl-D-glucosamine, and/or N-[1,2-$^{13}C_2$]acetyl-D-[1-$^{13}C$;$^{15}N$]glucosamine). In various embodiments, producing peptides from N-glycosylated proteins includes contacting N-glycosylated proteins with trypsin and/or chymotrypsin, however any convenient protocol for digesting a protein to produce peptide fragments for sequencing may be employed as desired.

Applying Liquid-Chromatography-Tandem Mass Spectrometry to Analyze a Biological Sample The present disclosure provides methods for identifying a site of N-glycosylation on a protein which, in some embodiments, includes subjecting an isotopically labeled biological sample obtained from a eukaryotic cell to liquid-chromatography-tandem mass spectrometry (LC-MS/MS). In some aspects, subjecting an isotopically labeled biological sample obtained from the eukaryotic cell to liquid-chromatography-tandem mass spectrometry (LC-MS/MS) includes selecting a portion of the biological sample for fragmentation and subjecting to fragmentation that selected portion. In some instances, the methods include selecting a portion of a biological sample for fragmentation based, at least in part, on the retention time of that portion (i.e., the retention time of that portion in a liquid chromatography process). The systems and operation of LC-MS/MS are described in more detail below.

Various embodiments of the methods include identifying a predetermined isotopic pattern in a mass spectrum at one or more retention times (i.e., retention times of a liquid chromatography process). A predetermined isotopic pattern may correspond, for example, to any of the stoichiometric ratios of the isotopic labeling compositions listed above.

In certain variations of the methods, identifying a predetermined isotopic pattern includes identifying a peak intensity ratio in the mass spectrum. For example, in some embodiments, identifying a predetermined isotopic pattern includes identifying a 1:2:1 peak intensity ratio in the mass spectrum. In some aspects, an identifiable peak intensity ratio in a mass spectrum may correspond to a stoichiometric ratio of two or more isotopic labels. In various embodiments, a 1:2:1 peak intensity ratio identified in the mass spectrum corresponds to a stoichiometric ratio of 1:2:1 of N-acetyl-D-glucosamine, to N-[1,2-$^{13}C_2$]acetyl-D-glucosamine, to N-[1,2-$^{13}C_2$]acetyl-D-[1-$^{13}C;^{15}N$]glucosamine, present in a sample.

Particular embodiments of the disclosed methods include determining an amino acid sequence of a peptide present at one or more retention times (i.e., retention times of a liquid chromatography process). Determining an amino acid sequence of a peptide may be achieved by any of the methods described herein or by other suitable methods. In various embodiments of the methods, retention times corresponding to amino acid sequences that are determined are selected based on the identification of a predetermined isotopic pattern using mass spectrometry.

Select aspects of the methods include identifying a site of N-glycosylation on a protein based on an amino acid sequence (e.g., a determined amino acid sequence) of a peptide present at one or more retention times (i.e., retention times of a liquid chromatography process).

Particular embodiments of the disclosed methods include generating an inclusion list of peptides having a mass spectrum that contains a predetermined isotopic pattern. In some embodiments, a predetermined isotopic pattern is an isotopic pattern corresponding to any of the stoichiometric ratios of the isotopic labeling compositions listed above. In various embodiments, a predetermined isotopic pattern is a 1:2:1 peak intensity ratio corresponding to a stoichiometric ratio of 1:2:1 of N-acetyl-D-glucosamine, to N-[1,2-$^{13}C_2$]acetyl-D-glucosamine, to N-[1,2-$^{13}C_2$]acetyl-D-[1-$^{13}C;^{15}N$]glucosamine.

In various instances, the disclosed methods include generating an inclusion list of peptides having a mass spectrum that contains a predetermined isotopic pattern and determining an amino acid sequence for each of the peptides on the inclusion list. As noted above, the inclusion list is a compilation or listing of one or more of 1) peptides (e.g., by standard name, UNIPROT ID or systematic name), 2) m/z values from a mass spectrometer, 3) m/z and retention time window and 4) m/z and retention time window and ion abundance which have been identified as having mass spectra containing a predetermined isotopic pattern as described above. The inclusion list may include any number of peptides, depending on the biological sample and may include 1 or more peptides, such as 2 or more peptides, such as 5 or more peptides, such as 10 or more peptides, such as 25 or more peptides, such as 50 or more peptides, such as 100 or more peptides, and including 250 or more peptides. As desired, one or more of the peptides on the inclusion list may be further subjected to determination of amino acid sequence and/or site of N-glycosylation. Determining an amino acid sequence of a peptide (e.g., one or more peptides on an inclusion list) may be achieved by any of the methods described herein or by other suitable methods, as described below.

Detecting Low-Abundance Proteins

Aspects of the present disclosure also include methods for detecting a low-abundance protein in a biological sample. Methods for detecting a low-abundance protein in a biological sample may include one or more of the steps of (1) contacting a eukaryotic cell with an isotopic labeling composition; (2) subjecting an isotopically labeled biological sample obtained from the eukaryotic cell to liquid-chromatography-tandem mass spectrometry (LC-MS/MS); and (3) identifying a predetermined isotopic pattern in a mass spectrum at one or more retention times of the liquid chromatograph to thereby detect the presence of the low-abundance protein in the biological sample.

The phrase "low-abundance protein", as used herein, refers to one or more proteins present in a sample in a sufficiently low quantity that they may be difficult to detect by some methods (e.g., LC-MS/MS approaches that select only the most intense ions in a given sample for fragmentation and/or further analysis). Low abundance proteins have a concentration that is less than that of high abundance proteins. For example, low abundance proteins may have a concentration of less than 100 ng/mL, such as less than 75 ng/mL, such as less than 50 ng/mL and including less than 25 ng/mL in a biological sample. In other embodiments low abundance proteins are present in a biological sample containing a mixture of proteins in an amount that is less than or equal to 1000 pg/mg of total protein in the biological sample, such as 750 pg/mg, such as 500 pg/mg and including equal to or less than 250 pg/mg of total protein in the biological sample. In certain instances, methods of the present disclosure include detecting and identifying low abundance proteins in a biological sample present in an amount that is equal to or less than 100 pg/mg of total protein, less than 50 pg/mg of total protein, or less than 10 pg/mg total protein.

Administration of Isotopic Labeling Composition

As noted above, various methods for detecting low-abundance protein in a biological sample include contacting a eukaryotic cell with an isotopic labeling composition. In certain embodiments of the disclosed methods, contacting the eukaryotic cell with an isotopic labeling composition includes incubating the eukaryotic cell with a composition (i.e., the isotopic labeling composition) composed of one or more isotopic labels (e.g., one, two, three, four or five isotopic labels). For example, the methods may include contacting a eukaryotic cell with an isotopic labeling composition composed of one or more of N-acetyl-D-glucosamine, N-[1,2-$^{13}C_2$]acetyl-D-glucosamine, and N-[1,2-$^{13}C_2$]acetyl-D-[1-$^{13}C;^{15}N$]glucosamine. In some embodiments, isotopic labeling compositions include a stoichiometric ratio of 1:2:1 of N-acetyl-D-glucosamine, N-[1,2-$^{13}C_2$]acetyl-D-glucosamine and N-[1,2-$^{13}C_2$]acetyl-D-[1-$^{13}C;^{15}N$]glucosamine, respectively.

The present disclosure provides methods for identifying a site of N-glycosylation on a protein which, in certain embodiments, includes subjecting an isotopically labeled biological sample obtained from the eukaryotic cell to LC-MS/MS. In some aspects, the biological sample obtained from the eukaryotic cell includes N-glycosylated proteins. In some aspects of the disclosed methods, N-glycosylated proteins include one or more (e.g., two or three) isotopic labels (e.g., N-acetyl-D-glucosamine, and/or N-[1,2-$^{13}C_2$]acetyl-D-glucosamine, and/or N-[1,2-$^{13}C_2$]acetyl-D-[1-$^{13}C$;$^{15}N$]glucosamine).

Particular versions of the disclosed methods of identifying low-abundance proteins include producing peptides from N-glycosylated proteins (e.g., isotopically labeled N-glycosylated proteins). Various aspects of the disclosed methods include producing peptides from N-glycosylated proteins having one or more (e.g., two or three) isotopic labels (e.g., N-acetyl-D-glucosamine, and/or N-[1,2-$^{13}C_2$]acetyl-D-glucosamine, and/or N-[1,2-$^{13}C_2$]acetyl-D-[1-$^{13}C$;$^{15}N$]glucosamine). In various embodiments, producing peptides from N-glycosylated proteins includes contacting N-glycosylated proteins with trypsin and/or chymotrypsin, however any convenient protocol for digesting a protein to produce peptide fragments for sequencing may be employed as desired.

Applying Liquid-Chromatography-Tandem Mass Spectrometry to Analyze a Biological Sample Some aspects of the methods include subjecting an isotopically labeled biological sample obtained from a eukaryotic cell to LC-MS/MS. For example, aspects of the methods may include subjecting a biological sample obtained from a eukaryotic cell and isotopically labeled with a an isotopic labeling composition composed of one or more of N-acetyl-D-glucosamine, N-[1,2-$^{13}C_2$]acetyl-D-glucosamine, and N-[1,2-$^{13}C_2$]acetyl-D-[1-$^{13}C$;$^{15}N$]glucosamine in a set stoichiometric ratio (e.g., 1:2:1, respectively) to LC-MS/MS.

Select embodiments of the disclosed methods for detecting a low-abundance protein include identifying a predetermined isotopic pattern in a mass spectrum at one or more retention times to thereby detect the presence of the low-abundance protein in the biological sample. In some embodiments, for example, identifying a predetermined isotopic pattern includes identifying a 1:2:1 peak intensity ratio in the mass spectrum. In some instances, an identifiable peak intensity ratio in a mass spectrum may correspond to a stoichiometric ratio of two or more isotopic labels. In various embodiments, a 1:2:1 peak intensity ratio identified in the mass spectrum corresponds to a stoichiometric ratio of 1:2:1 of N-acetyl-D-glucosamine, to N-[1,2-$^{13}C_2$]acetyl-D-glucosamine, to N-[1,2-$^{13}C_2$]acetyl-D-[1-$^{13}C$;$^{15}N$]glucosamine, present in a sample.

Particular instances of the disclosed methods include determining an amino acid sequence of a protein (e.g., a low-abundance protein). Determining an amino acid sequence of a peptide may be achieved by any of the methods described herein or by other suitable methods.

Some versions of the disclosed methods for detecting a low-abundance protein include generating an inclusion list of peptides having a mass spectrum that contains a predetermined isotopic pattern. In some embodiments, a predetermined isotopic pattern is an isotopic pattern corresponding to any of the stoichiometric ratios of the isotopic labeling compositions listed above. In various embodiments, a predetermined isotopic pattern is a 1:2:1 peak intensity ratio corresponding to a stoichiometric ratio of 1:2:1 of N-acetyl-D-glucosamine, to N-[1,2-$^{13}C_2$]acetyl-D-glucosamine, to N-[1,2-$^{13}C_2$]acetyl-D-[1-$^{13}C$;$^{15}N$]glucosamine.

In select embodiments, the disclosed methods include generating an inclusion list of peptides having a mass spectrum that contains a predetermined isotopic pattern and determining an amino acid sequence for each of the peptides on the inclusion list. As noted above, the inclusion list is a compilation or listing of one or more of 1) peptides (e.g., by standard name, UNIPROT ID or systematic name), 2) m/z values from a mass spectrometer, 3) m/z and retention time window and 4) m/z and retention time window and ion abundance which have been identified as having mass spectra containing a predetermined isotopic pattern as described above. The inclusion list may include any number of peptides, depending on the biological sample and may include 1 or more peptides, such as 2 or more peptides, such as 5 or more peptides, such as 10 or more peptides, such as 25 or more peptides, such as 50 or more peptides, such as 100 or more peptides, and including 250 or more peptides. As desired, one or more of the peptides on the inclusion list may be further subjected to determination of amino acid sequence. As noted above, determining an amino acid sequence of a peptide (e.g., one or more peptides on an inclusion list) may be achieved by any of the methods described herein or by other suitable methods.

Systems for Identifying a Site of N-Glycosylation on a Protein and Detecting and Identifying a Low-Abundance Protein Aspects of the present disclosure also include systems for practicing the subject methods including liquid chromatography, mass spectrometers and computer systems for obtaining mass spectrum, identifying a predetermined isotopic pattern in the mass spectra and determining amino acid sequences of peptides containing the predetermined isotopic pattern. Furthermore, systems may also include algorithms which include instructions to assess the mass spectra to identify a predetermined isotopic pattern of an peptide in the mass spectra and for determining the amino acid sequence of the peptide and the site of N-glycosylation on the protein based on the determined amino acid sequence of the peptide or to receive spectra from a mass spectrometer to identify a predetermined isotopic pattern of an peptide in the mass spectra and for detecting a low-abundance protein by determining the amino acid sequence of an peptide obtained from the low-abundance protein.

As described above, systems of the present disclosure may include liquid chromatography-mass spectrometry systems. For example, the apparatus may include analytical separation device such as a liquid chromatograph (LC), including a high performance liquid chromatograph (HPLC), a micro- or nano-liquid chromatograph or an ultra high pressure liquid chromatograph (UHPLC) device, a capillary electrophoresis (CE), or a capillary electrophoresis chromatograph (CEC) apparatus. However, any manual or automated injection or dispensing pump system may be used. For instance, a biological sample having a protein sample according to the subject methods may be applied to the LC-MS system by employing a nano- or micropump in certain embodiments.

Mass spectrometry systems employed in the subject methods may be any convenient mass spectrometer, including, but not limited to a matrix assisted laser desorption ionization (MALDI) operated in vacuum or at atmospheric pressure (AP-MALDI), electrospray ionization (ESI), chemical ionization (CI) operated in vacuum or at atmospheric pressure (APCI) or inductively coupled plasma (ICP), among others. Suitable mass spectrometry techniques include, but are not limited to, matrix-assisted laser desorption/ionization combined with time-of-flight mass analysis (MALDI-TOF MS) or electrospray ionization mass spectrometry (ESI MS). In certain embodiments, the mass spectrometric system is a tandem mass spectrometer and peptide fragmentation patterns are screened over available databases to determine the amino acid sequence of the subject peptides.

Methods for employing mass spectrometry for amino acid sequencing is discussed in greater detail in, e.g., End et al., "An Approach to Correlate Tandem Mass Spectral Data of Peptides with Amino Acid Sequences in a Protein Database", *J. Am. Soc. Mass Spectrom.*, 5:976-989, 1994; Swiderek K. et al. "The identification of peptide modifications derived from gel-separated proteins using electrospray triple quadrupole and ion trap analyses", *Electrophoresis,* 19:989-997, 1998; and Keough T. et al. "A method for high-sensitivity peptide sequencing using postsource decay matrix-assisted laser desorption ionization mass spectrometry", *Proc. Natl. Acad. Sci. USA,* 96:7131-7136, 1999, the disclosures of which are herein incorporated by reference. Methods for employing mass spectrometry for amino acid sequencing is also discussed in greater detail in, e.g., Aebersold, R. & Mann, M. Mass spectrometry-based proteomics. *Nature* 422, 198-207 (2003); Steen, H. & Mann, M. The ABC's (and XYZ's) of peptide sequencing. *Nat Rev Mol Cell Biol* 5, 699-711 (2004); Eng, J. K., Searle, B. C., Clauser, K. R. & Tabb, D. L. A face in the crowd: recognizing peptides through database search. *Mol Cell Proteomics* 10, R111 009522 (2011), the disclosures of which are herein incorporated by reference.

A computer system having algorithm is used to identify peptides having a predetermined isotopic pattern and to determine the sequence of amino acids of peptides determined to include the desired isotopic pattern.

In one embodiment the mass spectrometric technique is tandem mass spectrometry and the amino acid sequence of the identified peptides is determined. In some instances, a peptide entering the tandem mass spectrometer is selected and subjected to collision induced dissociation (CID). The spectra of a resulting fragment ion is recorded in the second stage of mass spectrometry (i.e., CID spectrum). In some instances, a peptide entering the tandem mass spectrometer is selected and subjected to electron transfer dissociation (ETD). This process may be repeated with other peptides selected to be included in the peptide inclusion list, described above. Alternatively, the peptides may be separated and purified and their sequences determined with an automated sequencer.

Where peptides are separated, purified and determined employing an automated sequencer, any convenient chromatographic protocol may be employed, including but not limited to high pressure liquid chromatography (HPLC), reverse-phase high pressure liquid chromatography (RP-HPLC), gel electrophoresis, capillary electrophoresis (CE), or other suitable chromatographic techniques. Likewise, any convenient automated peptide sequencer may be employed.

As described above, after determining the amino acid sequence of the identified peptides, a computer program can be used to determine the location on protein where the peptide originated, such as for example to determine the site of N-glycosylation. For example, protein sequences which can be employed to determine the location of N-glycosylation identified by the subject methods may include internet-accessible proteome databases is the Expert Protein Analysis System (ExPASy), available online at www(dot)expasy(dot)ch. Several databases in FASTA (ASCII text) format with protein sequence information can be accessed with standard web-browsing software over the world wide web (WWW). These include, for example, the SWISS—PROT data base (www(dot)expasy(dot)ch) and OWL database www(dot)biochem(dot)ucl dot)ac(dot)uk/bsm/dbbrowser/OWL/OWL(dot)html). Other protein databases include Incyte Genomics' Yeast Protein Database (YPD), WormPD, HumanPSD and G-Protein Coupled Receptor Protein Database (GPCR-PD), to cite a few (See: www(dot)incyte(dot)com/sequence/proteome/index(dot)shtml). Likewise, database searching can be carried out with computer-assisted database search programs, such as SEQUEST (Trademark, University of Washington, Seattle Wash.). See, for example, McCormack, A. L. et al. "Direct Analysis and Identification of Proteins in Mixtures by LC/MS/MS and Database Searching at the Low-Femtomole Level", *Anal. Chem.,* 69:767-776, 1996; Eng, J. K. et al. "An Approach to Correlate Tandem Mass Spectral Data of Peptides with Amino Acid Sequences in a Protein Database" *J. Amer. Soc. Mass. Spectrom.,* 5:976-989, 1994; Yates, III et al., U.S. Pat. No. 5,538,897; and Aebersold et al., WO 01/96869. For example, such program can operate to take all known genomic sequences, compute all possible theoretical CID spectra and compare them to experimental CID spectra for matches and sequence identification.

In certain embodiments, systems also include a computer that includes a computer readable storage medium having a computer program stored thereon, where the computer program when loaded on a computer operates the computer to: receive spectra from a mass spectrometer and includes a processor to assess the mass spectra to identify a predetermined isotopic pattern of an peptide in the mass spectra and for determining the amino acid sequence of the peptide and the site of N-glycosylation on the protein based on the determined amino acid sequence of the peptide. In other embodiments, systems include a computer that includes a computer readable storage medium having a computer program stored thereon, where the computer program when loaded on a computer operates the computer to: receive spectra from a mass spectrometer and includes a processor to assess the mass spectra to identify a predetermined isotopic pattern of an peptide in the mass spectra and for detecting a low-abundance protein by determining the amino acid sequence of an peptide obtained from the low-abundance protein.

In embodiments of the present disclosure, the system includes an input module, a processing module and an output module. In some embodiments, the subject systems may include an input module which is connected to the Internet such that data from mass spectra may be inputted from a remote location. The processing module includes memory having a plurality of instructions for assessing mass spectra. The processing module is also configured with an algorithm for determining an amino acid sequence of an peptide and determining the site of N-glycosylation on the protein based on the determined amino acid sequence. For example, the processor is configured with memory with instructions to perform the steps as described above to identify a predetermined isotopic pattern of an peptide in a mass spectrum, determine the amino acid sequence of the peptide containing the predetermined isotopic pattern and to determine the site of N-glycosylation on the protein based on the determined amino acid sequence.

After the processing module has assessed mass spectra, an output module communicates the results to the user, such as by displaying on a monitor or by printing a report or an inclusion list of peptides and/or the sites of N-glycosylation on the protein of interest.

The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Systems may include a display and operator input device. Operator input devices may, for example, be a keyboard, mouse, or the like. The processing module includes a processor which has access to a memory having instructions stored thereon for evaluating the inputted mass spectra and identifying a predetermined isotopic pattern of an peptide in a mass spectrum, determining the amino acid sequence of the peptide containing the predetermined isotopic pattern and determining the site of N-glycosylation on the protein based on the determined amino acid sequence. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Pert, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present disclosure can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media.

The processor may also have access to a communication channel to communicate with a user at a remote location By remote location is meant the user is not directly in contact with the system and relays input information to an input manager from an external device, such as a computer connected to a Wide Area Network ("WAN"), telephone network, satellite network, or any other suitable communication channel, including a mobile telephone (e.g., a smartphone). In these embodiments, input manager receives information, e.g., mass spectra, from a user, e.g., over the Internet, telephone or satellite network. Input manager processes and forwards this information to the processing module. These functions are performed using any convenient technique.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module (e.g., an inclusion list of one or more peptides containing the predetermined isotopic pattern) to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Windows XP, Windows 7, Sun Solaris, Linux, OS/400, Compaq Tru64 Unix, SGI IRIX, Siemens Reliant Unix, and others.

During use, a user or computer-automated control programmed by a human inputs mass spectra into the system, as determined by the methods described in detail above. The processing module is configured to assess the mass spectra and identify a predetermined isotopic pattern of peptides in the mass spectra, determining the amino acid sequence of one or more of the peptides containing the predetermined isotopic pattern and determining the site of N-glycosylation on the protein based on the determined amino acid sequences. Systems of the invention may screen a plurality of the biological samples containing a plurality of proteins.

In certain embodiments, the processing module is also configured to include a data customizing manager. The data customizing manager is a functional element that allows the user to input various parameters for evaluating the mass spectra. Furthermore, the data customizing manager is also configured so that a user can input or change criteria used to identify a predetermined isotopic pattern of peptides in the mass spectra, determine the amino acid sequence of one or more of the peptides containing the predetermined isotopic pattern or determine the site of N-glycosylation on the protein based on the determined amino acid sequences. For example, using the data customizing manager a user may customize which the intensity of ion signal from the mass spectra or the signal-to-noise ratio of data acquired from the mass spectra.

In certain embodiments, the processing module is also configured to include an input information manager. The input information manager provides information to a user regarding the criteria that was employed by the processor in identifying a predetermined isotopic pattern of peptides in the mass spectra, determining the amino acid sequence of one or more of the peptides containing the predetermined isotopic pattern or determining the site of N-glycosylation on the protein based on the determined amino acid sequences. For example, the input information manager provides a history of input information to a user at the request of the user. The input information may be in the form of a compendium of mass spectra data, inclusion lists, fragmentation patterns, ion intensities, etc. As such, the input information manager provides a user the ability to retrace the steps employed in designing a protocol for identifying a predetermined isotopic pattern of peptides in the mass spectra, determining the amino acid sequence of one or more of the peptides containing the predetermined isotopic pattern or determining the site of N-glycosylation on the protein based on the determined amino acid sequences, so that knowledge of the data that went into the development of the protocol can be readily obtained and used.

In certain embodiments, the processing module is configured to include a peptide fragmentation data comparison manager. The comparison manager is a functional element that is configured to compare one or more fragmentation data to each other or to a database of fragmentation data. In comparing a given fragmentation data to each other or to a database, the comparison manager may search for similar fragmentation data in the database, and allow the user to visually compare fragmentation data of peptides in the database. The comparison manager may also compare the subject mass spectra to the database of fragmentation data and identify, based on this comparison, characteristics for why the peptide may or may not be suitable for inclusion on the inclusion list of peptides containing the predetermined isotopic pattern as compared to those in the database.

In certain embodiments, the processing module of the system is further configured to include a collaboration manager configured to allow at least two different users (or mass spectrometers operating simultaneously) to jointly provide mass spectra data.

In using the subject systems, a user or computer automated to communicate with a mass spectrometer inputs data into the input module of the system. In certain embodiments, the system takes the provided information and generates an inclusion list of peptides containing the predetermined isotopic pattern. The report (e.g., inclusion list) is forwarded to the user, e.g., via the output display or is printed. In some instances, the report, and the data used to generate the report, is stored on the system in a suitable memory element, where the stored information may be accessed at a later time.

Systems of the invention further include an output manager that generates a report based on information received or generated. The output manager is a functional element that produces a report in response to receiving information and identifying a predetermined isotopic pattern of peptides in the mass spectra, determining the amino acid sequence of one or more of the peptides containing the predetermined isotopic pattern and determining the site of N-glycosylation on the protein based on the determined amino acid sequences.

Algorithm for identifying a predetermined isotopic pattern as outlined by the methods above is described in detail in Palaniappan et al. (*ACS Chem. Biol.* 2011, 6, 829-836), the method of which is herein incorporated by reference. Briefly, the algorithm analyzes peaks from a full-scan mass spectra and matches real data with simulated data generated by convoluting each predicted peptide's isotopic envelope with the pattern produced by a given tag. The algorithm received two inputs from the user: (1) a centroided mzXML data file and (2) a parameter file that includes the MW and isotopic pattern of the tag, charge states to be considered in the search, and weighting factors used to tune selectivity and sensitivity. The output included the m/z values and retention times of tagged species, which form an inclusion list for a subsequent directed LC-MS/MS analysis. First, the full-scan MS data were analyzed to identify putative isotopic signature matches for a given elemental composition. This step is a data dependent approximation of the contributions of non-halogens to the observed isotopic envelope, while allowing for the inevitable imperfections in MS data derived from complex protein samples. In the second step, the putative matches from the first step were analyzed using a graph-theoretic construct to reduce false positives. Peaks contributing to a putative pattern match are tracked as a function of LC elution time and number of charge states detected to add confidence that they derive from a real species.

Step 1. Identifying Putative Pattern Matches.

The algorithm takes a list of peaks from the full-scan mass spectrum and divides them into sets that were possibly isotopically related. Each of these sets were searched for the presence of a desired isotopic pattern as follows. First, each peak in the chosen data set was presumed to represent a peptide. Knowing the charge state and m/z for that hypothetical peptide, the program predicts its mass and estimated its elemental composition using the "averagine" model. The accuracy of the averagine method is confirmed by comparing the predicted elemental compositions of 20,000 human tryptic peptides (based on MW) with their actual elemental compositions, revealing a median deviation of less than 4%. From the estimated elemental composition, the isotopic pattern of the unlabeled hypothetical peptide was predicted. Then, the isotopic pattern of a chemical tag was convoluted with the predicted peptide's isotopic envelope, generating a reference pattern that was compared with the experimental data to determine a fitness score. The program also samples reference patterns that model untagged peptides and instrument noise. Additional reference patterns can be incorporated to account for common sources of false positives in a sample-dependent manner. Each reference pattern (R) was scaled in the intensity dimension to produce an optimal alignment with the data (D). This was accomplished by determining the scaling factor k by a binary search such that the sum of the squared difference (SSD) between each peak in the reference pattern (ri∈R) and its counterpart in the actual data set (d$_i$∈D) was minimized:

$$SSD = \sum_i (d_i - kr_i)^2$$

After intensity alignment, the score for the entire pattern was calculated as $$score = \prod_i f\left(\frac{|d_i - kr_i|}{\sigma\sqrt{2}}\right)$$

where σ is a measure of peak intensity variance and f is a scoring function for each peak that produced a value in the range [0,1]

$$f(x) = \max[erfc(x), \epsilon] \quad 0 < \epsilon \ll 1$$

in which erfc(x) is the complement of the Gaussian error function and the parameter was used to measure the tightness of the peak matching in the intensity dimension. The lower bound of ε was imposed on the function to reduce round-off errors in floating point arithmetic and to allow for robustness against contaminating peaks when used in a Bayesian system. In short, this system allowed for the identification of isotopic envelopes in actual MS data that do not perfectly match theoretically determined isotopic envelopes by virtue of overlapping peaks from other molecular species.

After scores of all patterns of interest were determined, the best match was found using a Bayesian approach:

$$P(pattern_i | data) = \frac{P(data | pattern_i)P(pattern_i)}{\sum_j P(data | pattern_j)P(pattern_j)}$$

$$= \frac{score(pattern_i | data)P(pattern_i)}{\sum_j score(pattern_j | data)P(pattern_j)}$$

where the P(pattern$_i$) terms were user-defined weighting factors that describe the probability that any peak in the data set was caused by a molecular species with the isotopic distribution described by pattern$_i$ and were determined experimentally. These weighting factors allowed us to increase the specificity of the program for a selected pattern, thereby eliminating false positives, or conversely, increasing the number of hits, though potentially at the cost of more false positives.

Step 2. Reducing False Positives with a Graph-Theoretic Approach.

The algorithm exploits two features of LC-MS data: peptides are often detected in multiple charge states and in several adjacent scans. To implement these features, a graph-theoretic approach was employed wherein each potential match was treated as a node in a graph. Edges were drawn between two nodes if the nodes could have come from the same molecular species and the nodes have sufficiently similar LC elution times. After edges were built, the graph was decomposed into disjoint subsets, where all nodes in a given subset could have been produced by the same peptide. Each of these subsets was then scored on a number of factors, including the number of nodes in the set and the number of unique charge states detected. Because matches that were made by chance are unlikely to score highly on these criteria, this process filters out false positive matches.

EXPERIMENTAL

The following examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

To illustrate methods of the present disclosure, N-glycosites on proteins from whole *Saccharomyces cerevisiae* lysates were mapped. Via preferential fragmentation of isotopically recoded glycopeptides, numerous N-glycosites within the yeast proteome were identified. As demonstrated below, methods of the present disclosure offer an enhanced level of confidence for mapping glycosylation sites that was not previously available to LC-MS/MS analyses because of the unique isotopic envelope of an isomix-containing peptide described herein.

Materials and Methods

Synthesis of N-Acetyl-D-Glucosamine (GlcNAc) Isotopologs

The synthesis of N-acetyl-D-glucosamine from D-glucosamine hydrochloride was performed in a single synthetic step as previously described (Zhu, et al. J Org Chem 71, 466-479, the method of which is herein incorporated by reference). Briefly, to a solution of the D-glucosamine hydrochloride salt (150 mg, 0.6 mmol) in water was added Dowex 200-400 mesh (OH—) anion-exchange resin and the pH was adjusted to 7.5. The resin was removed by filtration, yielding a D-glucosamine solution in 6 mL of water. To this solution was added $^{13}C_2$-sodium acetate (1.1 eq, Cambridge Isotope Laboratories) as a pre-dissolved solution in water and 2-ethoxy-1-ethoxycarbonyl-1,2-dihydroquinoline (1.1 eq) as a pre-dissolved solution in 10 mL ethanol. The total reaction volume was brought to 40 mL by addition of ethanol. The reaction was covered in foil and stirred for 36 h at RT. This reaction was repeated using 1-$^{13}C,^{15}N$-D glucosamine hydrochloride (Isotech) as the starting material. After ethanol evaporation under reduced pressure, the crude products were purified by silica gel chromatography using a 10:4:3 mixture of ethyl acetate:pyridine:water, dried, filtered, lyophilized and stored at −20° C.

Preparation of N-Acetyl-D-Glucosamine Isotopic Labeling Composition

Figure 1A:
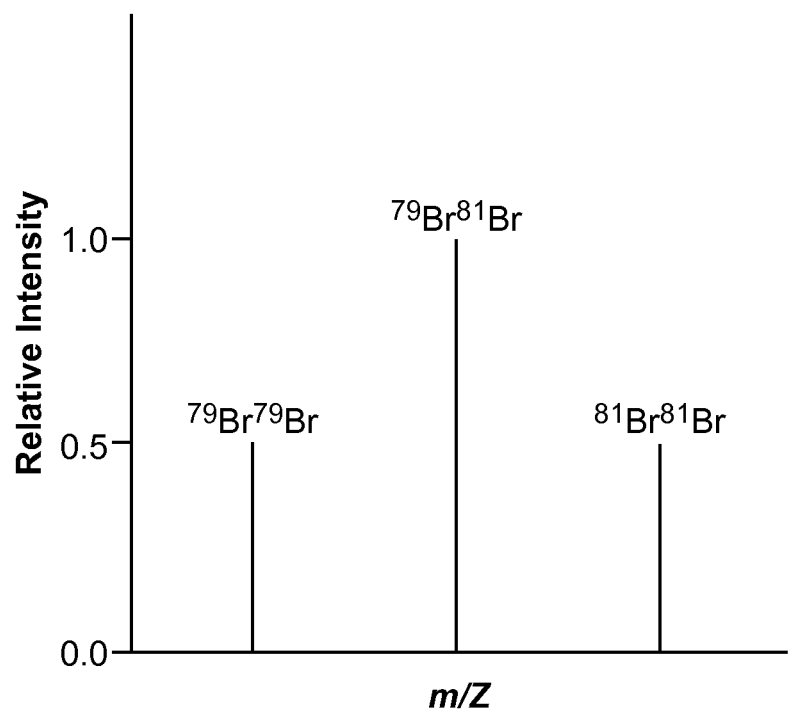
FIGS. 1a-c depict metabolic incorporation of a GlcNAc isotopic labeling composition (i.e, a GlcNAc isomix) into yeast N-glycans. (a) The dibromide triplet pattern, with a 1:2:1 relative peak intensity distribution, results from the natural abundances of $^{79}$Br and $^{81}$Br isotope pairings. (b) A three-component GlcNAc isomix mimics the 1:2:1 peak intensity distribution of dibromide by adjusting the concentration of each synthetically made isotopolog. (c) The GlcNAc isomix enters the gnaΔ yeast hexosamine biosynthetic pathway via a heterologous salvage pathway. The isomix signature is subsequently embedded into UDP-GlcNAc and any glycoconjugates that utilize UDP-GlcNAc in their construction, including the structurally conserved cores of N-glycans. Following cell lysis, proteolysis, partial enrichment of N-glycopeptides, and partial deglycosylation with Endo H, the distinctive isotopic signatures of N-glycopeptides are detected computationally using pattern-matching software. Masses of putative N-glycopeptide ions are granted fragmentation priority in subsequent LC-MS/MS analyses for N-glycosite identification. The N-glycan precursor illustrated here is composed of 2 core GlcNAc residues (squares), 9 mannose residues (white circles), and 3 glucose residues (gray circles).
Figure 1B:
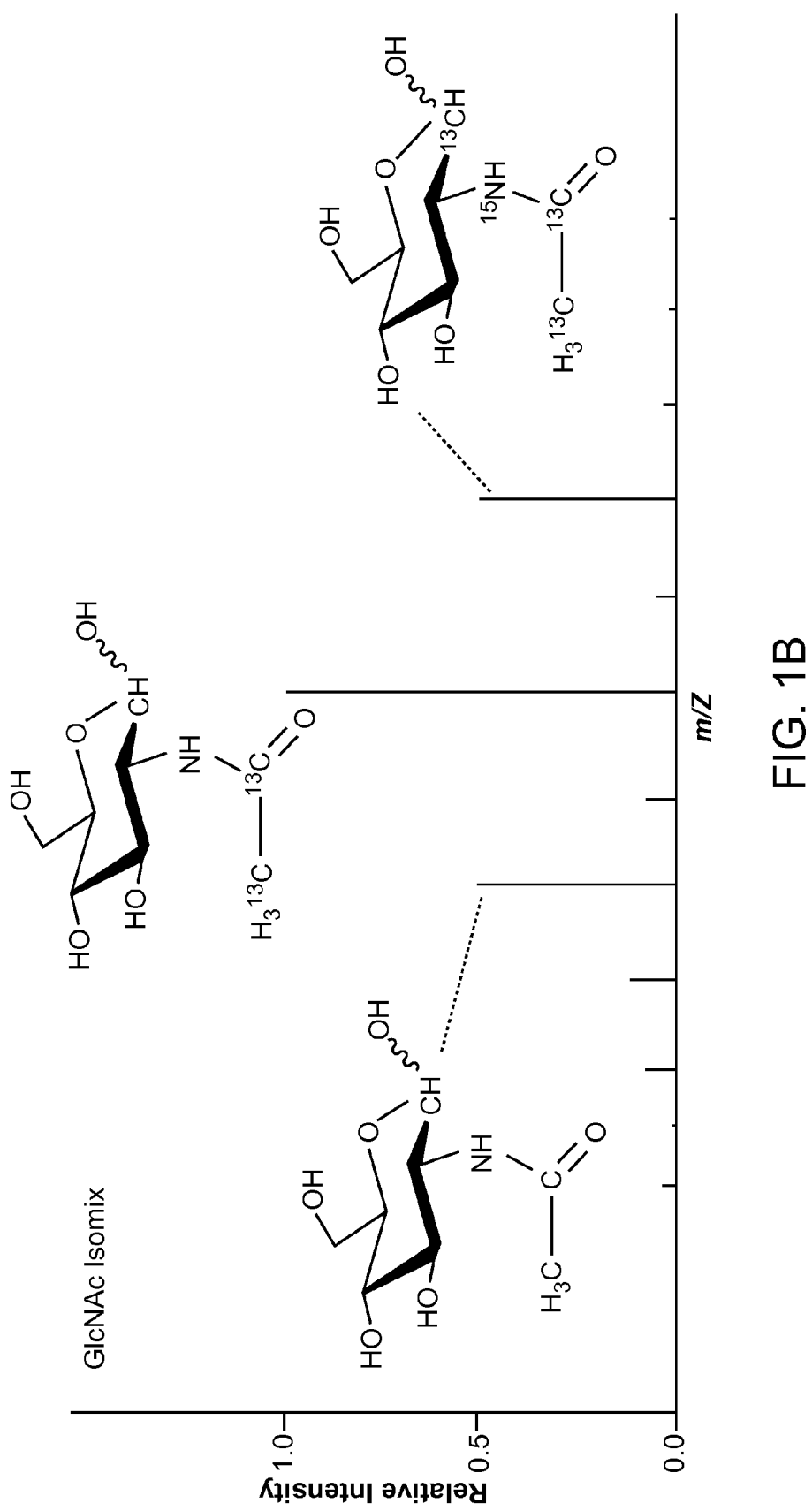

Stock solutions of 10 mM N-acetyl-D-glucosamine, N-[1,2-$^{13}C_2$]acetyl-D-glucosamine, and N-[1,2-$^{13}C_2$]-acetyl-D [1-$^{13}C$; $^{15}N$]glucosamine in water were prepared. The solutions were combined to produce a mixture of the GlcNAc isotopologs at a 1:2:1 molar ratio, respectively. The mixture was analyzed by direct infusion on a Thermo-Finnigan LTQ-XL mass spectrometer set to zoom scan, with the signal averaged over 20 scans. The isotopic ratios were then adjusted by the iterative addition of the desired isotopes until a near-perfect 1:2:1 peak intensity ratio was observed empirically (FIG. 1b). The isotopic labeling composition sample was lyophilized and stored at −20° C.

Cell Culture and Sample Preparation

Lysates from log-phase and stationary-phase GlcNAc isomix supplemented yeast cultures were prepared for mass spectrometry analysis by Filter-Aided Sample Preparation (FASP) methodology.

Cell Culture and Preparation of Lysates

Cultures of gnaIA *S. cerevisiae* (MATa ura3L yfl017c::KanMX4) were grown in CSM (MP Biomedicals) with 2% dextrose as the carbon source and a 100 µM GlcNAc isomix supplement at 30° C. until the OD600=1 for mid-log phase or the OD600=8 for stationary phase harvests. A 100 µM regular GlcNAc supplement was used for negative controls. Cells were pelleted by centrifugation and flash-frozen in $LN_2$ and stored at −80° C. Whole-cell lysates were prepared from 2 g aliquots of log- and stationary-phase cell pellets, each resuspended in 20 mL of lysis buffer (PBS, 1% w/v RAPIGEST™ surfactant, 1 mM dithiothreitol). RAPIGEST™, an acid-labile surfactant, was prepared following the synthesis reported in U.S. Pat. No. 7,229,539, the method of which is herein incorporated by reference. Cells were lysed with 10 passes through an Avestin EMULSIFLEX™-C3 homogenizer set to a maximum pressure of 30 Kpsi and crude extracts were clarified in a Sorvall SS-34 rotor spun at 19.5 Krpm for 30 min at 4° C. Clarified lysates were filtered through a 0.2 µm STERIFLIP™ filter (Millipore) and total protein concentrations were measured colorimetrically using the DC assay (BioRad). Lysates were aliquoted into small portions, flash frozen in LN2, and stored at −80° C. until needed.

FASP Processing of Lysates

Milligram-scale aliquots of log-phase and stationary-phase lysates were prepared for MS analysis via a modified version of the previously described Filter-Aided Sample Preparation (FASP) methodology. Lysates (1.2 mg of total protein/sample) were diluted to a total volume of 2 mL with freshly prepared buffered urea (7 M urea in 100 mM Tris pH 7.4 and 2.5 mM dithiothreitol). Samples were loaded into 30-KDa NMWCO AMICON™ Ultra centrifugal filtration devices (Millipore), spin-concentrated, and adjusted to a final volume of 600 µL with buffered urea. Cysteine residues were alkylated by addition of 50 L of freshly-prepared 500 mM iodoacetamide followed by incubation for 1 hour at room temperature in the dark. Samples were sequentially washed and spin-concentrated with 1 mL of buffered urea (two washes) followed by PBS with 2.5 mM dithiothreitol (three washes). Final volumes were adjusted to 1 mL/sample with PBS.

Tryptic digests were obtained by addition of 5 µg of sequencing-grade trypsin (Promega)/sample and incubation for 12 hours at 37° C. Chymotryptic digests were performed by addition of 5 µg of sequencing-grade chymotrypsin (Promega)/sample followed by incubation for 12 hours at 25° C. Peptides were recovered by centrifugation through 30-KDa NMWCO filters. Peptide samples were diluted to a total volume of approximately 2 mL with 2×ConA binding buffer (40 mM Tris pH 7.4, 1 M NaCl, 2 mM CaCl2, 2 mM MnCl2). A 5 mg/mL stock solution of *C. ensiformis* ConA (Sigma) was prepared in 1×ConA binding buffer, and 2.5 mg of ConA were added to the digested peptides from each sample followed by incubation for 1 hour at room temperature. The lectin-peptide mixtures were transferred to fresh 30-KDa NMWCO AMICON™ ultra filters that had been pre-washed with 1×ConA binding buffer. ConA-bound peptides were washed by spin-concentration and diluted 4× with 1 mL of EndoH buffer (50 mM sodium citrate pH 5.3, 0.5 M sodium chloride, 1 mM calcium chloride, 1 mM manganese chloride). ConA-bound peptides were incubated with 5 µL (5000 units) of EndoHf (New England Biolabs) for 3 hours at 37° C. Deglycosylated peptides were collected via centrifugation into siliconized eppendorf tubes. Samples were briefly acidified with trifluoroacetic acid to pH=2 to hydrolyze any remaining detergent. Insoluble debris was removed by centrifugation. Samples were desalted using SEP-PAK™ C18 cartridges (Waters) and solvent was removed by speed-vac before storing at −20° C. until mass spectrometry analysis.

Mass Spectrometric Analysis

Prior to mass spectrometry analysis, samples were resuspended in 50 µL of water and 2.5-5 µL aliquots were subjected to reverse-phase liquid chromatography with an Agilent 1200 liquid chromatography system connected in-line to a LTQ ORBITRAP™ XL hybrid mass spectrometer. External mass calibration was performed prior to analysis. A binary solvent system consisting of buffer A (0.1% formic acid in water (v/v)) and buffer B (0.1% formic acid in acetonitrile (v/v)) was employed. The mass spectrometer was outfitted with a nanospray ionization source. Liquid chromatography was performed using a 100-µm fritted capillary pre-column self-packed with 1 cm of 5 µm, 200 Å Magic C18AQ resin (Michrom Bioresources) followed by a 100-µm fused silica capillary (Polymicro Technologies) self-packed with 15 cm of 5 µm, 100 Å Magic C18AQ resin (Michrom Bioresources). After sample injection and a 20 minute loading step in 2% buffer B, peptides were eluted using a gradient from 7% to 35% buffer B over 150 min, followed by a washing step in 99% buffer B for 20 minutes. A solvent split was used to maintain a flow rate of 400 nL min-1 at the column tip.

Samples were subjected to the inclusion-list driven targeted acquisition method, described above. First, full-scan mass spectra were collected in positive ion mode over the m/z scan range of 400 to 1,700 or 1,800 using the ORBITRAP™ mass analyzer in profile mode at a resolution of 60,000 (at 400 m/z). Noise reduction and peak detection were performed using software developed in-house making use of a continuous wavelet transform. The centroided mzXML files were then pattern searched for recoded mass envelopes. The output was an inclusion list that contained the m/z value (M+2 ion in the labeled peptide's isotopic envelope) and a retention time window (±1.5 min, empirically determined) for each labeled peptide. The same sample, stored at 4° C., was then reanalyzed with identical chromatographic conditions using an inclusion-list driven selection of precursor ions for fragmentation. In relatively rare instances we observed a chromatographic anomaly causing substantially shifted peptide elution profiles. In these cases the experiment was repeated. For each full-scan mass spectrum up to eight CID fragmentation events were performed in the linear ion trap. Dynamic exclusion and charge state screening were enabled to reject ions with an unknown or +1 charge state. An isolation window (IW) of 2 or 4 Da, a minimum threshold of 500 ion counts, and activation energy of 35 were used when triggering a fragmentation event.

Database Searching

Peptide identities were obtained using the SEQUEST search algorithm (Eng, et al. J. Am. Chem. Soc. Mass. Spec. 5, 976-989, the method of which is herein incorporated by reference) within Proteome Discoverer 1.2 (Thermo-Fisher). CID spectra were searched against the sequence database generated from all systematically named *S. cerevisiae* ORFs (downloaded March 2011) (Chemy, et al. Nature 387, 67-73, the method of which is herein incorporated by reference) augmented with sequences from the common repository of adventitious proteins (cRAP, from The Global Proteome Machine Organization, downloaded March, 2011) and the Ngt1 (*C. albicans*) and NAGK (*H. sapiens*) protein sequences, totaling 6739 entries. Indexed databases for tryptic and chymotryptic digests were created allowing for two missed cleavages, one non-enzymatic terminus, one fixed modification (cysteine carboxyamidomethylation, +57.021) and the following variable modifications: methionine oxidation (+15.995) and Asn GlcNAcylation (only the M+2 isotopolog, +205.086 Da). Precursor ion tolerance was set to 10 ppm and CID fragment tolerance was set to 0.8 Da. The criteria used for filtering search results included using SEQUEST score function (XCorr) cutoffs assigned by a 5% maximum false discovery rate (FDR) obtained from decoy database searches (using reversed sequences from each of the 6739 entries in the database), an 8 ppm maximum allowed precursor ion mass deviation, and a 40 amino acid maximum allowed peptide length. Approximately 70% of the peptides were identified within a 1% maximum FDR. All precursor ion and fragmentation spectra were visually inspected for the predetermined isotopic pattern, described above. Precursor ion isotopic labeling composition patterns were also visually verified in the corresponding full-scan datasets. In cases where the isotopic labeling composition pattern was identifiable in the low-resolution fragmentation spectra, this additional information was used to verify correct glycosite assignment, especially in peptides containing multiple Asn residues. For datasets collected with an IW of 2, full-scan only dataset were used (i.e., the LC-MS run which was subjected to pattern searching) to confirm the predetermined isoptoic pattern. In cases where multiple peptide sequences covered a single glycosite, a representative peptide sequence was selected based on CID spectral quality. Factors such as protein biological function and the presence of a canonical N-glycosylation consensus motif (N-X-S/T) were not used as criteria for accepting or rejecting peptides. Instances of ambiguous post-translational modification assignment within a peptide were resolved by manual inspection of fragment envelopes, as necessary.

Results

Metabolic Recoding of N-Glycan Cores

Due to the relative ease with which certain *S. cerevisiae* biosynthetic pathways can be manipulated, we chose to metabolically install an unnatural, dibromide-like isotopic signature into glycans. Universal isotopic recoding of N-glycans requires metabolic replacement of a conserved sugar residue found in all such structures with a mixture of isotopologs. All eukaryotic N-glycans possess a conserved GlcNAcβ1,4GlcNAc disaccharide at the peptide-proximal position, thus a GlcNAc isomix can potentially label all N-glycans in the cell's glycoproteome. However, to retain the isotopic ratio during metabolism, the GlcNAc isomix must be converted without isotopic dilution to the key metabolic intermediate uridine diphosphate-GlcNAc (UDP-GlcNAc), the donor nucleotide-sugar used in construction of N-glycan cores. Specifically, cytosolic UDP-GlcNAc serves as the donor substrate for Alg7p in the biosynthesis of GlcNAc-diphosphodolichol; the GlcNAc residue in this precursor is ultimately covalently linked to Asn in the process of N-glycosylation. Thus, control over a cell's uridine diphosphate-GlcNAc (UDP-GlcNAc) pool is critical for execution of the isomix method. We recently generated a *S. cerevisiae* strain that depends on an engineered salvage pathway for procuring precursors of UDP-GlcNAc. The gnalA yeast strain lacks the ability to perform de novo UDP-GlcNAc biosynthesis and instead generates UDP-GlcNAc exclusively by salvaging GlcNAc added to the culture media. In previous work, we exploited this yeast strain to achieve high-efficiency replacement of GlcNAc residues with unnatural GlcNAc analogs, which are alternative substrates for the engineered salvage pathway.

Figure 1C:
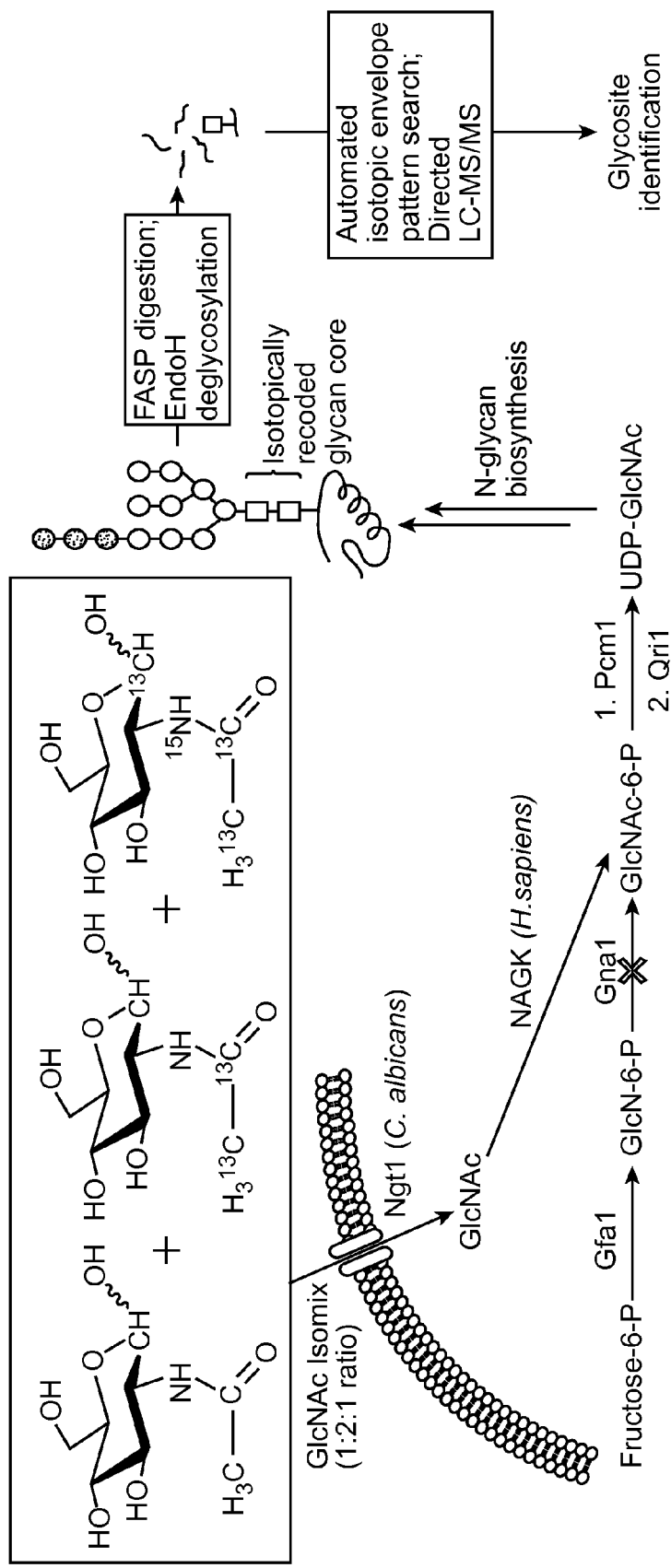

In the examples described herein, cultured gnalΔ yeast with a GlcNAc isomix designed to emulate the isotopic signature of two bromine atoms. As shown in FIG. 1a, the dibromide pattern is a symmetrical triplet, with major peaks at M, M+2 and M+4 at a relative intensity of 1:2:1, due to the relative abundances of the $^{79}Br_2$, $^{79}Br^{81}Br$, and $^{81}Br_2$ isotopic pairings. To replicate this pattern, a three-part isomix consisting of N-acetyl-D-glucosamine, N-[1,2-$^{13}C_2$]acetyl-D-glucosamine, and N-[1,2-$^{13}C_2$]acetyl-D-[1-$^{13}C$;$^{15}N$]glucosamine, mixed in a 1:2:1 molar ratio (FIG. 1b), was prepared and added to the gnalA yeast culture medium (FIG. 1c). The isomix is internalized via the GlcNAc-specific transporter Ngt1 borrowed from *C. albicans*, and cytosolic GlcNAc is subsequently phosphorylated by the heterologously expressed human kinase NAGK. The resulting GlcNAc-6-phosphate isomix is converted to a UDP-GlcNAc isomix and subsequently installed into N-glycan cores by endogenous yeast machinery.

Directed Proteomic Analysis of N-Glycosylated Peptides

Samples for LC-MS/MS analysis were generated from lysates of gnalΔ *S. cerevisiae* cultures grown to both mid-log and stationary phases in chemically defined, minimal medium. Tryptic and chymotryptic peptides were prepared from the lysates using a modified version of Filter Aided Sample Preparation, described above. During this process, mannose-containing glycopeptides were partially enriched by binding to the lectin concanavalin A (Con A) and N-glycans were truncated to a single GlcNAc residue with the glycosidase Endo H. To achieve sufficient resolution for isotopic envelope pattern matching, peptides were analyzed on a Thermo-Finnigan LTQ ORBITRAP™ XL mass spectrometer.

Figure 2A:
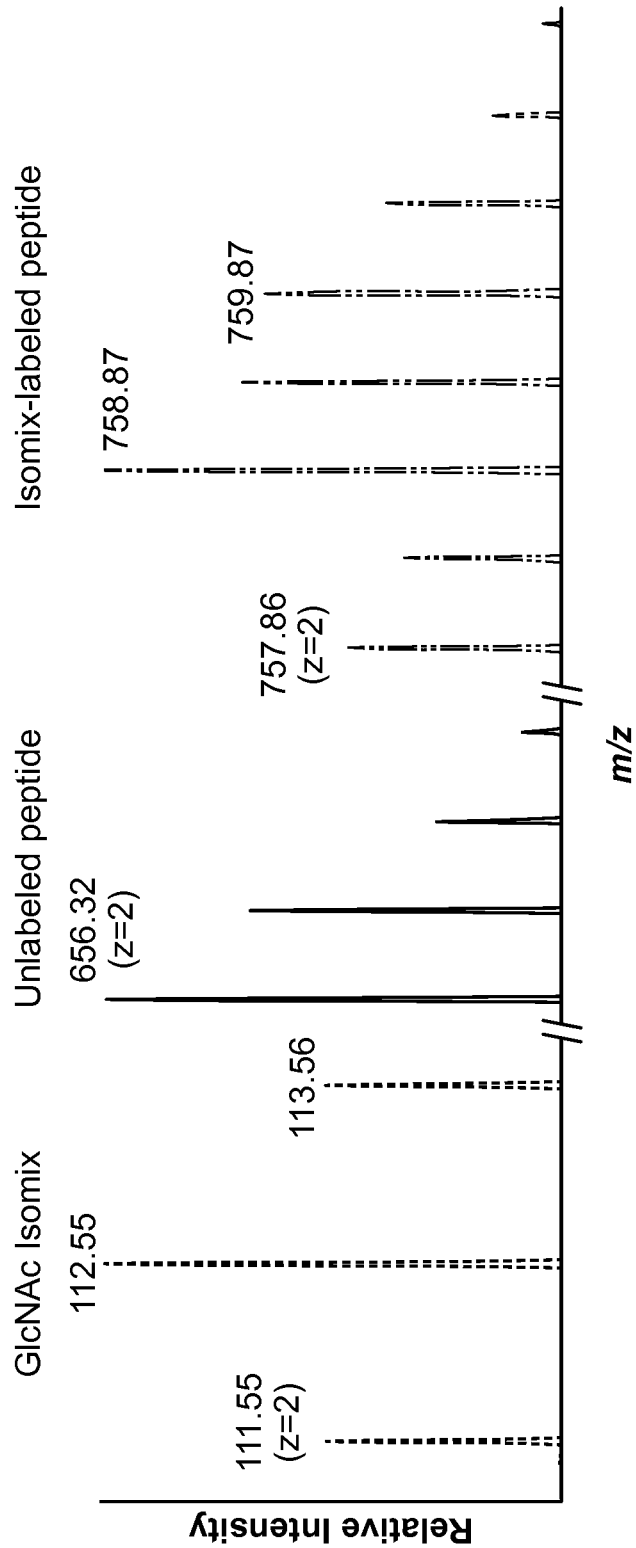
FIGS. 2a-c show the perturbing effect of a GlcNAc isomix on a peptide's isotopic envelope according to certain embodiments of the present disclosure. (a) Simulated isotopic envelopes (z=2) for the GlcNAc isomix, an unlabeled peptide from the glycoprotein Ygp1 (NSSSALNITELY (SEQ ID NO:1)), and the same peptide labeled with the GlcNAc isomix. The isotopically recoded peptide has a visually distinctive distribution of peak intensities. (b) In experimental LC-MS data, the isotopic envelope of the precursor ion corresponding to the NSSSALnITELY (SEQ ID NO:1) glycopeptide is shown. The modified Asn residue is in lowercase.

Recoded peptide envelopes bear distinctive peak intensity distributions, as illustrated in the simulated isotopic envelopes shown in FIG. 2a. The envelope of an isotopic labeling composition glycopeptide reflects the peptide's intrinsic envelope convolved with that of the GlcNAc isomix. The unique pattern resulting from this convolution serves as the basis for detecting putative glycopeptides in complex samples. Experimentally observed isomix-containing glycopeptide envelopes are exemplified in FIG. 2b matching simulations (FIG. 2a). Characteristic isotopic labeling composition pattern in yeast peptides subjected to LC-MS analysis were searched using the computer algorithm described above (Palaniappan, et al. ACS Chem. Biol. 6, 829-836, the method of which is herein incorporated by reference). In general, 4,000-5,000 candidate glycopeptide ions (in charge states z=1 to z=5) per sample were detected. In certain instances, the peptide inclusion list contained redundancy. For example, several legitimate, isotopic label-containing glycopeptides were observed in multiple charge states between z=1 and z=5. In some instances, more than one peptide covering the same glycosite was observed. Regardless, the m/z values and retention times of putative glycopeptide ions bearing the predetermined isotopic pattern were used to construct a time-resolved inclusion list of peptides for targeted fragmentation. Even with the inclusion of a lectin-based glycopeptide enrichment step during sample preparation, the overwhelming majority of high-intensity ions in our samples appeared to be unglycosylated, as indicated by visual and computational inspection of their isotopic envelopes.

Duplicate, back-to-back injections for targeted fragmentation of glycopeptides was performed. The first injection was used exclusively to search for GlcNAc isotopic patterns in LC-MS data to identify likely glycopeptide ions and inventory them into an inclusion list. In the subsequent injection, candidate glycopeptide ions were subjected to fragmentation by collision induced dissociation (CID) only if the ion abundance exceeded a defined threshold and the ions appeared in the correct retention time window. The bond between Asn and GlcNAc is resistant to standard CID conditions used to fragment the peptide backbone.

Figure 2B:
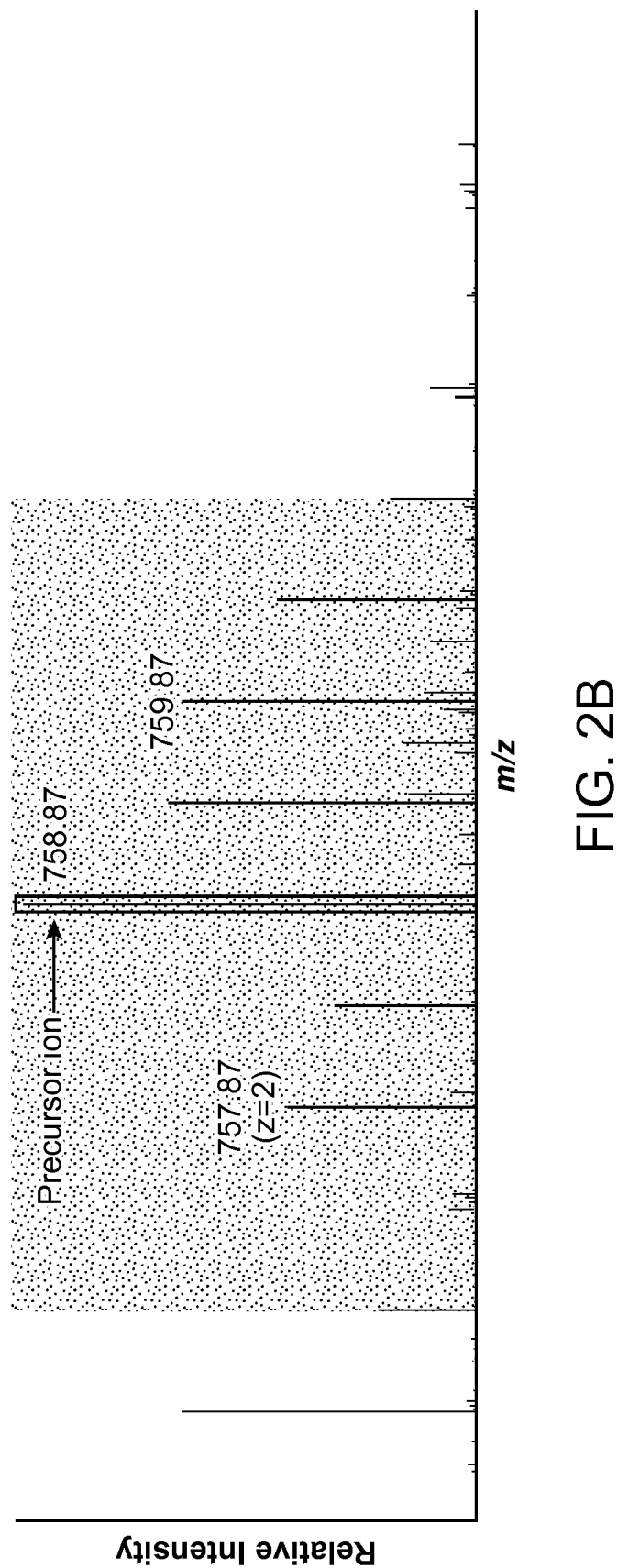
Figure 2C:
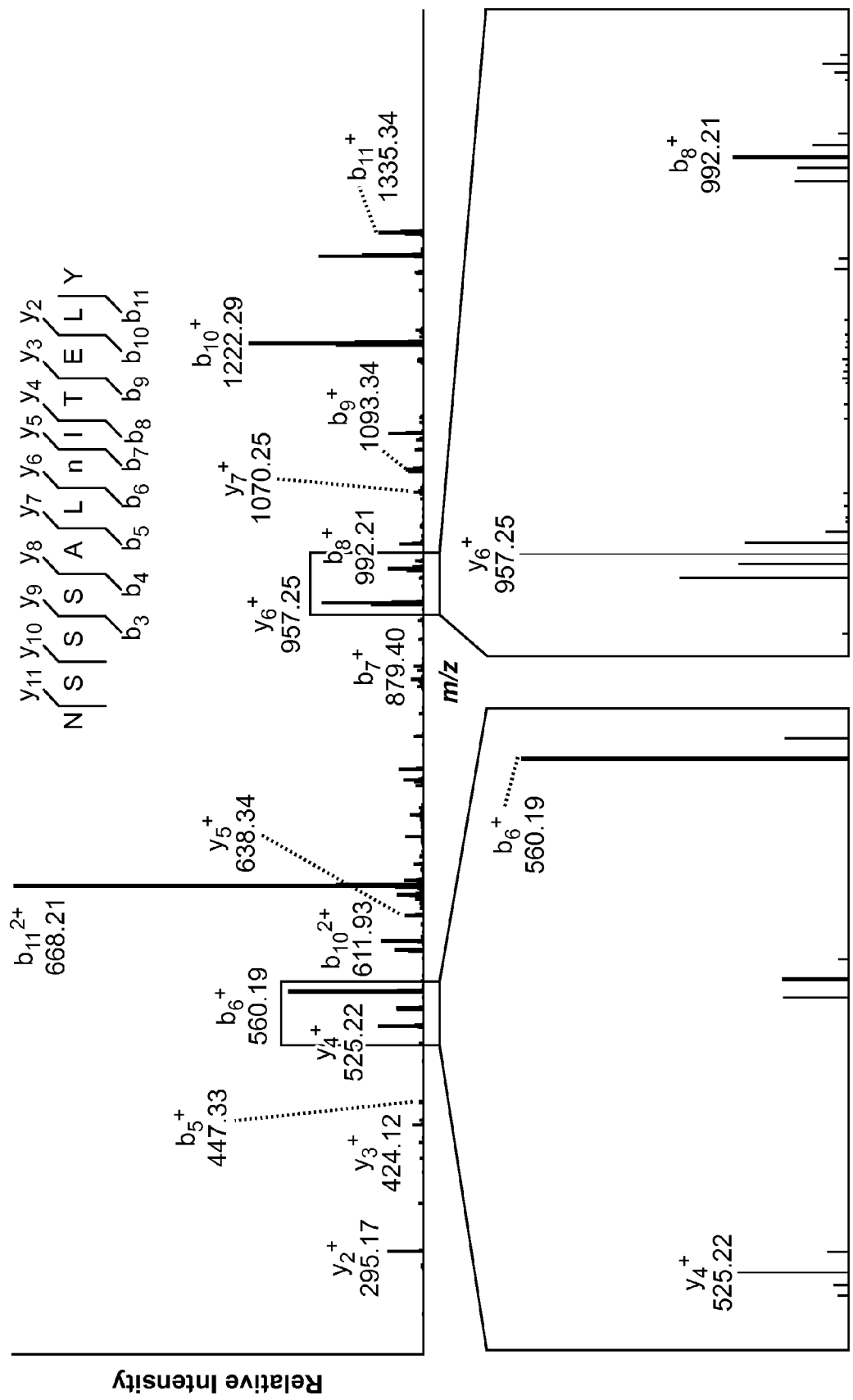
Figure 6:
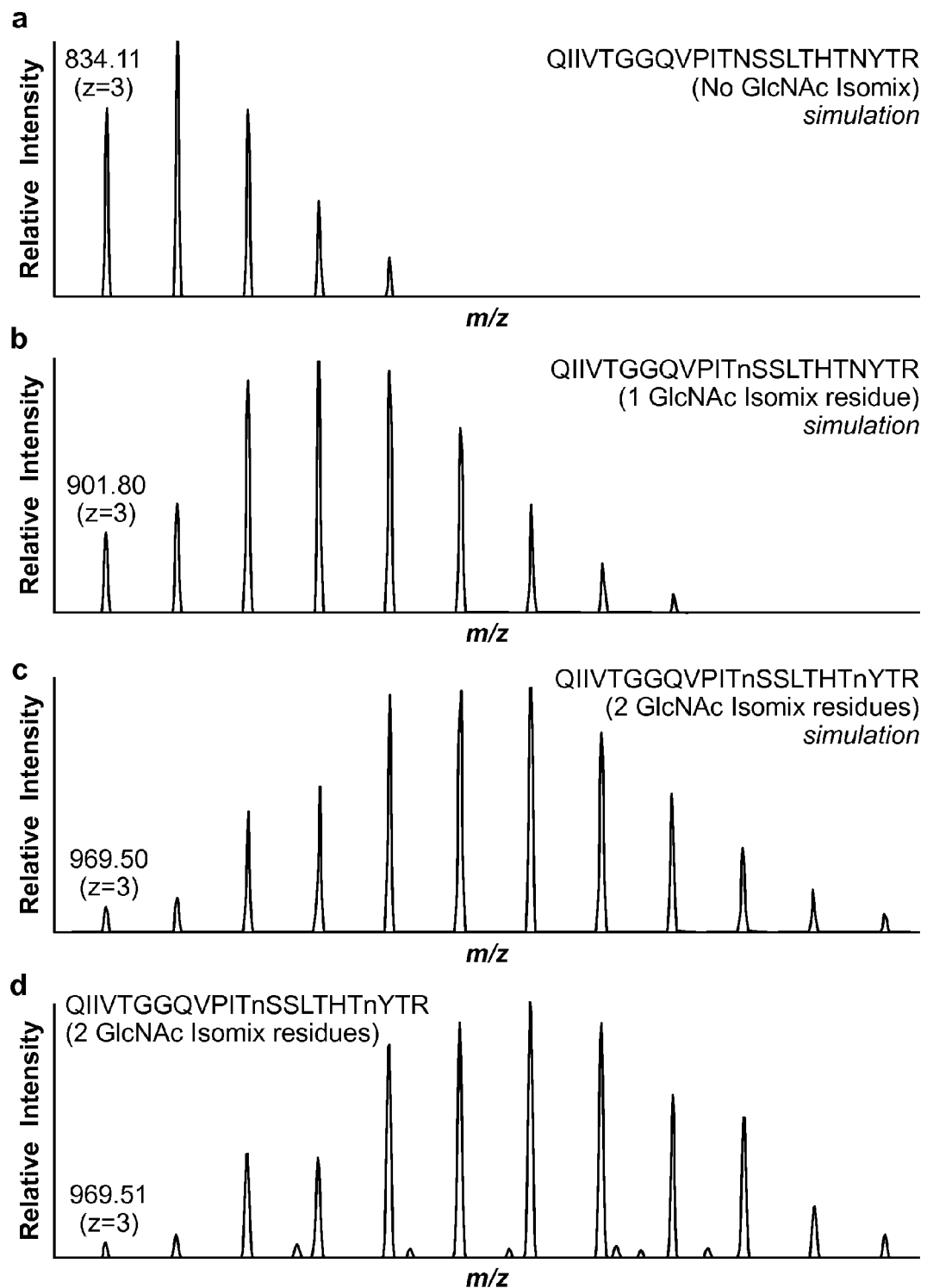

Ions bearing the predetermined isotopic pattern were subjected to CID fragmentation in order to determine peptide identity (i.e., amino acid sequence) and verify N-glycosylation. Ions selected for fragmentation were isolated in either a narrow (2 Da) or broad (4 Da) isolation window (IW). While a broad IW covers most peaks in an isotopic labeling composition glycopeptide envelope (FIG. 2b), it has the disadvantage of potentially including unrelated ions in the fragmentation spectrum. Conversely, the use of narrow IWs could yield higher quality fragmentation spectra because fewer unrelated ions will be isolated. However, in practice, the use of a 4 Da IW results in the highest number of MS/MS identifications despite the potential decrease in the precursor ion fraction isolated. Indeed, we observed no detrimental effects on peptide assignments in datasets collected using 4 Da verses 2 Da IWs. Instead, the use of a broad IW on ions bearing the predetermined isotopic pattern often provided additional information in the fragmentation spectra that was critical to resolving glycosite positional ambiguity. The broad IW was particularly useful for glycosite assignment in the case of peptides containing more than one Asn residue. As illustrated in FIGS. 2b and 2c, when the full isotopic envelope of a candidate glycopeptide was isolated for fragmentation using a broad IW, the predetermined isotopic pattern in all peptide fragments bearing the GlcNAc labeling composition modification was preserved. In contrast, unglycosylated fragments yielded unperturbed mass envelopes. This information was used to resolve cases of ambiguous glycosite assignments that resulted from automated database search engines. In some cases, doubly glycosylated peptides were observed; the presence of two N-glycosites on one peptide introduced a doubly convolved isomix signature resulting in a widened isotopic envelope with a distinctive "stair-step" pattern in peak intensities (FIG. 6).

Isomix-Directed Fragmentation Facilitates High-Confidence N-Glycosite Identification.

A unified list of high-confidence N-glycosites in the yeast proteome (summarized in Table 1, provided in FIG. 9) was compiled based on the results obtained. Table 1 reflects a combination of results from multiple experiments, conducted with trypsinized and chymotrypsinized samples obtained from both stationary and mid-log phase cultures. A list of the observed tryptic and chymotryptic peptides containing these glycosites and corresponding statistical indicators of quality are included in FIG. 9 which depicts Table 1. A total of 133 N-glycosites were detected, 12 of which were previously reported in the Uniprot Knowledgebase. 121 novel sites distributed over 52 proteins were determined. 50% of the proteins in Table 1, highlighted indicated in bold, have been biochemically validated as N-glycosylated. Proteins were considered biochemically validated if they had previously mapped N-glycosites or if there was experimental observation of a gel shift following enzymatic deglycosylation. The above results suggest that the gnal∆ S. cerevisiae likely share similar N-glycosite occupancy patterns with the BY4743 strain from which the gnal∆ haploid was derived.

For comparative purposes, the above samples were subjected to traditional intensity-driven data-dependent LC-MS/MS, in which the ten most intense ions in each full scan mass spectrum were selected for CID fragmentation. Significantly, the intensity-dependent analyses typically identified approximately 60% of the glycosites found via isotopic labeling composition-directed fragmentation. For instance, in the case of trypsinized lysate prepared from a stationary-phase culture, 52 unique glycosites spanning 25 proteins were identified using directed fragmentation. The same sample, subjected to data-dependent fragmentation, yielded only 30 N-glycosites in 16 proteins and contained extensive site overlap with the directed dataset. This difference illustrates the advantages of the methods described herein for proteomic analyses.

Glycoproteins identified in this study were categorized by the manually curated ontological annotations maintained by the *Saccharomyces* Genome Database. An analysis of cellular localization (FIG. 3a) reveals that the majority of the N-glycoproteins identified in Table 1 typically reside in the yeast ER, plasma membrane, vacuole, and cell wall. Several proteins localize to substructures within these organelles, especially those involved with cytokinesis and cellular budding. While many of the identified glycoproteins lack known molecular functions, Table 1 was highly represented by peptidases, glycosidases, and glycosyltransferases (FIG. 3b). With respect to biological function, highly represented categories include vacuolar proteases and proteins involved in cell wall construction, reshaping, and maintenance (FIG. 3c). Several ER- and golgi-resident proteins participating in the processes of N- and O-linked glycosylation were also detected. Overall, the ontological distribution of glycoproteins reported here is consistent with our expectations for N-glycoproteins in yeast.

In addition to the ontological consistency for the list of N-glycoproteins, no plausible cases in which the N-glycan modification was present outside the canonical N-X-S/T motif were detected. While non-canonical N-glycosites have been reported in higher eukaryotes, it is possible that the acceptor substrate promiscuity of the oligosaccharyl transferase (OST) complex—which catalyzes the N-glycosylation modification—differs amongst species.

A plot of the relative residue frequencies for the 133 occupied glycosites mapped here reveals a strong, 71% versus 29% preference for Thr over Ser within the canonical motif (FIG. 4), consistent with N-glycosites mapped in other eukaryotic proteins by non-proteomic methods. Additionally, positions surrounding the motif are dominated by hydroxylated and small hydrophobic residues, consistent with expectations for solvent-exposed, loop regions of proteins. Charged residues, especially aspartate, are present in slightly higher frequency on the C-terminal side of the sequon, but not at the −2 position as observed in the case of bacterial N-glycosites. Collectively, these data reveal a typical acceptor substrate sequence for the yeast OST.

As demonstrated above, a metabolically embedded isotopic signature, emulating the perturbing effects of a dibrominated chemical tag, can serve as the basis for targeted proteomic analysis of a class of post-translational modifications. As discussed above, methods of the present disclosure allows the ions selected for fragmentation that need not be among the most intense in the sample. In addition, the produced recoded isotopic mass envelopes contain a predetermined isotopic pattern which is easily detected, indicating whether or not fragmentation spectra have been correctly assigned to a peptide. Systematically mapping N-glycosylation sites in *S. cerevisiae* provides a wealth of information pertaining to native glycoprotein structure and topology. It is well known that the mere presence of a standard N-X-S/T sequon is not sufficient to guarantee glycan attachment to a nascent polypeptide. A number of extenuating factors, ranging from local protein structure to nutrient availability, ultimately determine which sequons are glycosylated. In the case of soluble proteins, fully or partially occupied glycosites are an excellent indicator of sequon surface accessibility. In the case of integral membrane proteins (IMPs), occupied glycosites confirm that a given Asn is ER-lumenal upon translation and can be used to confirm or reject IMP topological predictions. In the data presented herein, 25 glycosylated IMPs were detected and in all cases the occupied glycosites confirm TMHMM topology predictions of lumenal versus extracellular domains. Additionally, glycosite mapping is a prerequisite for quantitative, comparative analysis of glycan occupancy.

Figure 7:
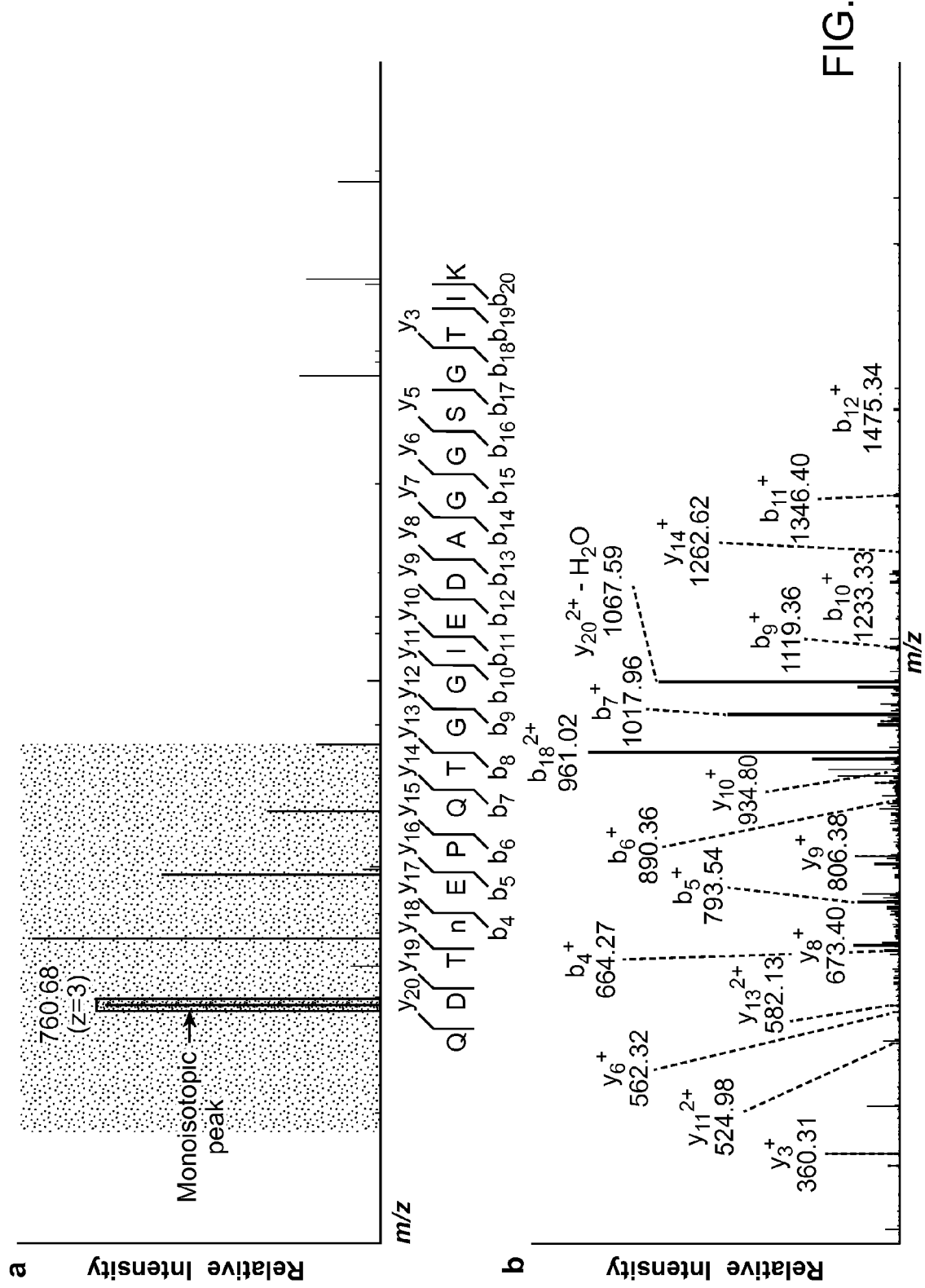

As illustrated in FIG. 2, precursor and fragment ions corresponding to recoded peptides bear a unique isotopic pattern that could be used as a basis for accepting or rejecting a computationally-assigned spectral match. Indeed, several peptides in the data were computationally matched to peptides based on favorable statistical indicators, such as high SEQUEST XCorr values, but were ultimately rejected because they lacked the characteristic isomix signature in their isotopic envelopes. As illustrated in FIG. 7, a peptide isolated for CID fragmentation via data-dependent selection was assigned to a GlcNAc-containing peptide from the cytosolic kinase Akl1 with high confidence. However, manual inspection of the precursor ion's isotopic envelope revealed no evidence of the predetermined isotopic pattern, casting doubt on the assignment. The lack of a standard N-X-S/T sequon in this peptide and the cytosolic location of Akl1 are also consistent with spectral misassignment. Thus, isotopic recoding of PTMs can serve as a valuable tool for rejecting incorrect spectral assignments that would otherwise pass undetected into LC-MS/MS hit lists.

By using glycans containing a predetermined isotopic pattern as described above, fragmentation priority was placed on glycopeptide ions regardless of their relative intensities to other ions in the sample. As a result, rigorous sample enrichment for N-glycopeptides was not necessary. However, enrichment with ConA may allow for the presence of many high-abundance, non-glycopeptides in our sample, suppressing ionization and the successful detection and fragmentation of low-abundance and poorly ionizing glycopeptides within the yeast proteome.

The concept of isotopically recoding PTMs for targeted LC-MS/MS analysis can be extended well beyond N-glycosite mapping. By utilizing endogenous or engineered salvage pathways, unnatural isotopic signatures could be metabolically installed into a variety of PTMs. The relative malleability of glycan biosynthetic pathways, along with an extensive assortment of commercially available stable monosaccharide isotopologs, makes glycan-based PTMs particularly well suited for isotopic recoding. The predetermined isotopic pattern may be any convenient pattern, such as a 1:1, 1:2, 1:3, 1:4, 1:2:1, 1:3:1, among others as described above. A variety of isotopic labeling compounds can be used to impart sufficient perturbation to a peptide's isotopic envelope to allow for successful targeted LC-MS/MS analyses.

As noted above, the illustrated approach of isotopic recoding for targeted proteomics is not limited to the genetically modified S. cerevisiae strain. While metabolic introduction of an unnatural isotopic signature is demonstrated above, similar perturbations of isotopic envelopes can also be obtained via chemospecific or enzymatic labeling of specific PTMs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended claims.

What is claimed is:

1. A method for identifying a site of N-glycosylation on a protein, the method comprising:
   incubating a eukaryotic cell with an isotopic labeling composition comprising two or more different isotopic labels to obtain an isotopically labeled sample of N-glycosylated proteins;
   enzymatically producing peptides from the isotopically labeled sample of N-glycosylated proteins to obtain an enzymatically treated sample of isotopically labeled peptides;
   subjecting the enzymatically treated sample of isotopically labeled peptides to liquid-chromatography-tandem mass spectrometry;
   identifying a predetermined isotopic pattern of the enzymatically treated, isotopically labeled sample of peptides in a mass spectrum at one or more retention times;
   determining an amino acid sequence of an isotopically labeled peptide present at the one or more retention times;
   and identifying the site of N-glycosylation on the isotopically labeled protein based on the determined amino acid sequence.

2. The method according to claim 1, wherein the isotopic labels are N-acetyl-D-glucosamine, N-[1,2-$^{13}C_2$]acetyl-D-glucosamine and N-[1,2-$^{13}C_2$]acetyl-D-[1-$^{13}C$;$^{15}N$]glucosamine.

3. The method according to claim 2, wherein the isotopic labeling composition comprises a stoichiometric ratio of 1:2:1 of N-acetyl-D-glucosamine, N-[1,2-$^{13}C_2$]acetyl-D-glucosamine and N-[1,2-$^{13}C_2$]acetyl-D-[1-$^{13}C$;$^{15}N$]glucosamine.

4. The method according to claim 1, wherein enzymatically producing peptides comprises contacting the N-glycosylated proteins with trypsin, Lys-C, Arg-N or chymotrypsin.

5. The method according to claim 1, wherein identifying a predetermined isotopic pattern comprises identifying a 1:2:1 peak intensity ratio in the mass spectrum.

6. The method according to claim 1, wherein the method further comprises generating an inclusion list of peptides having a mass spectrum that contains the predetermined isotopic pattern.

7. The method according to claim 6, wherein the method further comprises determining an amino acid sequence for each of the peptides on the inclusion list.

8. A method for detecting a low-abundance protein in a biological sample, the method comprising:
   incubating a eukaryotic cell with an isotopic labeling composition comprising two or more different isotopic labels;
   subjecting an isotopically labeled biological sample obtained from the eukaryotic cell to liquid-chromatography-tandem mass spectrometry; and
   identifying a predetermined isotopic pattern in a mass spectrum at one or more retention times to thereby detect the presence of the low-abundance protein in the biological sample.

9. The method according to claim 8, wherein the isotopic labels are N-acetyl-D-glucosamine, N-[1,2-$^{13}C_2$]acetyl-D-glucosamine and N-[1,2-$^{13}C_2$]acetyl-D-[1-$^{13}C$;$^{15}N$]glucosamine.

10. The method according to claim 9, wherein the isotopic labeling composition comprises a stoichiometric ratio of 1:2:1 of N-acetyl-D-glucosamine, N-[1,2-$^{13}C_2$]acetyl-D-glucosamine and N-[1,2-$^{13}C_2$]acetyl-D-[1-$^{13}C$;$^{15}N$]glucosamine.

11. The method according to claim 8, wherein the isotopically labeled biological sample obtained from the eukaryotic cell comprises N-glycosylated proteins.

12. The method according to claim 11, wherein the N-glycosylated proteins comprise the isotopic labels.

13. The method according to claim 11, wherein the method further comprises producing peptides from the N-glycosylated proteins.

14. The method according to claim 13, wherein producing peptides comprises contacting the N-glycosylated proteins with trypsin, Lys-C, Arg-N or chymotrypsin.

15. The method according to claim 8, wherein identifying a predetermined isotopic pattern comprises identifying a 1:2:1 peak intensity ratio in the mass spectrum.

16. The method according to claim 8, wherein the method further comprises determining an amino acid sequence of the low abundance protein.

17. The method according to claim 8, wherein the method further comprises generating an inclusion list of peptides having a mass spectrum that contains the predetermined isotopic pattern.

18. The method according to claim 17, wherein the method further comprises determining an amino acid sequence for each of the peptides on the inclusion list.

* * * * *

SEQUENCE LISTING

```
<160> NUMBER OF SEQ ID NOS: 134

<210> SEQ ID NO 1
<211> LENGTH: 12
<212> TYPE: PRT
<213> ORGANISM: Saccharomyces cerevisiae
<220> FEATURE:
<221> NAME/KEY: CARBOHYD
<222> LOCATION: (7)..(7)
<223> OTHER INFORMATION: the amino acid(s) in this region may be
      post-translationally modified by N-glycosylation

<400> SEQUENCE: 1

Asn Ser Ser Ser Ala Leu Asn Ile Thr Glu Leu Tyr
1               5                   10

<210> SEQ ID NO 2
<211> LENGTH: 23
<212> TYPE: PRT
<213> ORGANISM: Saccharomyces cerevisiae
```

```
<220> FEATURE:
<221> NAME/KEY: CARBOHYD
<222> LOCATION: (13)..(13)
<223> OTHER INFORMATION: the amino acid(s) in this region may be
      post-translationally modified by N-glycosylation
<220> FEATURE:
<221> NAME/KEY: CARBOHYD
<222> LOCATION: (20)..(20)
<223> OTHER INFORMATION: the amino acid(s) in this region may be
      post-translationally modified by N-glycosylation

<400> SEQUENCE: 2

Gln Ile Ile Val Thr Gly Gly Gln Val Pro Ile Thr Asn Ser Ser Leu
1               5                   10                  15

Thr His Thr Asn Tyr Thr Arg
            20

<210> SEQ ID NO 3
<211> LENGTH: 21
<212> TYPE: PRT
<213> ORGANISM: Saccharomyces cerevisiae
<220> FEATURE:
<221> NAME/KEY: CARBOHYD
<222> LOCATION: (4)..(4)
<223> OTHER INFORMATION: the amino acid(s) in this region may be
      post-translationally modified by N-glycosylation

<400> SEQUENCE: 3

Gln Asp Thr Asn Glu Pro Gln Thr Gly Gly Ile Glu Asp Ala Gly Gly
1               5                   10                  15

Ser Gly Thr Ile Lys
            20

<210> SEQ ID NO 4
<211> LENGTH: 18
<212> TYPE: PRT
<213> ORGANISM: Saccharomyces cerevisiae
<220> FEATURE:
<221> NAME/KEY: CARBOHYD
<222> LOCATION: (2)..(2)
<223> OTHER INFORMATION: the amino acid(s) in this region may be
      post-translationally modified by N-glycosylation
<220> FEATURE:
<221> NAME/KEY: CARBOHYD
<222> LOCATION: (5)..(5)
<223> OTHER INFORMATION: the amino acid(s) in this region may be
      post-translationally modified by N-glycosylation

<400> SEQUENCE: 4

Ala Asn Gly Thr Asn Ser Thr Thr Asn Thr Thr Thr Ala Glu Ser Ser
1               5                   10                  15

Gln Leu

<210> SEQ ID NO 5
<211> LENGTH: 13
<212> TYPE: PRT
<213> ORGANISM: Saccharomyces cerevisiae
<220> FEATURE:
<221> NAME/KEY: CARBOHYD
<222> LOCATION: (9)..(9)
<223> OTHER INFORMATION: the amino acid(s) in this region may be
      post-translationally modified by N-glycosylation

<400> SEQUENCE: 5

Asn Gln Asp Gly Ser Ser Lys Pro Asn Phe Thr Val Glu
1               5                   10

<210> SEQ ID NO 6
```

```
<211> LENGTH: 15
<212> TYPE: PRT
<213> ORGANISM: Saccharomyces cerevisiae
<220> FEATURE:
<221> NAME/KEY: CARBOHYD
<222> LOCATION: (11)..(11)
<223> OTHER INFORMATION: the amino acid(s) in this region may be
      post-translationally modified by N-glycosylation

<400> SEQUENCE: 6

Ser Ile Leu Phe Gln Gln Gln Asp Pro Phe Asn Glu Ser Ser Arg
1               5                   10                  15

<210> SEQ ID NO 7
<211> LENGTH: 14
<212> TYPE: PRT
<213> ORGANISM: Saccharomyces cerevisiae
<220> FEATURE:
<221> NAME/KEY: CARBOHYD
<222> LOCATION: (3)..(3)
<223> OTHER INFORMATION: the amino acid(s) in this region may be
      post-translationally modified by N-glycosylation

<400> SEQUENCE: 7

Ala Asn Asn Ile Thr Leu Arg Asp Val Asn Ser Ile Ser Phe
1               5                   10

<210> SEQ ID NO 8
<211> LENGTH: 18
<212> TYPE: PRT
<213> ORGANISM: Saccharomyces cerevisiae
<220> FEATURE:
<221> NAME/KEY: CARBOHYD
<222> LOCATION: (11)..(11)
<223> OTHER INFORMATION: the amino acid(s) in this region may be
      post-translationally modified by N-glycosylation
<220> FEATURE:
<221> NAME/KEY: MISC_FEATURE
<222> LOCATION: (14)..(14)
<223> OTHER INFORMATION: the amino acid(s) in this region may be
      post-translationally modified by carbamidomethylation

<400> SEQUENCE: 8

Gly Gly Ala Asn Phe Asp Ser Ser Ser Ser Asn Phe Ser Cys Asn Ala
1               5                   10                  15

Leu Lys

<210> SEQ ID NO 9
<211> LENGTH: 16
<212> TYPE: PRT
<213> ORGANISM: Saccharomyces cerevisiae
<220> FEATURE:
<221> NAME/KEY: CARBOHYD
<222> LOCATION: (15)..(15)
<223> OTHER INFORMATION: the amino acid(s) in this region may be
      post-translationally modified by N-glycosylation

<400> SEQUENCE: 9

Ser Ile Val Ser Asn Asp Glu Leu Ser Lys Ala Ala Phe Ser Asn Leu
1               5                   10                  15

<210> SEQ ID NO 10
<211> LENGTH: 15
<212> TYPE: PRT
<213> ORGANISM: Saccharomyces cerevisiae
<220> FEATURE:
<221> NAME/KEY: CARBOHYD
<222> LOCATION: (10)..(10)
<223> OTHER INFORMATION: the amino acid(s) in this region may be
      post-translationally modified by N-glycosylation
```

```
<400> SEQUENCE: 10

Thr Val Gly Gly Gly Phe Ile Ile Ala Asn Asn Thr Gln Leu Lys
1               5                   10                  15

<210> SEQ ID NO 11
<211> LENGTH: 19
<212> TYPE: PRT
<213> ORGANISM: Saccharomyces cerevisiae
<220> FEATURE:
<221> NAME/KEY: CARBOHYD
<222> LOCATION: (6)..(6)
<223> OTHER INFORMATION: the amino acid(s) in this region may be
      post-translationally modified by N-glycosylation

<400> SEQUENCE: 11

Gly Tyr Met Phe Glu Asn Gln Thr Ser Phe Pro Ile Phe Ala Ala Ser
1               5                   10                  15

Ser Glu Arg

<210> SEQ ID NO 12
<211> LENGTH: 11
<212> TYPE: PRT
<213> ORGANISM: Saccharomyces cerevisiae
<220> FEATURE:
<221> NAME/KEY: CARBOHYD
<222> LOCATION: (8)..(8)
<223> OTHER INFORMATION: the amino acid(s) in this region may be
      post-translationally modified by N-glycosylation

<400> SEQUENCE: 12

Ser Val Gly Ala Asn Leu Phe Asn Ala Thr Leu
1               5                   10

<210> SEQ ID NO 13
<211> LENGTH: 14
<212> TYPE: PRT
<213> ORGANISM: Saccharomyces cerevisiae
<220> FEATURE:
<221> NAME/KEY: MISC_FEATURE
<222> LOCATION: (6)..(6)
<223> OTHER INFORMATION: the amino acid(s) in this region may be
      post-translationally modified by carbamidomethylation
<220> FEATURE:
<221> NAME/KEY: CARBOHYD
<222> LOCATION: (8)..(8)
<223> OTHER INFORMATION: the amino acid(s) in this region may be
      post-translationally modified by N-glycosylation

<400> SEQUENCE: 13

Thr Glu Lys Phe Gln Cys Ser Asn Asp Thr Tyr Val Arg Tyr
1               5                   10

<210> SEQ ID NO 14
<211> LENGTH: 26
<212> TYPE: PRT
<213> ORGANISM: Saccharomyces cerevisiae
<220> FEATURE:
<221> NAME/KEY: CARBOHYD
<222> LOCATION: (11)..(11)
<223> OTHER INFORMATION: the amino acid(s) in this region may be
      post-translationally modified by N-glycosylation

<400> SEQUENCE: 14

Thr Thr Ala Gly Ile Ile Asp Asp Lys Asn Asn Leu Thr Ala Glu Tyr
1               5                   10                  15

Val Pro Phe Met Gly Asn Thr Phe His Lys
            20                  25
```

```
<210> SEQ ID NO 15
<211> LENGTH: 12
<212> TYPE: PRT
<213> ORGANISM: Saccharomyces cerevisiae
<220> FEATURE:
<221> NAME/KEY: CARBOHYD
<222> LOCATION: (8)..(8)
<223> OTHER INFORMATION: the amino acid(s) in this region may be
      post-translationally modified by N-glycosylation

<400> SEQUENCE: 15

Ser Val Gly Ser Asn Leu Phe Asn Ala Ser Val Lys
1               5                   10

<210> SEQ ID NO 16
<211> LENGTH: 15
<212> TYPE: PRT
<213> ORGANISM: Saccharomyces cerevisiae
<220> FEATURE:
<221> NAME/KEY: CARBOHYD
<222> LOCATION: (11)..(11)
<223> OTHER INFORMATION: the amino acid(s) in this region may be
      post-translationally modified by N-glycosylation

<400> SEQUENCE: 16

Thr Thr Ala Gly Ile Ile Asp Asp Lys Asn Asn Leu Thr Ala Glu
1               5                   10                  15

<210> SEQ ID NO 17
<211> LENGTH: 16
<212> TYPE: PRT
<213> ORGANISM: Saccharomyces cerevisiae
<220> FEATURE:
<221> NAME/KEY: MISC_FEATURE
<222> LOCATION: (6)..(6)
<223> OTHER INFORMATION: the amino acid(s) in this region may be
      post-translationally modified by carbamidomethylation
<220> FEATURE:
<221> NAME/KEY: CARBOHYD
<222> LOCATION: (9)..(9)
<223> OTHER INFORMATION: the amino acid(s) in this region may be
      post-translationally modified by N-glycosylation
<220> FEATURE:
<221> NAME/KEY: MISC_FEATURE
<222> LOCATION: (15)..(15)
<223> OTHER INFORMATION: the amino acid(s) in this region may be
      post-translationally modified by carbamidomethylation

<400> SEQUENCE: 17

Asp Ile Arg Gly Pro Cys Glu Asp Asn Ser Thr Asp Gly Met Cys Tyr
1               5                   10                  15

<210> SEQ ID NO 18
<211> LENGTH: 11
<212> TYPE: PRT
<213> ORGANISM: Saccharomyces cerevisiae
<220> FEATURE:
<221> NAME/KEY: CARBOHYD
<222> LOCATION: (8)..(8)
<223> OTHER INFORMATION: the amino acid(s) in this region may be
      post-translationally modified by N-glycosylation
<220> FEATURE:
<221> NAME/KEY: MISC_FEATURE
<222> LOCATION: (9)..(9)
<223> OTHER INFORMATION: the amino acid(s) in this region may be
      post-translationally modified by carbamidomethylation

<400> SEQUENCE: 18

Phe Val Pro Gly Ser Thr Ser Asn Cys Thr Phe
1               5                   10
```

```
<210> SEQ ID NO 19
<211> LENGTH: 17
<212> TYPE: PRT
<213> ORGANISM: Saccharomyces cerevisiae
<220> FEATURE:
<221> NAME/KEY: CARBOHYD
<222> LOCATION: (2)..(2)
<223> OTHER INFORMATION: the amino acid(s) in this region may be
      post-translationally modified by N-glycosylation

<400> SEQUENCE: 19

Ser Asn Asn Gly Thr Phe Phe Glu Thr Glu Glu Pro Ile Val Glu Thr
1               5                   10                  15

Lys

<210> SEQ ID NO 20
<211> LENGTH: 17
<212> TYPE: PRT
<213> ORGANISM: Saccharomyces cerevisiae
<220> FEATURE:
<221> NAME/KEY: CARBOHYD
<222> LOCATION: (9)..(9)
<223> OTHER INFORMATION: the amino acid(s) in this region may be
      post-translationally modified by N-glycosylation

<400> SEQUENCE: 20

Ile Ser Ser Phe Leu Ser Leu Ser Asn Ser Thr Ala Asp Thr Phe His
1               5                   10                  15

Leu

<210> SEQ ID NO 21
<211> LENGTH: 10
<212> TYPE: PRT
<213> ORGANISM: Saccharomyces cerevisiae
<220> FEATURE:
<221> NAME/KEY: CARBOHYD
<222> LOCATION: (6)..(6)
<223> OTHER INFORMATION: the amino acid(s) in this region may be
      post-translationally modified by N-glycosylation

<400> SEQUENCE: 21

Asn Asn Leu Gln His Asn Ile Thr Leu Lys
1               5                   10

<210> SEQ ID NO 22
<211> LENGTH: 14
<212> TYPE: PRT
<213> ORGANISM: Saccharomyces cerevisiae
<220> FEATURE:
<221> NAME/KEY: CARBOHYD
<222> LOCATION: (5)..(5)
<223> OTHER INFORMATION: the amino acid(s) in this region may be
      post-translationally modified by N-glycosylation

<400> SEQUENCE: 22

Ala His His Leu Asn Tyr Thr Leu Val Pro Phe Asp Gly Arg
1               5                   10

<210> SEQ ID NO 23
<211> LENGTH: 15
<212> TYPE: PRT
<213> ORGANISM: Saccharomyces cerevisiae
<220> FEATURE:
<221> NAME/KEY: CARBOHYD
<222> LOCATION: (3)..(3)
<223> OTHER INFORMATION: the amino acid(s) in this region may be
      post-translationally modified by N-glycosylation
```

-continued

<400> SEQUENCE: 23

Ala Tyr Asn Leu Thr Lys Glu Glu Asn Ser Lys Ile Arg Val Phe
1               5                   10                  15

<210> SEQ ID NO 24
<211> LENGTH: 13
<212> TYPE: PRT
<213> ORGANISM: Saccharomyces cerevisiae
<220> FEATURE:
<221> NAME/KEY: CARBOHYD
<222> LOCATION: (5)..(5)
<223> OTHER INFORMATION: the amino acid(s) in this region may be
      post-translationally modified by N-glycosylation

<400> SEQUENCE: 24

Ile Ile Ser Phe Asn Leu Ser Asp Ala Glu Thr Gly Lys
1               5                   10

<210> SEQ ID NO 25
<211> LENGTH: 11
<212> TYPE: PRT
<213> ORGANISM: Saccharomyces cerevisiae
<220> FEATURE:
<221> NAME/KEY: CARBOHYD
<222> LOCATION: (7)..(7)
<223> OTHER INFORMATION: the amino acid(s) in this region may be
      post-translationally modified by N-glycosylation

<400> SEQUENCE: 25

Ile Lys Val Asp Asp Leu Asn Ala Thr Ala Trp
1               5                   10

<210> SEQ ID NO 26
<211> LENGTH: 14
<212> TYPE: PRT
<213> ORGANISM: Saccharomyces cerevisiae
<220> FEATURE:
<221> NAME/KEY: CARBOHYD
<222> LOCATION: (3)..(3)
<223> OTHER INFORMATION: the amino acid(s) in this region may be
      post-translationally modified by N-glycosylation

<400> SEQUENCE: 26

Leu Ala Asn Tyr Ser Thr Pro Asp Tyr Gly His Pro Thr Arg
1               5                   10

<210> SEQ ID NO 27
<211> LENGTH: 20
<212> TYPE: PRT
<213> ORGANISM: Saccharomyces cerevisiae
<220> FEATURE:
<221> NAME/KEY: CARBOHYD
<222> LOCATION: (4)..(4)
<223> OTHER INFORMATION: the amino acid(s) in this region may be
      post-translationally modified by N-glycosylation

<400> SEQUENCE: 27

Ser Phe Ala Asn Thr Thr Ala Phe Ala Leu Ser Pro Pro Val Asp Gly
1               5                   10                  15

Phe Val Gly Lys
            20

<210> SEQ ID NO 28
<211> LENGTH: 23
<212> TYPE: PRT
<213> ORGANISM: Saccharomyces cerevisiae
<220> FEATURE:

```
<221> NAME/KEY: CARBOHYD
<222> LOCATION: (18)..(18)
<223> OTHER INFORMATION: the amino acid(s) in this region may be
      post-translationally modified by N-glycosylation
<220> FEATURE:
<221> NAME/KEY: MISC_FEATURE
<222> LOCATION: (21)..(21)
<223> OTHER INFORMATION: the amino acid(s) in this region may be
      post-translationally modified by oxidation

<400> SEQUENCE: 28

Ser Thr Pro Asp Tyr Gly His Pro Thr Arg Val Ile Gly Ser Lys Gly
1               5                   10                  15

His Asn Lys Thr Met Glu Tyr
            20

<210> SEQ ID NO 29
<211> LENGTH: 22
<212> TYPE: PRT
<213> ORGANISM: Saccharomyces cerevisiae
<220> FEATURE:
<221> NAME/KEY: CARBOHYD
<222> LOCATION: (13)..(13)
<223> OTHER INFORMATION: the amino acid(s) in this region may be
      post-translationally modified by N-glycosylation

<400> SEQUENCE: 29

Ala Pro Thr Tyr Gln Glu Leu Ala Asp Thr Tyr Ala Asn Ala Thr Ser
1               5                   10                  15

Asp Val Leu Ile Ala Lys
            20

<210> SEQ ID NO 30
<211> LENGTH: 21
<212> TYPE: PRT
<213> ORGANISM: Saccharomyces cerevisiae
<220> FEATURE:
<221> NAME/KEY: CARBOHYD
<222> LOCATION: (8)..(8)
<223> OTHER INFORMATION: the amino acid(s) in this region may be
      post-translationally modified by N-glycosylation

<400> SEQUENCE: 30

Asp Leu Pro Ala Tyr Leu Ala Asn Glu Thr Phe Val Thr Pro Val Ile
1               5                   10                  15

Val Gln Ser Gly Lys
            20

<210> SEQ ID NO 31
<211> LENGTH: 14
<212> TYPE: PRT
<213> ORGANISM: Saccharomyces cerevisiae
<220> FEATURE:
<221> NAME/KEY: CARBOHYD
<222> LOCATION: (5)..(5)
<223> OTHER INFORMATION: the amino acid(s) in this region may be
      post-translationally modified by N-glycosylation

<400> SEQUENCE: 31

Asn Ser Asp Val Asn Asn Ser Ile Asp Tyr Glu Gly Pro Arg
1               5                   10

<210> SEQ ID NO 32
<211> LENGTH: 23
<212> TYPE: PRT
<213> ORGANISM: Saccharomyces cerevisiae
<220> FEATURE:
<221> NAME/KEY: CARBOHYD
```

-continued

```
<222> LOCATION: (16)..(16)
<223> OTHER INFORMATION: the amino acid(s) in this region may be
      post-translationally modified by N-glycosylation

<400> SEQUENCE: 32

Lys Leu Asn Pro Gly Lys Asn Thr Asp Val Pro Ile Val Ala Asn Asn
1               5                   10                  15

His Ser Ser Ser His Ile Phe
            20

<210> SEQ ID NO 33
<211> LENGTH: 27
<212> TYPE: PRT
<213> ORGANISM: Saccharomyces cerevisiae
<220> FEATURE:
<221> NAME/KEY: MISC_FEATURE
<222> LOCATION: (17)..(17)
<223> OTHER INFORMATION: the amino acid(s) in this region may be
      post-translationally modified by carbamidomethylation
<220> FEATURE:
<221> NAME/KEY: CARBOHYD
<222> LOCATION: (19)..(19)
<223> OTHER INFORMATION: the amino acid(s) in this region may be
      post-translationally modified by N-glycosylation

<400> SEQUENCE: 33

Thr Ile Asp Glu Ile Gln Leu Asp Ser Asn Asp His Asn Ala Met Val
1               5                   10                  15

Cys Val Asn Ser Ser Ser Asn His Trp Gln Lys
            20                  25

<210> SEQ ID NO 34
<211> LENGTH: 11
<212> TYPE: PRT
<213> ORGANISM: Saccharomyces cerevisiae
<220> FEATURE:
<221> NAME/KEY: MISC_FEATURE
<222> LOCATION: (5)..(5)
<223> OTHER INFORMATION: the amino acid(s) in this region may be
      post-translationally modified by carbamidomethylation
<220> FEATURE:
<221> NAME/KEY: CARBOHYD
<222> LOCATION: (6)..(6)
<223> OTHER INFORMATION: the amino acid(s) in this region may be
      post-translationally modified by N-glycosylation

<400> SEQUENCE: 34

Val Phe Ser Gly Cys Asn Val Thr Asn Glu Lys
1               5                   10

<210> SEQ ID NO 35
<211> LENGTH: 18
<212> TYPE: PRT
<213> ORGANISM: Saccharomyces cerevisiae
<220> FEATURE:
<221> NAME/KEY: CARBOHYD
<222> LOCATION: (12)..(12)
<223> OTHER INFORMATION: the amino acid(s) in this region may be
      post-translationally modified by N-glycosylation

<400> SEQUENCE: 35

Asn Ala Pro Gly Glu Ser Leu Thr Thr Phe Gln Asn Leu Thr Asp Gly
1               5                   10                  15

Thr Lys

<210> SEQ ID NO 36
<211> LENGTH: 13
<212> TYPE: PRT
```

```
<213> ORGANISM: Saccharomyces cerevisiae
<220> FEATURE:
<221> NAME/KEY: CARBOHYD
<222> LOCATION: (3)..(3)
<223> OTHER INFORMATION: the amino acid(s) in this region may be
      post-translationally modified by N-glycosylation

<400> SEQUENCE: 36

Ala Asn Asn Ile Ser Leu Thr Asp Val His Ser Val Ser
1               5                   10

<210> SEQ ID NO 37
<211> LENGTH: 13
<212> TYPE: PRT
<213> ORGANISM: Saccharomyces cerevisiae
<220> FEATURE:
<221> NAME/KEY: CARBOHYD
<222> LOCATION: (9)..(9)
<223> OTHER INFORMATION: the amino acid(s) in this region may be
      post-translationally modified by N-glycosylation

<400> SEQUENCE: 37

Ile Asn Asn Ser Ile Ser Ser Leu Asn Phe Thr Lys Leu
1               5                   10

<210> SEQ ID NO 38
<211> LENGTH: 21
<212> TYPE: PRT
<213> ORGANISM: Saccharomyces cerevisiae
<220> FEATURE:
<221> NAME/KEY: CARBOHYD
<222> LOCATION: (18)..(18)
<223> OTHER INFORMATION: the amino acid(s) in this region may be
      post-translationally modified by N-glycosylation

<400> SEQUENCE: 38

Ala Ile Val Phe Pro Ser Ala Ser Ser Ser Pro Asp Gly Leu Ala Phe
1               5                   10                  15

Ile Asn Gly Thr Arg
            20

<210> SEQ ID NO 39
<211> LENGTH: 10
<212> TYPE: PRT
<213> ORGANISM: Saccharomyces cerevisiae
<220> FEATURE:
<221> NAME/KEY: CARBOHYD
<222> LOCATION: (5)..(5)
<223> OTHER INFORMATION: the amino acid(s) in this region may be
      post-translationally modified by N-glycosylation

<400> SEQUENCE: 39

Glu Met Glu Val Asn Gly Thr Ser Lys Phe
1               5                   10

<210> SEQ ID NO 40
<211> LENGTH: 21
<212> TYPE: PRT
<213> ORGANISM: Saccharomyces cerevisiae
<220> FEATURE:
<221> NAME/KEY: CARBOHYD
<222> LOCATION: (3)..(3)
<223> OTHER INFORMATION: the amino acid(s) in this region may be
      post-translationally modified by N-glycosylation

<400> SEQUENCE: 40

Gly Val Asn Gly Thr Ile Val Thr Tyr Pro His Gly Tyr Pro Val Ala
1               5                   10                  15
```

```
Asp Ile Thr Gly Ala
            20

<210> SEQ ID NO 41
<211> LENGTH: 21
<212> TYPE: PRT
<213> ORGANISM: Saccharomyces cerevisiae
<220> FEATURE:
<221> NAME/KEY: CARBOHYD
<222> LOCATION: (7)..(7)
<223> OTHER INFORMATION: the amino acid(s) in this region may be
      post-translationally modified by N-glycosylation

<400> SEQUENCE: 41

Leu Glu Tyr Leu Asp Ile Asn Ser Thr Ser Thr Val Asp Leu Tyr
1               5                  10                  15

Asp Lys Glu Gln Arg
            20

<210> SEQ ID NO 42
<211> LENGTH: 17
<212> TYPE: PRT
<213> ORGANISM: Saccharomyces cerevisiae
<220> FEATURE:
<221> NAME/KEY: CARBOHYD
<222> LOCATION: (8)..(8)
<223> OTHER INFORMATION: the amino acid(s) in this region may be
      post-translationally modified by N-glycosylation

<400> SEQUENCE: 42

Leu Thr Leu Ser Pro Ser Gly Asn Asp Ser Glu Thr Gln Tyr Tyr Thr
1               5                  10                  15

Thr

<210> SEQ ID NO 43
<211> LENGTH: 16
<212> TYPE: PRT
<213> ORGANISM: Saccharomyces cerevisiae
<220> FEATURE:
<221> NAME/KEY: CARBOHYD
<222> LOCATION: (6)..(6)
<223> OTHER INFORMATION: the amino acid(s) in this region may be
      post-translationally modified by N-glycosylation

<400> SEQUENCE: 43

Ile Trp Pro Gly Gly Asn Ser Thr Asn Ala Pro Gly Thr Ile Ala Trp
1               5                  10                  15

<210> SEQ ID NO 44
<211> LENGTH: 16
<212> TYPE: PRT
<213> ORGANISM: Saccharomyces cerevisiae
<220> FEATURE:
<221> NAME/KEY: CARBOHYD
<222> LOCATION: (12)..(12)
<223> OTHER INFORMATION: the amino acid(s) in this region may be
      post-translationally modified by N-glycosylation

<400> SEQUENCE: 44

Asn Gly Gly Gly Gln Asp Leu Ser Ala Phe Trp Asn Asp Thr Lys Lys
1               5                  10                  15

<210> SEQ ID NO 45
<211> LENGTH: 21
<212> TYPE: PRT
<213> ORGANISM: Saccharomyces cerevisiae
<220> FEATURE:
<221> NAME/KEY: CARBOHYD
```

-continued

```
<222> LOCATION: (15)..(15)
<223> OTHER INFORMATION: the amino acid(s) in this region may be
      post-translationally modified by N-glycosylation

<400> SEQUENCE: 45

Thr Lys Glu Tyr Asn Asp Leu Glu Ser Asn Thr Val Val Ser Asn Ser
1               5                   10                  15

Thr Leu Gly Val Lys
            20

<210> SEQ ID NO 46
<211> LENGTH: 19
<212> TYPE: PRT
<213> ORGANISM: Saccharomyces cerevisiae
<220> FEATURE:
<221> NAME/KEY: CARBOHYD
<222> LOCATION: (10)..(10)
<223> OTHER INFORMATION: the amino acid(s) in this region may be
      post-translationally modified by N-glycosylation

<400> SEQUENCE: 46

Thr Thr Leu Val Asp Asn Asn Thr Trp Asn Asn Thr His Ile Ala Ile
1               5                   10                  15

Val Gly Lys

<210> SEQ ID NO 47
<211> LENGTH: 22
<212> TYPE: PRT
<213> ORGANISM: Saccharomyces cerevisiae
<220> FEATURE:
<221> NAME/KEY: CARBOHYD
<222> LOCATION: (8)..(8)
<223> OTHER INFORMATION: the amino acid(s) in this region may be
      post-translationally modified by N-glycosylation

<400> SEQUENCE: 47

Glu Leu Ser Asn Leu Ile Thr Asn Ser Ser Ala Phe Tyr Thr Asp
1               5                   10                  15

Gly Met Gly Thr Ala Lys
            20

<210> SEQ ID NO 48
<211> LENGTH: 12
<212> TYPE: PRT
<213> ORGANISM: Saccharomyces cerevisiae
<220> FEATURE:
<221> NAME/KEY: CARBOHYD
<222> LOCATION: (3)..(3)
<223> OTHER INFORMATION: the amino acid(s) in this region may be
      post-translationally modified by N-glycosylation

<400> SEQUENCE: 48

Phe His Asn Tyr Thr Leu Asp Trp Ala Met Asp Lys
1               5                   10

<210> SEQ ID NO 49
<211> LENGTH: 13
<212> TYPE: PRT
<213> ORGANISM: Saccharomyces cerevisiae
<220> FEATURE:
<221> NAME/KEY: CARBOHYD
<222> LOCATION: (2)..(2)
<223> OTHER INFORMATION: the amino acid(s) in this region may be
      post-translationally modified by N-glycosylation

<400> SEQUENCE: 49

Ser Asn Thr Ser Ser Glu Gly Tyr Pro Gln Ser Pro Met
```

```
<210> SEQ ID NO 50
<211> LENGTH: 13
<212> TYPE: PRT
<213> ORGANISM: Saccharomyces cerevisiae
<220> FEATURE:
<221> NAME/KEY: CARBOHYD
<222> LOCATION: (10)..(10)
<223> OTHER INFORMATION: the amino acid(s) in this region may be
      post-translationally modified by N-glycosylation

<400> SEQUENCE: 50

Ser Tyr Trp Gln Gly Gln Thr Met Gln Asn Ala Ser Tyr
1               5                   10

<210> SEQ ID NO 51
<211> LENGTH: 17
<212> TYPE: PRT
<213> ORGANISM: Saccharomyces cerevisiae
<220> FEATURE:
<221> NAME/KEY: CARBOHYD
<222> LOCATION: (11)..(11)
<223> OTHER INFORMATION: the amino acid(s) in this region may be
      post-translationally modified by N-glycosylation

<400> SEQUENCE: 51

Asn Thr Pro Asp Tyr Gln Glu Pro Asn Ser Asn Tyr Thr Asn Asp Gly
1               5                   10                  15

Lys

<210> SEQ ID NO 52
<211> LENGTH: 22
<212> TYPE: PRT
<213> ORGANISM: Saccharomyces cerevisiae
<220> FEATURE:
<221> NAME/KEY: CARBOHYD
<222> LOCATION: (8)..(8)
<223> OTHER INFORMATION: the amino acid(s) in this region may be
      post-translationally modified by N-glycosylation

<400> SEQUENCE: 52

Thr Phe Ile His Asn Gly Gln Asn Leu Thr Val Glu Ser Ile Thr Ala
1               5                   10                  15

Ser Pro Asp Leu Lys Arg
            20

<210> SEQ ID NO 53
<211> LENGTH: 16
<212> TYPE: PRT
<213> ORGANISM: Saccharomyces cerevisiae
<220> FEATURE:
<221> NAME/KEY: CARBOHYD
<222> LOCATION: (2)..(2)
<223> OTHER INFORMATION: the amino acid(s) in this region may be
      post-translationally modified by N-glycosylation

<400> SEQUENCE: 53

Gly Asn Asn Thr Glu Asp Phe Gln Pro Phe Ile Asp Ser Glu Lys Arg
1               5                   10                  15

<210> SEQ ID NO 54
<211> LENGTH: 16
<212> TYPE: PRT
<213> ORGANISM: Saccharomyces cerevisiae
<220> FEATURE:
<221> NAME/KEY: CARBOHYD
<222> LOCATION: (12)..(12)
```

```
<223> OTHER INFORMATION: the amino acid(s) in this region may be
      post-translationally modified by N-glycosylation

<400> SEQUENCE: 54

Ser Tyr Ala Ser Asp Ile Gly Ala Pro Leu Phe Asn Ser Thr Glu Lys
1               5                   10                  15

<210> SEQ ID NO 55
<211> LENGTH: 17
<212> TYPE: PRT
<213> ORGANISM: Saccharomyces cerevisiae
<220> FEATURE:
<221> NAME/KEY: CARBOHYD
<222> LOCATION: (3)..(3)
<223> OTHER INFORMATION: the amino acid(s) in this region may be
      post-translationally modified by N-glycosylation

<400> SEQUENCE: 55

Ser Ile Asn Met Thr Asp Pro Val Asp Ala Glu Ser Pro Ile Phe Ser
1               5                   10                  15

Arg

<210> SEQ ID NO 56
<211> LENGTH: 20
<212> TYPE: PRT
<213> ORGANISM: Saccharomyces cerevisiae
<220> FEATURE:
<221> NAME/KEY: CARBOHYD
<222> LOCATION: (11)..(11)
<223> OTHER INFORMATION: the amino acid(s) in this region may be
      post-translationally modified by N-glycosylation
<220> FEATURE:
<221> NAME/KEY: MISC_FEATURE
<222> LOCATION: (15)..(15)
<223> OTHER INFORMATION: the amino acid(s) in this region may be
      post-translationally modified by carbamidomethylation

<400> SEQUENCE: 56

Ala Met Thr Ile Gln Gly Leu Gly Ala Gln Asn Lys Ser Ser Cys Glu
1               5                   10                  15

His Glu Thr Phe
            20

<210> SEQ ID NO 57
<211> LENGTH: 16
<212> TYPE: PRT
<213> ORGANISM: Saccharomyces cerevisiae
<220> FEATURE:
<221> NAME/KEY: CARBOHYD
<222> LOCATION: (6)..(6)
<223> OTHER INFORMATION: the amino acid(s) in this region may be
      post-translationally modified by N-glycosylation

<400> SEQUENCE: 57

Ala Val Gln Pro Thr Asn Asp Ser Met Val Leu Gly Asp Val Phe Leu
1               5                   10                  15

<210> SEQ ID NO 58
<211> LENGTH: 15
<212> TYPE: PRT
<213> ORGANISM: Saccharomyces cerevisiae
<220> FEATURE:
<221> NAME/KEY: CARBOHYD
<222> LOCATION: (9)..(9)
<223> OTHER INFORMATION: the amino acid(s) in this region may be
      post-translationally modified by N-glycosylation

<400> SEQUENCE: 58
```

```
Ile Ser Leu Ala Gln Ala Asn Trp Asn Ala Ser Glu Val Ser Lys
1               5                   10                  15

<210> SEQ ID NO 59
<211> LENGTH: 19
<212> TYPE: PRT
<213> ORGANISM: Saccharomyces cerevisiae
<220> FEATURE:
<221> NAME/KEY: CARBOHYD
<222> LOCATION: (5)..(5)
<223> OTHER INFORMATION: the amino acid(s) in this region may be
      post-translationally modified by N-glycosylation

<400> SEQUENCE: 59

Gln Leu Leu Ala Asn Ser Thr Thr Ala Pro Gly Asp Asp Gly Glu Ser
1               5                   10                  15

Glu Ile Arg

<210> SEQ ID NO 60
<211> LENGTH: 11
<212> TYPE: PRT
<213> ORGANISM: Saccharomyces cerevisiae
<220> FEATURE:
<221> NAME/KEY: CARBOHYD
<222> LOCATION: (2)..(2)
<223> OTHER INFORMATION: the amino acid(s) in this region may be
      post-translationally modified by N-glycosylation

<400> SEQUENCE: 60

Thr Asn Val Ser Ile Glu Thr Gln Lys Ser Tyr
1               5                   10

<210> SEQ ID NO 61
<211> LENGTH: 14
<212> TYPE: PRT
<213> ORGANISM: Saccharomyces cerevisiae
<220> FEATURE:
<221> NAME/KEY: CARBOHYD
<222> LOCATION: (11)..(11)
<223> OTHER INFORMATION: the amino acid(s) in this region may be
      post-translationally modified by N-glycosylation

<400> SEQUENCE: 61

Ala Phe Tyr Thr Ser Pro Gly Phe Thr Val Asn Asn Ser Arg
1               5                   10

<210> SEQ ID NO 62
<211> LENGTH: 15
<212> TYPE: PRT
<213> ORGANISM: Saccharomyces cerevisiae
<220> FEATURE:
<221> NAME/KEY: CARBOHYD
<222> LOCATION: (7)..(7)
<223> OTHER INFORMATION: the amino acid(s) in this region may be
      post-translationally modified by N-glycosylation

<400> SEQUENCE: 62

Asp Ile Phe Glu Ala Met Asn Gly Thr Glu Lys Asn His Leu Tyr
1               5                   10                  15

<210> SEQ ID NO 63
<211> LENGTH: 18
<212> TYPE: PRT
<213> ORGANISM: Saccharomyces cerevisiae
<220> FEATURE:
<221> NAME/KEY: CARBOHYD
<222> LOCATION: (11)..(11)
<223> OTHER INFORMATION: the amino acid(s) in this region may be
      post-translationally modified by N-glycosylation
```

<400> SEQUENCE: 63

Glu Phe Glu Met Pro Thr Glu Thr Glu Lys Asn Ser Ser Ser Ile Gly
1               5                   10                  15

Tyr Tyr

<210> SEQ ID NO 64
<211> LENGTH: 11
<212> TYPE: PRT
<213> ORGANISM: Saccharomyces cerevisiae
<220> FEATURE:
<221> NAME/KEY: CARBOHYD
<222> LOCATION: (6)..(6)
<223> OTHER INFORMATION: the amino acid(s) in this region may be
      post-translationally modified by N-glycosylation

<400> SEQUENCE: 64

Gly Tyr Ile Thr Arg Asn Thr Thr Gly Thr Met
1               5                   10

<210> SEQ ID NO 65
<211> LENGTH: 13
<212> TYPE: PRT
<213> ORGANISM: Saccharomyces cerevisiae
<220> FEATURE:
<221> NAME/KEY: CARBOHYD
<222> LOCATION: (5)..(5)
<223> OTHER INFORMATION: the amino acid(s) in this region may be
      post-translationally modified by N-glycosylation
<220> FEATURE:
<221> NAME/KEY: MISC_FEATURE
<222> LOCATION: (8)..(8)
<223> OTHER INFORMATION: the amino acid(s) in this region may be
      post-translationally modified by carbamidomethylation

<400> SEQUENCE: 65

Ile Ile Tyr Ser Asn Val Ser Cys Pro Lys Ser Gly Tyr
1               5                   10

<210> SEQ ID NO 66
<211> LENGTH: 18
<212> TYPE: PRT
<213> ORGANISM: Saccharomyces cerevisiae
<220> FEATURE:
<221> NAME/KEY: CARBOHYD
<222> LOCATION: (6)..(6)
<223> OTHER INFORMATION: the amino acid(s) in this region may be
      post-translationally modified by N-glycosylation
<220> FEATURE:
<221> NAME/KEY: MISC_FEATURE
<222> LOCATION: (9)..(9)
<223> OTHER INFORMATION: the amino acid(s) in this region may be
      post-translationally modified by carbamidomethylation
<220> FEATURE:
<221> NAME/KEY: MISC_FEATURE
<222> LOCATION: (11)..(11)
<223> OTHER INFORMATION: the amino acid(s) in this region may be
      post-translationally modified by carbamidomethylation

<400> SEQUENCE: 66

Lys Asp Ile Thr Asn Asn Glu Ser Cys Thr Cys Glu Val Gly Asp Arg
1               5                   10                  15

Val Trp

<210> SEQ ID NO 67
<211> LENGTH: 11
<212> TYPE: PRT
<213> ORGANISM: Saccharomyces cerevisiae
<220> FEATURE:

```
<221> NAME/KEY: CARBOHYD
<222> LOCATION: (7)..(7)
<223> OTHER INFORMATION: the amino acid(s) in this region may be
      post-translationally modified by N-glycosylation
<220> FEATURE:
<221> NAME/KEY: MISC_FEATURE
<222> LOCATION: (8)..(8)
<223> OTHER INFORMATION: the amino acid(s) in this region may be
      post-translationally modified by carbamidomethylation
<220> FEATURE:
<221> NAME/KEY: MISC_FEATURE
<222> LOCATION: (10)..(10)
<223> OTHER INFORMATION: the amino acid(s) in this region may be
      post-translationally modified by carbamidomethylation

<400> SEQUENCE: 67

Gln Tyr Pro Thr Asn Ala Asn Cys Ser Cys Trp
1               5                   10

<210> SEQ ID NO 68
<211> LENGTH: 22
<212> TYPE: PRT
<213> ORGANISM: Saccharomyces cerevisiae
<220> FEATURE:
<221> NAME/KEY: CARBOHYD
<222> LOCATION: (4)..(4)
<223> OTHER INFORMATION: the amino acid(s) in this region may be
      post-translationally modified by N-glycosylation
<220> FEATURE:
<221> NAME/KEY: MISC_FEATURE
<222> LOCATION: (17)..(17)
<223> OTHER INFORMATION: the amino acid(s) in this region may be
      post-translationally modified by carbamidomethylation

<400> SEQUENCE: 68

Thr Ala Asp Asn Val Thr Phe Leu Asn His Gly Gly Glu Ala Ser Pro
1               5                   10                  15

Cys Leu Gly Asn Ala Leu
            20

<210> SEQ ID NO 69
<211> LENGTH: 17
<212> TYPE: PRT
<213> ORGANISM: Saccharomyces cerevisiae
<220> FEATURE:
<221> NAME/KEY: CARBOHYD
<222> LOCATION: (10)..(10)
<223> OTHER INFORMATION: the amino acid(s) in this region may be
      post-translationally modified by N-glycosylation

<400> SEQUENCE: 69

Ala His Gln Asp Val Val Pro Val Asn Asn Glu Thr Leu Ser Ser Trp
1               5                   10                  15

Lys

<210> SEQ ID NO 70
<211> LENGTH: 17
<212> TYPE: PRT
<213> ORGANISM: Saccharomyces cerevisiae
<220> FEATURE:
<221> NAME/KEY: CARBOHYD
<222> LOCATION: (16)..(16)
<223> OTHER INFORMATION: the amino acid(s) in this region may be
      post-translationally modified by N-glycosylation

<400> SEQUENCE: 70

Glu Phe Glu Ala Ile Glu Gln Leu Leu Ile Asp Gly Phe Lys Pro Asn
1               5                   10                  15

Arg
```

-continued

```
<210> SEQ ID NO 71
<211> LENGTH: 17
<212> TYPE: PRT
<213> ORGANISM: Saccharomyces cerevisiae
<220> FEATURE:
<221> NAME/KEY: CARBOHYD
<222> LOCATION: (9)..(9)
<223> OTHER INFORMATION: the amino acid(s) in this region may be
      post-translationally modified by N-glycosylation

<400> SEQUENCE: 71

Gly Arg Leu Asp Leu Ala Ala Ser Asn Ile Thr Gly Phe Val Ser Thr
1               5                   10                  15
Arg

<210> SEQ ID NO 72
<211> LENGTH: 13
<212> TYPE: PRT
<213> ORGANISM: Saccharomyces cerevisiae
<220> FEATURE:
<221> NAME/KEY: CARBOHYD
<222> LOCATION: (4)..(4)
<223> OTHER INFORMATION: the amino acid(s) in this region may be
      post-translationally modified by N-glycosylation

<400> SEQUENCE: 72

Thr Ser Thr Asn Arg Ser Leu Ala Asn Pro Ile Met Thr
1               5                   10

<210> SEQ ID NO 73
<211> LENGTH: 17
<212> TYPE: PRT
<213> ORGANISM: Saccharomyces cerevisiae
<220> FEATURE:
<221> NAME/KEY: CARBOHYD
<222> LOCATION: (10)..(10)
<223> OTHER INFORMATION: the amino acid(s) in this region may be
      post-translationally modified by N-glycosylation
<220> FEATURE:
<221> NAME/KEY: MISC_FEATURE
<222> LOCATION: (11)..(11)
<223> OTHER INFORMATION: the amino acid(s) in this region may be
      post-translationally modified by carbamidomethylation

<400> SEQUENCE: 73

Val Tyr Asp Gly Val Ser Ile Asp Asp Asn Cys Thr Lys Val Thr Ser
1               5                   10                  15
Tyr

<210> SEQ ID NO 74
<211> LENGTH: 13
<212> TYPE: PRT
<213> ORGANISM: Saccharomyces cerevisiae
<220> FEATURE:
<221> NAME/KEY: CARBOHYD
<222> LOCATION: (4)..(4)
<223> OTHER INFORMATION: the amino acid(s) in this region may be
      post-translationally modified by N-glycosylation

<400> SEQUENCE: 74

Tyr Thr Gly Asn Gln Thr Tyr Val Asp Trp Ala Glu Lys
1               5                   10

<210> SEQ ID NO 75
<211> LENGTH: 16
<212> TYPE: PRT
<213> ORGANISM: Saccharomyces cerevisiae
```

```
<220> FEATURE:
<221> NAME/KEY: CARBOHYD
<222> LOCATION: (8)..(8)
<223> OTHER INFORMATION: the amino acid(s) in this region may be
      post-translationally modified by N-glycosylation

<400> SEQUENCE: 75

Thr Tyr Gly Glu Thr Val Gly Asn Tyr Thr Leu Thr Val Glu Asn Lys
1               5                   10                  15

<210> SEQ ID NO 76
<211> LENGTH: 11
<212> TYPE: PRT
<213> ORGANISM: Saccharomyces cerevisiae
<220> FEATURE:
<221> NAME/KEY: CARBOHYD
<222> LOCATION: (6)..(6)
<223> OTHER INFORMATION: the amino acid(s) in this region may be
      post-translationally modified by N-glycosylation

<400> SEQUENCE: 76

Met Trp Asn Gln Gln Asn Asn Thr Ile Met Lys
1               5                   10

<210> SEQ ID NO 77
<211> LENGTH: 12
<212> TYPE: PRT
<213> ORGANISM: Saccharomyces cerevisiae
<220> FEATURE:
<221> NAME/KEY: CARBOHYD
<222> LOCATION: (1)..(1)
<223> OTHER INFORMATION: the amino acid(s) in this region may be
      post-translationally modified by N-glycosylation

<400> SEQUENCE: 77

Asn Ser Ser Leu Tyr Ala Asp Ile Tyr Asp Asn Lys
1               5                   10

<210> SEQ ID NO 78
<211> LENGTH: 21
<212> TYPE: PRT
<213> ORGANISM: Saccharomyces cerevisiae
<220> FEATURE:
<221> NAME/KEY: CARBOHYD
<222> LOCATION: (9)..(9)
<223> OTHER INFORMATION: the amino acid(s) in this region may be
      post-translationally modified by N-glycosylation

<400> SEQUENCE: 78

Thr Asp Pro Ser Ser Ser Ile Met Asn Leu Thr Tyr Leu Asp Pro Leu
1               5                   10                  15

Ser Gly Glu Leu Lys
            20

<210> SEQ ID NO 79
<211> LENGTH: 25
<212> TYPE: PRT
<213> ORGANISM: Saccharomyces cerevisiae
<220> FEATURE:
<221> NAME/KEY: CARBOHYD
<222> LOCATION: (19)..(19)
<223> OTHER INFORMATION: the amino acid(s) in this region may be
      post-translationally modified by N-glycosylation

<400> SEQUENCE: 79

Leu Val Asp Ser Thr Asn Pro Ile Gly Thr Thr Glu Ser Leu Ile Thr
1               5                   10                  15

Leu Asn Asn Met Thr Thr Glu Glu Lys
```

<210> SEQ ID NO 80
<211> LENGTH: 15
<212> TYPE: PRT
<213> ORGANISM: Saccharomyces cerevisiae
<220> FEATURE:
<221> NAME/KEY: CARBOHYD
<222> LOCATION: (7)..(7)
<223> OTHER INFORMATION: the amino acid(s) in this region may be
      post-translationally modified by N-glycosylation

<400> SEQUENCE: 80

Ser Thr Met Ile Ala Glu Asn Ile Thr Gln Ser Ser Ser Ala Lys
1               5                   10                  15

<210> SEQ ID NO 81
<211> LENGTH: 12
<212> TYPE: PRT
<213> ORGANISM: Saccharomyces cerevisiae
<220> FEATURE:
<221> NAME/KEY: CARBOHYD
<222> LOCATION: (8)..(8)
<223> OTHER INFORMATION: the amino acid(s) in this region may be
      post-translationally modified by N-glycosylation

<400> SEQUENCE: 81

Ile Pro Thr Glu Leu Val Ser Glu Asn Gly Thr Lys
1               5                   10

<210> SEQ ID NO 82
<211> LENGTH: 19
<212> TYPE: PRT
<213> ORGANISM: Saccharomyces cerevisiae
<220> FEATURE:
<221> NAME/KEY: CARBOHYD
<222> LOCATION: (7)..(7)
<223> OTHER INFORMATION: the amino acid(s) in this region may be
      post-translationally modified by N-glycosylation

<400> SEQUENCE: 82

Phe Tyr Trp Val Gln Gly Asn Thr Thr Gly Ile Pro Asn Ala Gly Asp
1               5                   10                  15

Glu Thr Arg

<210> SEQ ID NO 83
<211> LENGTH: 13
<212> TYPE: PRT
<213> ORGANISM: Saccharomyces cerevisiae
<220> FEATURE:
<221> NAME/KEY: MISC_FEATURE
<222> LOCATION: (8)..(8)
<223> OTHER INFORMATION: the amino acid(s) in this region may be
      post-translationally modified by carbamidomethylation
<220> FEATURE:
<221> NAME/KEY: CARBOHYD
<222> LOCATION: (9)..(9)
<223> OTHER INFORMATION: the amino acid(s) in this region may be
      post-translationally modified by N-glycosylation

<400> SEQUENCE: 83

Asn Asp His Val Ser Pro Ser Cys Asn Val Thr Phe Asn
1               5                   10

<210> SEQ ID NO 84
<211> LENGTH: 13
<212> TYPE: PRT
<213> ORGANISM: Saccharomyces cerevisiae
<220> FEATURE:

```
<221> NAME/KEY: CARBOHYD
<222> LOCATION: (2)..(2)
<223> OTHER INFORMATION: the amino acid(s) in this region may be
      post-translationally modified by N-glycosylation

<400> SEQUENCE: 84

Thr Asn Asn Ser Gln Ser His Val Phe Asp Asp Leu Lys
1               5                   10

<210> SEQ ID NO 85
<211> LENGTH: 19
<212> TYPE: PRT
<213> ORGANISM: Saccharomyces cerevisiae
<220> FEATURE:
<221> NAME/KEY: CARBOHYD
<222> LOCATION: (1)..(1)
<223> OTHER INFORMATION: the amino acid(s) in this region may be
      post-translationally modified by N-glycosylation

<400> SEQUENCE: 85

Asn Leu Thr Asp Leu Glu Tyr Ile Pro Pro Leu Val Val Tyr Ile Pro
1               5                   10                  15

Asn Thr Lys

<210> SEQ ID NO 86
<211> LENGTH: 16
<212> TYPE: PRT
<213> ORGANISM: Saccharomyces cerevisiae
<220> FEATURE:
<221> NAME/KEY: CARBOHYD
<222> LOCATION: (9)..(9)
<223> OTHER INFORMATION: the amino acid(s) in this region may be
      post-translationally modified by N-glycosylation

<400> SEQUENCE: 86

Ser Ile Val Asn Pro Gly Gly Ser Asn Leu Thr Tyr Thr Ile Glu Arg
1               5                   10                  15

<210> SEQ ID NO 87
<211> LENGTH: 13
<212> TYPE: PRT
<213> ORGANISM: Saccharomyces cerevisiae
<220> FEATURE:
<221> NAME/KEY: CARBOHYD
<222> LOCATION: (6)..(6)
<223> OTHER INFORMATION: the amino acid(s) in this region may be
      post-translationally modified by N-glycosylation

<400> SEQUENCE: 87

Ser Arg Ala Thr Ser Asn Phe Ser Asp Thr Ser Leu Leu
1               5                   10

<210> SEQ ID NO 88
<211> LENGTH: 15
<212> TYPE: PRT
<213> ORGANISM: Saccharomyces cerevisiae
<220> FEATURE:
<221> NAME/KEY: MISC_FEATURE
<222> LOCATION: (8)..(8)
<223> OTHER INFORMATION: the amino acid(s) in this region may be
      post-translationally modified by oxidation
<220> FEATURE:
<221> NAME/KEY: CARBOHYD
<222> LOCATION: (14)..(14)
<223> OTHER INFORMATION: the amino acid(s) in this region may be
      post-translationally modified by N-glycosylation

<400> SEQUENCE: 88

Ala Met Leu Ser Gly Ala Gly Met Leu Ala Ala Met Asp Asn Arg
```

```
1               5                  10                 15
```

<210> SEQ ID NO 89
<211> LENGTH: 19
<212> TYPE: PRT
<213> ORGANISM: Saccharomyces cerevisiae
<220> FEATURE:
<221> NAME/KEY: CARBOHYD
<222> LOCATION: (2)..(2)
<223> OTHER INFORMATION: the amino acid(s) in this region may be
      post-translationally modified by N-glycosylation
<220> FEATURE:
<221> NAME/KEY: MISC_FEATURE
<222> LOCATION: (12)..(12)
<223> OTHER INFORMATION: the amino acid(s) in this region may be
      post-translationally modified by carbamidomethylation
<220> FEATURE:
<221> NAME/KEY: MISC_FEATURE
<222> LOCATION: (15)..(15)
<223> OTHER INFORMATION: the amino acid(s) in this region may be
      post-translationally modified by carbamidomethylation

<400> SEQUENCE: 89

```
Gly Asn Phe Thr Asp Asp Ser Asp Phe Leu Gly Cys Val Gly Cys Ala
1               5                  10                 15

Ile Ile Arg
```

<210> SEQ ID NO 90
<211> LENGTH: 15
<212> TYPE: PRT
<213> ORGANISM: Saccharomyces cerevisiae
<220> FEATURE:
<221> NAME/KEY: CARBOHYD
<222> LOCATION: (11)..(11)
<223> OTHER INFORMATION: the amino acid(s) in this region may be
      post-translationally modified by N-glycosylation

<400> SEQUENCE: 90

```
Ile Pro Asn Ser Arg His Ser Phe Asn Gly Asn Gln Ser Thr Phe
1               5                  10                 15
```

<210> SEQ ID NO 91
<211> LENGTH: 14
<212> TYPE: PRT
<213> ORGANISM: Saccharomyces cerevisiae
<220> FEATURE:
<221> NAME/KEY: CARBOHYD
<222> LOCATION: (4)..(4)
<223> OTHER INFORMATION: the amino acid(s) in this region may be
      post-translationally modified by N-glycosylation

<400> SEQUENCE: 91

```
Leu Gln Lys Asn Ala Thr Ser Ser Ile Ile Glu Ser Glu Tyr
1               5                  10
```

<210> SEQ ID NO 92
<211> LENGTH: 13
<212> TYPE: PRT
<213> ORGANISM: Saccharomyces cerevisiae
<220> FEATURE:
<221> NAME/KEY: CARBOHYD
<222> LOCATION: (6)..(6)
<223> OTHER INFORMATION: the amino acid(s) in this region may be
      post-translationally modified by N-glycosylation

<400> SEQUENCE: 92

```
Asn Arg Ala Thr Ser Asn Phe Ser Asp Thr Ser Leu Leu
1               5                  10
```

-continued

```
<210> SEQ ID NO 93
<211> LENGTH: 17
<212> TYPE: PRT
<213> ORGANISM: Saccharomyces cerevisiae
<220> FEATURE:
<221> NAME/KEY: CARBOHYD
<222> LOCATION: (9)..(9)
<223> OTHER INFORMATION: the amino acid(s) in this region may be
      post-translationally modified by N-glycosylation

<400> SEQUENCE: 93

Thr Ser Val Gln Ala Ile Val Asp Asn Thr Thr Glu Ser Asn Ser Ile
1               5                   10                  15

Trp

<210> SEQ ID NO 94
<211> LENGTH: 16
<212> TYPE: PRT
<213> ORGANISM: Saccharomyces cerevisiae
<220> FEATURE:
<221> NAME/KEY: CARBOHYD
<222> LOCATION: (10)..(10)
<223> OTHER INFORMATION: the amino acid(s) in this region may be
      post-translationally modified by N-glycosylation

<400> SEQUENCE: 94

Glu Ile Asp Gly Ile Thr Thr Glu Lys Asn Val Thr Asp Met Leu Tyr
1               5                   10                  15

<210> SEQ ID NO 95
<211> LENGTH: 18
<212> TYPE: PRT
<213> ORGANISM: Saccharomyces cerevisiae
<220> FEATURE:
<221> NAME/KEY: CARBOHYD
<222> LOCATION: (16)..(16)
<223> OTHER INFORMATION: the amino acid(s) in this region may be
      post-translationally modified by N-glycosylation

<400> SEQUENCE: 95

Phe Asp Asp Thr Met Leu Asp Val Ile Pro Ser Asp Leu Gln Leu Asn
1               5                   10                  15

Ala Thr

<210> SEQ ID NO 96
<211> LENGTH: 17
<212> TYPE: PRT
<213> ORGANISM: Saccharomyces cerevisiae
<220> FEATURE:
<221> NAME/KEY: CARBOHYD
<222> LOCATION: (10)..(10)
<223> OTHER INFORMATION: the amino acid(s) in this region may be
      post-translationally modified by N-glycosylation

<400> SEQUENCE: 96

Asn Gly Val Asn Tyr Ala Phe Phe Asn Asn Ile Thr Tyr Thr Ala Pro
1               5                   10                  15

Lys

<210> SEQ ID NO 97
<211> LENGTH: 19
<212> TYPE: PRT
<213> ORGANISM: Saccharomyces cerevisiae
<220> FEATURE:
<221> NAME/KEY: CARBOHYD
<222> LOCATION: (7)..(7)
<223> OTHER INFORMATION: the amino acid(s) in this region may be
      post-translationally modified by N-glycosylation
```

```
<400> SEQUENCE: 97

Ser Ser Gly Asp Gln Ala Asn Asn Ser Glu Ile Tyr Gly Ser Asn Thr
1               5                   10                  15

His Thr Phe

<210> SEQ ID NO 98
<211> LENGTH: 14
<212> TYPE: PRT
<213> ORGANISM: Saccharomyces cerevisiae
<220> FEATURE:
<221> NAME/KEY: CARBOHYD
<222> LOCATION: (8)..(8)
<223> OTHER INFORMATION: the amino acid(s) in this region may be
      post-translationally modified by N-glycosylation

<400> SEQUENCE: 98

Thr Val Leu Val His Thr Lys Asn Asp Thr Asp Lys Asn Phe
1               5                   10

<210> SEQ ID NO 99
<211> LENGTH: 12
<212> TYPE: PRT
<213> ORGANISM: Saccharomyces cerevisiae
<220> FEATURE:
<221> NAME/KEY: CARBOHYD
<222> LOCATION: (4)..(4)
<223> OTHER INFORMATION: the amino acid(s) in this region may be
      post-translationally modified by N-glycosylation

<400> SEQUENCE: 99

Ser Arg Tyr Asn Gln Thr Glu Thr Phe Lys Glu Tyr
1               5                   10

<210> SEQ ID NO 100
<211> LENGTH: 14
<212> TYPE: PRT
<213> ORGANISM: Saccharomyces cerevisiae
<220> FEATURE:
<221> NAME/KEY: CARBOHYD
<222> LOCATION: (8)..(8)
<223> OTHER INFORMATION: the amino acid(s) in this region may be
      post-translationally modified by N-glycosylation
<220> FEATURE:
<221> NAME/KEY: MISC_FEATURE
<222> LOCATION: (9)..(9)
<223> OTHER INFORMATION: the amino acid(s) in this region may be
      post-translationally modified by carbamidomethylation

<400> SEQUENCE: 100

Asp Gly Ala Glu Ile Asp Thr Asn Cys Thr Asp Ile Thr Lys
1               5                   10

<210> SEQ ID NO 101
<211> LENGTH: 11
<212> TYPE: PRT
<213> ORGANISM: Saccharomyces cerevisiae
<220> FEATURE:
<221> NAME/KEY: CARBOHYD
<222> LOCATION: (7)..(7)
<223> OTHER INFORMATION: the amino acid(s) in this region may be
      post-translationally modified by N-glycosylation

<400> SEQUENCE: 101

Ile Leu Gly Ile Asp Pro Asn Val Thr Gln Tyr
1               5                   10

<210> SEQ ID NO 102
```

```
<211> LENGTH: 17
<212> TYPE: PRT
<213> ORGANISM: Saccharomyces cerevisiae
<220> FEATURE:
<221> NAME/KEY: CARBOHYD
<222> LOCATION: (3)..(3)
<223> OTHER INFORMATION: the amino acid(s) in this region may be
      post-translationally modified by N-glycosylation

<400> SEQUENCE: 102

Val Arg Asn Trp Thr Ala Ser Ile Thr Asp Glu Val Ala Gly Glu Val
1               5                   10                  15

Lys

<210> SEQ ID NO 103
<211> LENGTH: 17
<212> TYPE: PRT
<213> ORGANISM: Saccharomyces cerevisiae
<220> FEATURE:
<221> NAME/KEY: CARBOHYD
<222> LOCATION: (8)..(8)
<223> OTHER INFORMATION: the amino acid(s) in this region may be
      post-translationally modified by N-glycosylation

<400> SEQUENCE: 103

Ala Gly Asn Glu Val Thr Asn Asn Tyr Thr Asn Thr Asp Ala Ser Ala
1               5                   10                  15

Phe

<210> SEQ ID NO 104
<211> LENGTH: 12
<212> TYPE: PRT
<213> ORGANISM: Saccharomyces cerevisiae
<220> FEATURE:
<221> NAME/KEY: CARBOHYD
<222> LOCATION: (3)..(3)
<223> OTHER INFORMATION: the amino acid(s) in this region may be
      post-translationally modified by N-glycosylation
<220> FEATURE:
<221> NAME/KEY: MISC_FEATURE
<222> LOCATION: (11)..(11)
<223> OTHER INFORMATION: the amino acid(s) in this region may be
      post-translationally modified by carbamidomethylation
<220> FEATURE:
<221> NAME/KEY: MISC_FEATURE
<222> LOCATION: (12)..(12)
<223> OTHER INFORMATION: the amino acid(s) in this region may be
      post-translationally modified by oxidation

<400> SEQUENCE: 104

Ala Ile Asn Thr Thr Leu Asp His Ser Glu Cys Met
1               5                   10

<210> SEQ ID NO 105
<211> LENGTH: 11
<212> TYPE: PRT
<213> ORGANISM: Saccharomyces cerevisiae
<220> FEATURE:
<221> NAME/KEY: CARBOHYD
<222> LOCATION: (6)..(6)
<223> OTHER INFORMATION: the amino acid(s) in this region may be
      post-translationally modified by N-glycosylation

<400> SEQUENCE: 105

Phe Phe Tyr Ser Asn Asn Gly Ser Gln Phe Tyr
1               5                   10

<210> SEQ ID NO 106
<211> LENGTH: 21
```

```
<212> TYPE: PRT
<213> ORGANISM: Saccharomyces cerevisiae
<220> FEATURE:
<221> NAME/KEY: MISC_FEATURE
<222> LOCATION: (5)..(5)
<223> OTHER INFORMATION: the amino acid(s) in this region may be
      post-translationally modified by carbamidomethylation
<220> FEATURE:
<221> NAME/KEY: MISC_FEATURE
<222> LOCATION: (10)..(10)
<223> OTHER INFORMATION: the amino acid(s) in this region may be
      post-translationally modified by carbamidomethylation
<220> FEATURE:
<221> NAME/KEY: CARBOHYD
<222> LOCATION: (16)..(16)
<223> OTHER INFORMATION: the amino acid(s) in this region may be
      post-translationally modified by N-glycosylation

<400> SEQUENCE: 106

Phe Asn Trp Ile Cys Asn Glu Val Asp Cys Ser Gly Ile Ser Ala Asn
1               5                   10                  15

Gly Thr Ala Gly Lys
            20

<210> SEQ ID NO 107
<211> LENGTH: 29
<212> TYPE: PRT
<213> ORGANISM: Saccharomyces cerevisiae
<220> FEATURE:
<221> NAME/KEY: CARBOHYD
<222> LOCATION: (10)..(10)
<223> OTHER INFORMATION: the amino acid(s) in this region may be
      post-translationally modified by N-glycosylation
<220> FEATURE:
<221> NAME/KEY: MISC_FEATURE
<222> LOCATION: (27)..(27)
<223> OTHER INFORMATION: the amino acid(s) in this region may be
      post-translationally modified by carbamidomethylation

<400> SEQUENCE: 107

Gly Val Ala Tyr Gln Ala Asp Thr Ala Asn Glu Thr Ser Gly Ser Thr
1               5                   10                  15

Val Asn Asp Pro Leu Ala Asn Tyr Glu Ser Cys Ser Arg
            20                  25

<210> SEQ ID NO 108
<211> LENGTH: 13
<212> TYPE: PRT
<213> ORGANISM: Saccharomyces cerevisiae
<220> FEATURE:
<221> NAME/KEY: CARBOHYD
<222> LOCATION: (9)..(9)
<223> OTHER INFORMATION: the amino acid(s) in this region may be
      post-translationally modified by N-glycosylation

<400> SEQUENCE: 108

Lys Thr Val Val Asp Thr Phe Ala Asn Tyr Thr Asn Val
1               5                   10

<210> SEQ ID NO 109
<211> LENGTH: 19
<212> TYPE: PRT
<213> ORGANISM: Saccharomyces cerevisiae
<220> FEATURE:
<221> NAME/KEY: CARBOHYD
<222> LOCATION: (1)..(1)
<223> OTHER INFORMATION: the amino acid(s) in this region may be
      post-translationally modified by N-glycosylation
<220> FEATURE:
<221> NAME/KEY: MISC_FEATURE
<222> LOCATION: (13)..(13)
```

```
<223> OTHER INFORMATION: the amino acid(s) in this region may be
      post-translationally modified by carbamidomethylation

<400> SEQUENCE: 109

Asn Leu Ser Ile Pro Val Phe Phe Ser Glu Tyr Gly Cys Asn Glu Val
1               5                   10                  15

Thr Pro Arg

<210> SEQ ID NO 110
<211> LENGTH: 11
<212> TYPE: PRT
<213> ORGANISM: Saccharomyces cerevisiae
<220> FEATURE:
<221> NAME/KEY: CARBOHYD
<222> LOCATION: (4)..(4)
<223> OTHER INFORMATION: the amino acid(s) in this region may be
      post-translationally modified by N-glycosylation

<400> SEQUENCE: 110

Glu Tyr Ser Asn Phe Thr Thr Pro Tyr Gly Leu
1               5                   10

<210> SEQ ID NO 111
<211> LENGTH: 16
<212> TYPE: PRT
<213> ORGANISM: Saccharomyces cerevisiae
<220> FEATURE:
<221> NAME/KEY: CARBOHYD
<222> LOCATION: (8)..(8)
<223> OTHER INFORMATION: the amino acid(s) in this region may be
      post-translationally modified by N-glycosylation

<400> SEQUENCE: 111

Gly Gly Gln Val Pro Ile Thr Asn Ser Ser Leu Thr His Thr Asn Tyr
1               5                   10                  15

<210> SEQ ID NO 112
<211> LENGTH: 13
<212> TYPE: PRT
<213> ORGANISM: Saccharomyces cerevisiae
<220> FEATURE:
<221> NAME/KEY: CARBOHYD
<222> LOCATION: (7)..(7)
<223> OTHER INFORMATION: the amino acid(s) in this region may be
      post-translationally modified by N-glycosylation

<400> SEQUENCE: 112

Asn Val Ala Arg Val Val Asn Glu Thr Ile Gln Asp Lys
1               5                   10

<210> SEQ ID NO 113
<211> LENGTH: 21
<212> TYPE: PRT
<213> ORGANISM: Saccharomyces cerevisiae
<220> FEATURE:
<221> NAME/KEY: CARBOHYD
<222> LOCATION: (13)..(13)
<223> OTHER INFORMATION: the amino acid(s) in this region may be
      post-translationally modified by N-glycosylation
<220> FEATURE:
<221> NAME/KEY: CARBOHYD
<222> LOCATION: (20)..(20)

<400> SEQUENCE: 113

Gln Ile Ile Val Thr Gly Gly Gln Val Pro Ile Thr Asn Ser Ser Leu
1               5                   10                  15

Thr His Thr Asn Tyr
                20
```

<210> SEQ ID NO 114
<211> LENGTH: 20
<212> TYPE: PRT
<213> ORGANISM: Saccharomyces cerevisiae
<220> FEATURE:
<221> NAME/KEY: CARBOHYD
<222> LOCATION: (5)..(5)
<223> OTHER INFORMATION: the amino acid(s) in this region may be
      post-translationally modified by N-glycosylation

<400> SEQUENCE: 114

Ser Gly Ser Thr Asn Ser Thr Ser Ser Thr Ile Glu Ser Thr Glu Ile
1               5                   10                  15

Pro Val Val Tyr
            20

<210> SEQ ID NO 115
<211> LENGTH: 34
<212> TYPE: PRT
<213> ORGANISM: Saccharomyces cerevisiae
<220> FEATURE:
<221> NAME/KEY: CARBOHYD
<222> LOCATION: (27)..(27)
<223> OTHER INFORMATION: the amino acid(s) in this region may be
      post-translationally modified by N-glycosylation

<400> SEQUENCE: 115

Ser Ile Ile Phe Asp Thr Glu Lys Pro Ile Val Val Thr Glu Asp Ser
1               5                   10                  15

Ala Tyr Ala Ile Pro Val Ala Asn Asn Lys Asn Ala Thr Lys Arg Gly
            20                  25                  30

Val Leu

<210> SEQ ID NO 116
<211> LENGTH: 10
<212> TYPE: PRT
<213> ORGANISM: Saccharomyces cerevisiae
<220> FEATURE:
<221> NAME/KEY: CARBOHYD
<222> LOCATION: (5)..(5)
<223> OTHER INFORMATION: the amino acid(s) in this region may be
      post-translationally modified by N-glycosylation

<400> SEQUENCE: 116

Thr Arg Leu Phe Asn Ser Ser Ser Ala Leu
1               5                   10

<210> SEQ ID NO 117
<211> LENGTH: 12
<212> TYPE: PRT
<213> ORGANISM: Saccharomyces cerevisiae
<220> FEATURE:
<221> NAME/KEY: CARBOHYD
<222> LOCATION: (4)..(4)
<223> OTHER INFORMATION: the amino acid(s) in this region may be
      post-translationally modified by N-glycosylation

<400> SEQUENCE: 117

Ser Thr Asn Asn Phe Thr Ile Ser Ile Pro Glu Lys
1               5                   10

<210> SEQ ID NO 118
<211> LENGTH: 15
<212> TYPE: PRT
<213> ORGANISM: Saccharomyces cerevisiae
<220> FEATURE:

```
<221> NAME/KEY: CARBOHYD
<222> LOCATION: (4)..(4)
<223> OTHER INFORMATION: the amino acid(s) in this region may be
      post-translationally modified by N-glycosylation

<400> SEQUENCE: 118

Val Ala Lys Asn Thr Ser Ala Ile Thr Thr Asp Gly Gly Ile Tyr
1               5                   10                  15

<210> SEQ ID NO 119
<211> LENGTH: 16
<212> TYPE: PRT
<213> ORGANISM: Saccharomyces cerevisiae
<220> FEATURE:
<221> NAME/KEY: CARBOHYD
<222> LOCATION: (2)..(2)
<223> OTHER INFORMATION: the amino acid(s) in this region may be
      post-translationally modified by N-glycosylation

<400> SEQUENCE: 119

Leu Asn Gly Thr Trp Ala Ala Asp Asn Lys Asp Trp Val Asn Ser Leu
1               5                   10                  15

<210> SEQ ID NO 120
<211> LENGTH: 14
<212> TYPE: PRT
<213> ORGANISM: Saccharomyces cerevisiae
<220> FEATURE:
<221> NAME/KEY: CARBOHYD
<222> LOCATION: (4)..(4)
<223> OTHER INFORMATION: the amino acid(s) in this region may be
      post-translationally modified by N-glycosylation

<400> SEQUENCE: 120

Ala Thr Ala Asn Phe Ser Asp Ser Ser Glu Val Leu Ser Lys
1               5                   10

<210> SEQ ID NO 121
<211> LENGTH: 15
<212> TYPE: PRT
<213> ORGANISM: Saccharomyces cerevisiae
<220> FEATURE:
<221> NAME/KEY: CARBOHYD
<222> LOCATION: (8)..(8)
<223> OTHER INFORMATION: the amino acid(s) in this region may be
      post-translationally modified by N-glycosylation

<400> SEQUENCE: 121

Glu Ala Thr Ser Ile Ser Gln Asn Glu Ser Ala Trp Leu Glu Lys
1               5                   10                  15

<210> SEQ ID NO 122
<211> LENGTH: 19
<212> TYPE: PRT
<213> ORGANISM: Saccharomyces cerevisiae
<220> FEATURE:
<221> NAME/KEY: CARBOHYD
<222> LOCATION: (2)..(2)
<223> OTHER INFORMATION: the amino acid(s) in this region may be
      post-translationally modified by N-glycosylation
<220> FEATURE:
<221> NAME/KEY: MISC_FEATURE
<222> LOCATION: (12)..(12)
<223> OTHER INFORMATION: the amino acid(s) in this region may be
      post-translationally modified by carbamidomethylation
<220> FEATURE:
<221> NAME/KEY: MISC_FEATURE
<222> LOCATION: (15)..(15)
<223> OTHER INFORMATION: the amino acid(s) in this region may be
      post-translationally modified by carbamidomethylation
```

```
<400> SEQUENCE: 122

Asn Asn Phe Thr Asp Asp Pro Glu Phe Met Gly Cys Val Gly Cys Ala
1               5                   10                  15

Ile Ile Arg

<210> SEQ ID NO 123
<211> LENGTH: 17
<212> TYPE: PRT
<213> ORGANISM: Saccharomyces cerevisiae
<220> FEATURE:
<221> NAME/KEY: CARBOHYD
<222> LOCATION: (10)..(10)
<223> OTHER INFORMATION: the amino acid(s) in this region may be
      post-translationally modified by N-glycosylation

<400> SEQUENCE: 123

Ala Gly Asn Glu Val Ile Asn Ser Val Asn Thr Thr Asn Thr Ala Thr
1               5                   10                  15

Tyr

<210> SEQ ID NO 124
<211> LENGTH: 14
<212> TYPE: PRT
<213> ORGANISM: Saccharomyces cerevisiae
<220> FEATURE:
<221> NAME/KEY: CARBOHYD
<222> LOCATION: (5)..(5)
<223> OTHER INFORMATION: the amino acid(s) in this region may be
      post-translationally modified by N-glycosylation

<400> SEQUENCE: 124

Ala Ser Ser Ser Asn Ser Ser Thr Pro Ser Ile Glu Ile Lys
1               5                   10

<210> SEQ ID NO 125
<211> LENGTH: 24
<212> TYPE: PRT
<213> ORGANISM: Saccharomyces cerevisiae
<220> FEATURE:
<221> NAME/KEY: CARBOHYD
<222> LOCATION: (11)..(11)
<223> OTHER INFORMATION: the amino acid(s) in this region may be
      post-translationally modified by N-glycosylation
<220> FEATURE:
<221> NAME/KEY: MISC_FEATURE
<222> LOCATION: (22)..(22)
<223> OTHER INFORMATION: the amino acid(s) in this region may be
      post-translationally modified by carbamidomethylation

<400> SEQUENCE: 125

Gly Val Asp Tyr Gln Pro Gly Gly Ser Ser Asn Leu Thr Asp Pro Leu
1               5                   10                  15

Ala Asp Ala Ser Val Cys Asp Arg
            20

<210> SEQ ID NO 126
<211> LENGTH: 27
<212> TYPE: PRT
<213> ORGANISM: Saccharomyces cerevisiae
<220> FEATURE:
<221> NAME/KEY: CARBOHYD
<222> LOCATION: (10)..(10)
<223> OTHER INFORMATION: the amino acid(s) in this region may be
      post-translationally modified by N-glycosylation
```

```
<400> SEQUENCE: 126

Ser Gly Gly Leu Val Tyr Glu Tyr Ser Asn Glu Thr Asn Asn Tyr Gly
1               5                   10                  15

Leu Val Gln Ile Asp Gly Asp Lys Val Thr Lys
            20                  25

<210> SEQ ID NO 127
<211> LENGTH: 18
<212> TYPE: PRT
<213> ORGANISM: Saccharomyces cerevisiae
<220> FEATURE:
<221> NAME/KEY: CARBOHYD
<222> LOCATION: (17)..(17)
<223> OTHER INFORMATION: the amino acid(s) in this region may be
      post-translationally modified by N-glycosylation

<400> SEQUENCE: 127

Ser Lys Val Ser Asn Pro Glu Gly Asn Gly Gly Tyr Ser Thr Ser Asn
1               5                   10                  15

Asn Tyr

<210> SEQ ID NO 128
<211> LENGTH: 19
<212> TYPE: PRT
<213> ORGANISM: Saccharomyces cerevisiae
<220> FEATURE:
<221> NAME/KEY: CARBOHYD
<222> LOCATION: (3)..(3)
<223> OTHER INFORMATION: the amino acid(s) in this region may be
      post-translationally modified by N-glycosylation

<400> SEQUENCE: 128

Asp Thr Asn Ser Thr Ala Glu Leu Gln Ser Pro Ser Ser Gln Glu Ile
1               5                   10                  15

Leu Gly Trp

<210> SEQ ID NO 129
<211> LENGTH: 16
<212> TYPE: PRT
<213> ORGANISM: Saccharomyces cerevisiae
<220> FEATURE:
<221> NAME/KEY: CARBOHYD
<222> LOCATION: (10)..(10)
<223> OTHER INFORMATION: the amino acid(s) in this region may be
      post-translationally modified by N-glycosylation

<400> SEQUENCE: 129

Glu Glu Val Val Asp Tyr Thr Gln Asn Asn Ala Thr Tyr Ala Val Arg
1               5                   10                  15

<210> SEQ ID NO 130
<211> LENGTH: 20
<212> TYPE: PRT
<213> ORGANISM: Saccharomyces cerevisiae
<220> FEATURE:
<221> NAME/KEY: MISC_FEATURE
<222> LOCATION: (14)..(14)
<223> OTHER INFORMATION: the amino acid(s) in this region may be
      post-translationally modified by carbamidomethylation
<220> FEATURE:
<221> NAME/KEY: CARBOHYD
<222> LOCATION: (15)..(15)
<223> OTHER INFORMATION: the amino acid(s) in this region may be
      post-translationally modified by N-glycosylation
```

```
<400> SEQUENCE: 130

Gly Trp Ser His Ala Thr Phe Pro Thr Ile Tyr Gln Thr Cys Asn Glu
1               5                   10                  15

Thr Asn Ala Arg
            20

<210> SEQ ID NO 131
<211> LENGTH: 21
<212> TYPE: PRT
<213> ORGANISM: Saccharomyces cerevisiae
<220> FEATURE:
<221> NAME/KEY: CARBOHYD
<222> LOCATION: (14)..(14)
<223> OTHER INFORMATION: the amino acid(s) in this region may be
      post-translationally modified by N-glycosylation

<400> SEQUENCE: 131

Thr Leu Asp Asn Asp Gly Asn Asp Ile Pro Val Gly Leu Asn Asp Ser
1               5                   10                  15

Val Ala Tyr Ser Lys
            20

<210> SEQ ID NO 132
<211> LENGTH: 17
<212> TYPE: PRT
<213> ORGANISM: Saccharomyces cerevisiae
<220> FEATURE:
<221> NAME/KEY: MISC_FEATURE
<222> LOCATION: (6)..(6)
<223> OTHER INFORMATION: the amino acid(s) in this region may be
      post-translationally modified by carbamidomethylation
<220> FEATURE:
<221> NAME/KEY: MISC_FEATURE
<222> LOCATION: (14)..(14)
<223> OTHER INFORMATION: the amino acid(s) in this region may be
      post-translationally modified by carbamidomethylation
<220> FEATURE:
<221> NAME/KEY: CARBOHYD
<222> LOCATION: (16)..(16)
<223> OTHER INFORMATION: the amino acid(s) in this region may be
      post-translationally modified by N-glycosylation

<400> SEQUENCE: 132

Gly Ile Glu Pro Asn Cys Pro Ile Asn Ile Pro Leu Ser Cys Ser Asn
1               5                   10                  15

Lys

<210> SEQ ID NO 133
<211> LENGTH: 10
<212> TYPE: PRT
<213> ORGANISM: Saccharomyces cerevisiae
<220> FEATURE:
<221> NAME/KEY: CARBOHYD
<222> LOCATION: (2)..(2)
<223> OTHER INFORMATION: the amino acid(s) in this region may be
      post-translationally modified by N-glycosylation

<400> SEQUENCE: 133

Ala Asn Gly Thr Glu Phe Ala Ile Gln Tyr
1               5                   10

<210> SEQ ID NO 134
<211> LENGTH: 10
<212> TYPE: PRT
<213> ORGANISM: Saccharomyces cerevisiae
```

```
<220> FEATURE:
<221> NAME/KEY: CARBOHYD
<222> LOCATION: (4)..(4)
<223> OTHER INFORMATION: the amino acid(s) in this region may be
      post-translationally modified by N-glycosylation

<400> SEQUENCE: 134

Asn Gly Tyr Asn Phe Thr Ile Gly Pro Tyr
1               5                   10
```